(12) United States Patent
Lingam et al.

(10) Patent No.: US 8,344,010 B2
(45) Date of Patent: Jan. 1, 2013

(54) FUSED IMIDAZOLE DERIVATIVES AS TRPV3 ANTAGONIST

(75) Inventors: V. S. Prasadarao Lingam, Navi Mumbai (IN); Abraham Thomas, Navi Mumbai (IN); Shantaram Kashinath Phatangare, Navi Mumbai (IN); Ajit Shankar Mindhe, Pune (IN); Javed Yusuf Khatik, Thane (IN); Neelima Khairatkar-Joshi, Thane (IN); Vidya Ganapati Kattige, Thane (IN)

(73) Assignee: Glenmark Pharmaceuticals S.A., La Chaux-de-Fonds (CH)

( * ) Notice: Subject to any disclaimer, the term of this patent is extended or adjusted under 35 U.S.C. 154(b) by 0 days.

(21) Appl. No.: 13/141,199

(22) PCT Filed: Dec. 23, 2009

(86) PCT No.: PCT/IB2009/008018
§ 371 (c)(1), (2), (4) Date: Jun. 21, 2011

(87) PCT Pub. No.: WO2010/073128
PCT Pub. Date: Jul. 1, 2010

(65) Prior Publication Data
US 2011/0257193 A1    Oct. 20, 2011

Related U.S. Application Data

(60) Provisional application No. 61/146,865, filed on Jan. 23, 2009, provisional application No. 61/237,434, filed on Aug. 27, 2009.

(30) Foreign Application Priority Data

Dec. 26, 2008 (IN) .......................... 2705/MUM/2008
Jul. 29, 2009 (IN) .......................... 1732/MUM/2009

(51) Int. Cl.
| | |
|---|---|
| *A61K 31/506* | (2006.01) |
| *A61K 31/501* | (2006.01) |
| *A61K 31/4439* | (2006.01) |
| *A61K 31/428* | (2006.01) |
| *A61K 31/427* | (2006.01) |
| *A61K 31/4184* | (2006.01) |
| *C07D 417/04* | (2006.01) |
| *C07D 409/04* | (2006.01) |
| *C07D 401/04* | (2006.01) |
| *C07D 403/04* | (2006.01) |

(52) U.S. Cl. ................... 514/394; 514/252.06; 514/338; 514/275; 514/365; 514/367; 548/304.4; 548/304.7; 548/181; 548/159; 546/273.4; 544/238; 544/331

(58) Field of Classification Search ............... 548/310.1, 548/304.4, 304.7, 181, 159; 514/394, 338, 514/252.06, 275, 365, 367; 546/273.4; 544/238, 544/331
See application file for complete search history.

(56) References Cited

U.S. PATENT DOCUMENTS
4,769,384 A * 9/1988 Kise et al. ..................... 514/394

FOREIGN PATENT DOCUMENTS
WO    WO2007059608 A1    5/2007

OTHER PUBLICATIONS

Hcaplus 1987:102171 Abstract, "Application of phase-transfer catalysis to the synthesis of mono- and bisstilbenes and -styryls", Lokhande et. al., 1986.*
Lokhande, S. B. et al.: "Application of Phase-Transfer Catalysis to the Synthesis of mono- & Bis-stilbenes & Styryls", Indian Journal of Chemistry, vol. 25B, Nov. 25, 1985, pp. 485-488.
International Search Report dated, Mar. 26, 2012 for corresponding International Patent Application No. PCT/IB2009/008018.
Written Opinion of the International Searching Authority for corresponding International Patent Application No. PCT/IB2009/008018, 2012.

* cited by examiner

*Primary Examiner* — Joseph Kosack
*Assistant Examiner* — Matthew Coughlin
(74) *Attorney, Agent, or Firm* — Gilman Pergament LLP

(57) ABSTRACT

The present invention provides transient receptor potential vanilloid (TRPV) modulators of formula (I). In particular, compounds described herein are useful for treating or preventing diseases, conditions and/or disorders modulated by TRPV3. Also provided herein are processes for preparing compounds described herein, intermediates used in their synthesis, pharmaceutical compositions thereof, and methods for treating or preventing diseases, conditions and/or disorders modulated by TRPV3.

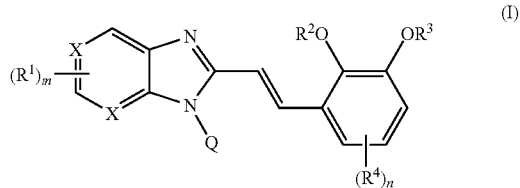

40 Claims, No Drawings

FUSED IMIDAZOLE DERIVATIVES AS TRPV3 ANTAGONIST

RELATED APPLICATIONS

This application is a National Stage Application under 35 U.S.C. 371 of PCT International Application No. PCT/IB2009/008018, filed Dec. 23, 2009, which claims priority to Indian Provisional Applications 2705/MUM/2008, filed on Dec. 26, 2008; 1732/MUM/2009, filed on Jul. 29, 2009; and U.S. Provisional Applications 61/146,865, filed on Jan. 23, 2009; 61/237,434, filed on Aug. 27, 2009; all of which are hereby incorporated by reference in their entirety.

TECHNICAL FIELD

The present patent application relates generally to fused imidazole derivatives with transient receptor potential vanilloid 3 (TRPV3) antagonist activity.

BACKGROUND OF THE INVENTION

Movement of ions across cellular membranes is carried out by specialized proteins. TRP channels are one large family of non-selective cation channels that function to help regulate ion flux and membrane potential. TRP channels are subdivided into 6 sub-families including the TRPV family. TRPV3 is a member of the TRPV class of TRP channels.

TRPV3 is a calcium permeable channel, specifically a calcium permeable nonselective cation channel. In addition to calcium ions, TRPV3 channels are permeable to other cations, for example sodium. Thus, TRPV3 channels modulate membrane potential by modulating the flux of cations such as calcium and sodium ions. TRPV3 receptors are mechanistically distinct from voltage-gated calcium channels. Generally, voltage-gated calcium channels respond to membrane depolarization and open to permit an influx of calcium from the extracellular medium that result in an increase in intracellular calcium levels or concentrations. In contrast, TRP channels which are non-selective cation channels are generally ligand gated (such as 2-aminoethoxydiphenyl borate [2-APB], heat, and vanilloids), long lasting, and produce more prolonged changes in ion concentration. These mechanistic differences are accompanied by structural differences among voltage-gated and TRP channels. Thus, although many diverse channels act to regulate ion flux and membrane potential in various cell types and in response to numerous stimuli, it is important to recognize the significant structural, functional, and mechanistic differences among different classes of ion channels.

TRPV3 proteins are thermosensitive channels expressed in skin cells (Peier et al. *Science* (2002), 296, 2046-2049) and dorsal root ganglion, trigeminal ganglion, spinal cord and brain (Xu et al. *Nature* (2002), 418, 181-185; Smith et al. *Nature* (2002), 418, 186-188). TRPV3 is also highly expressed in skin. In a keratinocyte cell line, stimulation of TRPV3 leads to release of inflammatory mediators including interleukin-1. Thus TRPV3 may also play an important role in regulating inflammation and pain that results from the release of inflammatory stimuli. Particular TRPV3 proteins that may be used in screening assays, as described herein, to identify compounds that modulate a function of TRPV3 include, but are not limited to human TRPV3, mouse TRPV3, rat TRPV3 and Drosophila TRPV3. US 2004/0009537 (the '537 application) disclosed sequences corresponding to human, mouse, and Drosophila TRPV3. For example, SEQ ID Nos 106 and 107 of the '537 application correspond to the human nucleic acid and amino acid sequences, respectively. SEQ ID Nos 108 and 109 of the '537 application correspond to the mouse nucleic acid and amino acid sequences, respectively.

TRPV3 function has been basically implicated in the reception and transduction of pain. Accordingly, it would be desirable to identify and make compounds that can modulate one or more functions of TRPV3.

WO 2007/056124, WO 2006/017995, WO 2008/140750, and WO 2008/033564 disclose TRPV3 modulators, in particularly antagonists, for treatment of various diseases mediated TRPV3. WO 2006/065686 and WO 2007/042906 disclose benzopyran derivatives; WO 2009/084034, WO 2009/109987 and WO 2009/130560 applications disclose different scaffolds for TRPV3 modulators, particularly related to TRPV3 antagonist.

In efforts to discover better analgesics, there still exists a need for therapeutic treatment of diseases, conditions and/or disorders modulated by TRPV3.

SUMMARY OF THE INVENTION

In accordance with one aspect, the present patent application provides compounds of the formula (I) with TRPV3 antagonistic activity:

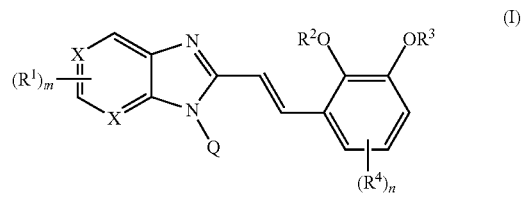

wherein, at each occurrence, X is independently selected from C or N, when X is N optionally oxidized to form N oxide;

at each occurrence, $R^1$ is independently selected from hydrogen, halogen, hydroxyl, nitro, cyano, substituted or unsubstituted alkyl, alkenyl, alkoxy, haloalkyl, haloalkoxy, cycloalkyl, cycloalkoxy, aryl, arylalkyl, heteroaryl, heteroarylalkyl, —S(O)$_p$R$^5$ (where p is 1 or 2), and —SO$_2$NR$^5$R$^6$;

'm' is an integer ranging from 1 to 4, both inclusive;

Q is hydrogen, substituted or unsubstituted alkyl, haloalkyl, aryl, arylalkyl, heteroaryl; wherein substituents, may be one or more and are independently selected from halogen, hydroxyl, nitro, cyano, amino, COOR$^a$, C(O)NR$^5$R$^6$, substituted or unsubstituted alkyl, alkoxy, haloalkyl, haloalkoxy, cycloalkyl, and cycloalkoxy;

$R^2$ and $R^3$, may be same or different, are independently selected from the group consisting of hydrogen, substituted or unsubstituted alkyl, haloalkyl, alkoxyalkyl, alkenyl, cycloalkyl, cycloalkylalkyl, aryl, arylalkyl, heteroaryl, heteroarylalkyl, heterocyclic group, and heterocyclylalkyl;

at each occurrence, $R^4$ is independently selected from hydrogen, halogen, hydroxyl, nitro, cyano, amino, —COOR$^a$, substituted or unsubstituted alkyl, alkenyl, alkoxy, haloalkyl, haloalkoxy, cycloalkyl, cycloalkoxy, aryl, arylalkyl, heteroaryl, heteroarylalkyl;

at each occurrence, $R^a$ is independently hydrogen or substituted or unsubstituted alkyl;

at each occurrence, $R^5$ and $R^6$, may be same or different, are independently selected from hydrogen, substituted or unsubstituted alkyl, haloalkyl, cycloalkyl, aryl and heteroaryl, cycloalkylalkyl, arylalkyl, and heteroarylalkyl; and 'n' is an integer ranging from 1 to 3, both inclusive;
or pharmaceutically acceptable salt thereof.

According to one embodiment, there is provided a compound of the formula (II):

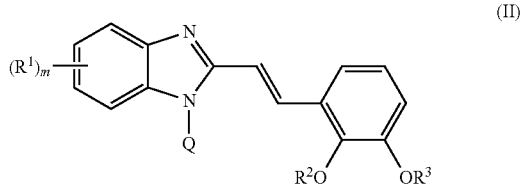

(II)

wherein, at each occurrence, $R^1$ is independently selected from hydrogen, halogen, hydroxyl, nitro, cyano, substituted or unsubstituted alkyl, alkenyl, alkoxy, haloalkyl, haloalkoxy, cycloalkyl, cycloalkoxy, aryl, arylalkyl, heteroaryl, heteroarylalkyl, —S(O)$_p$R$^5$ (where p is 1 or 2), and —SO$_2$NR$^5$R$^6$;

'm' is an integer ranging from 1 to 4, both inclusive;

Q is hydrogen, substituted or unsubstituted alkyl, haloalkyl, aryl, arylalkyl, heteroaryl; wherein substituents, may be one or more and are independently selected from halogen, hydroxyl, nitro, cyano, amino, COOR$^a$, C(O)NR$^5$R$^6$, substituted or unsubstituted alkyl, alkoxy, haloalkyl, haloalkoxy, cycloalkyl, and cycloalkoxy;

R$^a$ is hydrogen or substituted or unsubstituted alkyl;

R$^2$ and R$^3$, may be same or different, are independently selected from the group consisting of hydrogen, substituted or unsubstituted alkyl, haloalkyl, alkoxyalkyl, alkenyl, cycloalkyl, cycloalkylalkyl, aryl, arylalkyl, heteroaryl, heteroarylalkyl, heterocyclic group, and heterocyclylalkyl; and at each occurrence, R$^5$ and R$^6$, may be same or different, are independently selected from hydrogen, substituted or unsubstituted alkyl, haloalkyl, cycloalkyl, aryl and heteroaryl, cycloalkylalkyl, arylalkyl, and heteroarylalkyl;

or pharmaceutically acceptable salt thereof.

According to one embodiment, specifically provided are compounds of the formula (II) in which R$^1$ is halogen, (for example F, Cl or Br), alkyl (for example methyl), alkoxy (for example methoxy), haloalkyl (for example trifluoromethyl), or haloalkoxy (for example difluoromethoxy, trifluoromethoxy); and 'm' is 1, 2 or 3.

According to another embodiment, specifically provided are compounds of the formula (II) in which Q is substituted or unsubstituted aryl, preferably phenyl.

According to another embodiment, specifically provided are compounds of the formula (II) in which Q is substituted or unsubstituted arylalkyl, preferably benzyl.

According to another embodiment, specifically provided are compounds of the formula (II) in which Q is substituted or unsubstituted aryl (for example phenyl), arylalkyl (for example benzyl), heteroaryl, preferably pyridine, pyridazine, pyrimidine, thiophene, thiazole, benzothiazole. In this embodiment the substituent(s) on aryl, arylalkyl or heteroaryl may be one or more, and are independently selected from halogen, nitro, cyano, amino, —COOH, COOCH$_3$ COOC$_2$H$_5$, C(O)NH$_2$, alkyl, alkoxy, haloalkyl, and haloalkoxy.

According to another embodiment, specifically provided are compounds of the formula (II) in which R$^2$ is hydrogen, alkyl, haloalkyl, cycloalkyl, cycloalkylalkyl, aryl, arylalkyl.

According to another embodiment, specifically provided are compounds of the formula (II) in which R$^3$ is hydrogen, alkyl (for example methyl), or haloalkyl (for example difluoromethyl).

According to another embodiment, there is provided a compound of formula (III):

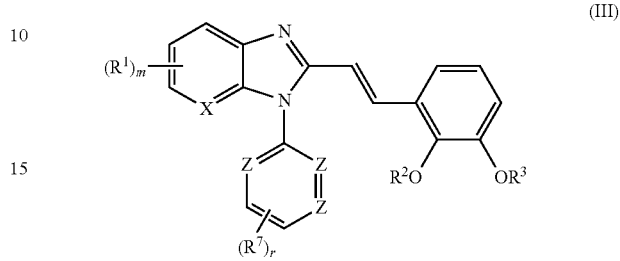

(III)

wherein, X is C or N, when X is N, optionally oxidized to form N oxide;

at each occurrence, Z is independently selected from C or N;

at each occurrence, R$^1$ is independently selected from hydrogen, halogen, hydroxyl, nitro, cyano, substituted or unsubstituted alkyl, alkenyl, alkoxy, haloalkyl, haloalkoxy, cycloalkyl, cycloalkoxy, aryl, arylalkyl, heteroaryl, heteroarylalkyl, —S(O)$_p$R$^5$ (where p is 1 or 2), and —SO$_2$NR$^5$R$^6$;

'm' is an integer ranging from 1 to 4, both inclusive;

at each occurrence, R$^7$ may be same or different, is independently selected from halogen, hydroxyl, nitro, cyano, amino, COOR$^a$, C(O)NR$^5$R$^6$, substituted or unsubstituted alkyl, alkoxy, haloalkyl, haloalkoxy, cycloalkyl, and cycloalkoxy;

R$^a$ is hydrogen or substituted or unsubstituted alkyl;

R$^2$ and R$^3$, may be same or different, are independently selected from the group consisting of hydrogen, substituted or unsubstituted alkyl, haloalkyl, alkoxyalkyl, alkenyl, cycloalkyl, cycloalkylalkyl, aryl, heteroaryl, heterocyclic group, arylalkyl, heteroarylalkyl, and heterocyclylalkyl;

at each occurrence, R$^5$ and R$^6$, may be same or different, are independently selected from hydrogen, substituted or unsubstituted alkyl, haloalkyl, cycloalkyl, cycloalkylalkyl, aryl, arylalkyl, heteroaryl, and heteroarylalkyl; and 'r' is an integer ranging from 1 to 5, both inclusive;

or pharmaceutically acceptable salt thereof.

According to one embodiment, specifically provided are compounds of the formula (III) in which R$^1$ is halogen, (for example F, Cl or Br), and 'm' is 1, 2.

According to another embodiment, specifically provided are compounds of the formula (III) in which Q is substituted or unsubstituted aryl, preferably phenyl.

According to another embodiment, specifically provided are compounds of the formula (III) in which Q is substituted or unsubstituted arylalkyl, preferably benzyl.

According to another embodiment, specifically provided are compounds of the formula (III) in which Q is substituted or unsubstituted aryl (for example phenyl), arylalkyl (for example benzyl), heteroaryl, preferably pyridine, pyridazine, pyrimidine, thiophene, thiazole, benzothiazole. In this embodiment the substituent(s) on aryl, arylalkyl or heteroaryl may be one or more, and are independently selected from halogen, nitro, cyano, amino, —COOH, COOCH$_3$ COOC$_2$H$_5$, C(O)NH$_2$, alkyl, alkoxy, haloalkyl, and haloalkoxy.

According to another embodiment, specifically provided are compounds of the formula (III) in which $R^2$ is hydrogen, alkyl, haloalkyl, cycloalkyl, cycloalkylalkyl, aryl, arylalkyl.

According to another embodiment, specifically provided are compounds of the formula (III) in which $R^3$ is hydrogen, alkyl (for example methyl), or haloalkyl (for example difluoromethyl).

It should be understood that the formulas (I), (II), and (III) structurally encompasses all geometrical isomers, stereoisomers, enantiomers and diastereomers, and pharmaceutically acceptable salts that may be contemplated from the chemical structure of the genera described herein.

According to another embodiment, specifically provided are compounds of Formula I, Formula II, or Formula III, and salts thereof, that inhibit a TRPV3 function with an $IC_{50}$ value of less than 10,000 nM, or even less than 1000, 500, 250 or 100 nM. In other embodiments, specifically provided are compounds of Formula I, Formula II or Formula III or a salt thereof, that inhibits a TRPV3 function with an $IC_{50}$ value of less than 100 nM, preferably as measured via the methods described herein.

In accordance with another aspect, the present patent application provides a pharmaceutical composition that includes at least one compound of described herein and at least one pharmaceutically acceptable excipient (such as a carrier or diluent). Preferably, the pharmaceutical composition comprises a therapeutically effective amount of at least one compound described herein. The compound of the present application may be associated with a pharmaceutically acceptable excipient (such as a carrier or a diluent) or be diluted by a carrier, or enclosed within a carrier which may be in the form of a capsule, sachet, paper or other container.

The compounds and pharmaceutical compositions described herein are useful in the treatment of diseases, conditions and/or disorders modulated by TRPV3 receptors.

In accordance with another aspect, the present patent application further provides a method of treating a disease, condition and/or disorder modulated by TRPV3 receptors in a subject in need thereof by administering to the subject one or more compounds described herein in the amount effective to cause inhibition of such receptor.

Also provided herein are processes for preparing compounds described herein.

DETAILED DESCRIPTION OF THE INVENTION

The invention is defined by the claims and not limited by the description provided herein below. The terms used in the appended claims are defined herein in this glossary section, with the proviso that the claim terms may be used in a different manner if so defined by express recitation.

The terms "halogen" or "halo" means fluorine, chlorine, bromine, or iodine

The term "alkyl" refers to a hydrocarbon chain radical that includes solely carbon and hydrogen atoms in the backbone, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, and 1,1-dimethylethyl (t-butyl). The term "$C_{1-6}$ alkyl" refers to an alkyl chain having 1 to 6 carbon atoms. Unless set forth or recited to the contrary, all alkyl groups described or claimed herein may be straight chain or branched, substituted or unsubstituted.

The term "alkenyl" refers to a hydrocarbon chain containing from 2 to 10 carbon atoms and including at least one carbon-carbon double bond. Non-limiting examples of alkenyl groups include ethenyl, 1-propenyl, 2-propenyl (allyl), iso-propenyl, 2-methyl-1-propenyl, 1-butenyl, and 2-butenyl. Unless set forth or recited to the contrary, all alkenyl groups described or claimed herein may be straight chain or branched, substituted or unsubstituted.

The term "alkynyl" refers to a hydrocarbyl radical having at least one carbon-carbon triple bond, and having 2 to about 12 carbon atoms (with radicals having 2 to about 10 carbon atoms being preferred). Non-limiting examples of alkynyl groups include ethynyl, propynyl, and butynyl. Unless set forth or recited to the contrary, all alkynyl groups described or claimed herein may be straight chain or branched, substituted or unsubstituted.

The term "alkoxy" denotes an alkyl group attached via an oxygen linkage to the rest of the molecule. Representative examples of such groups are —$OCH_3$ and —$OC_2H_5$. Unless set forth or recited to the contrary, all alkoxy groups described or claimed herein may be straight chain or branched, substituted or unsubstituted.

The term "cycloalkyl" denotes a non-aromatic mono or multicyclic ring system of 3 to about 12 carbon atoms, such as cyclopropyl, cyclobutyl, cyclopentyl, and cyclohexyl. Examples of multicyclic cycloalkyl groups include, but are not limited to, perhydronapththyl, adamantyl and norbornyl groups, bridged cyclic groups or sprirobicyclic groups, e.g., sprio(4,4)non-2-yl. Unless set forth or recited to the contrary, all cycloalkyl groups described or claimed herein may be substituted or unsubstituted.

The term "cycloalkylalkyl" refers to a cyclic ring-containing radical having 3 to about 8 carbon atoms directly attached to an alkyl group. The cycloalkylalkyl group may be attached to the main structure at any carbon atom in the alkyl group that results in the creation of a stable structure. Non-limiting examples of such groups include cyclopropylmethyl, cyclobutylethyl, and cyclopentylethyl. Unless set forth or recited to the contrary, all cycloalkylalkyl groups described or claimed herein may be substituted or unsubstituted.

The term "cycloalkenyl" refers to a cyclic ring-containing radical having 3 to about 8 carbon atoms with at least one carbon-carbon double bond, such as cyclopropenyl, cyclobutenyl, and cyclopentenyl. Unless set forth or recited to the contrary, all cycloalkenyl groups described or claimed herein may be substituted or unsubstituted.

The term "aryl" refers to an aromatic radical having 6 to 14 carbon atoms, including monocyclic, bicyclic and tricyclic aromatic systems, such as phenyl, naphthyl, tetrahydronapthyl, indanyl, and biphenyl. Unless set forth or recited to the contrary, all aryl groups described or claimed herein may be substituted or unsubstituted.

The term "arylalkyl" refers to an aryl group as defined above directly bonded to an alkyl group as defined above, e.g., —$CH_2C_6H_5$ and —$C_2H_4C_6H_5$. Unless set forth or recited to the contrary, all arylalkyl groups described or claimed herein may be substituted or unsubstituted.

The term "heterocyclic ring" or "heterocyclyl" unless otherwise specified refers to substituted or unsubstituted non-aromatic 3 to 15 membered ring radical which consists of carbon atoms and from one to five heteroatoms selected from nitrogen, phosphorus, oxygen and sulfur. The heterocyclic ring radical may be a mono-, bi- or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; also, unless otherwise constrained by the definition the heterocyclic ring or heterocyclyl may optionally contain one or more olefinic bond(s). Examples of such heterocyclic ring radicals include, but are not limited to azepinyl, azetidinyl, benzodioxolyl, benzodioxanyl, chromanyl, dioxolanyl, dioxaphospholanyl, decahydroisoquinolyl, indanyl, indolinyl, isoindolinyl, isochromanyl, isothiazolidinyl, isoxazolidinyl, morpholinyl, oxazolinyl, oxazolidinyl, oxadiazolyl, 2-oxopiperazinyl, 2-oxopiperidinyl, 2-oxopyrrolidinyl, 2-oxoazepinyl, octahydroindolyl, octahydroisoindolyl, perhydroazepinyl, piperazinyl, 4-piperidonyl, pyrrolidinyl, piperidinyl, phenothiazinyl, phenoxazinyl, quinuclidinyl, tetrahydroisquinolyl, tetrahydrofuryl, tetrahydropyranyl, thiazolinyl, thiazolidinyl, thiamorpholinyl, thiamorpholinyl sulfoxide and thiamorpholinyl sulfone. The heterocyclic ring radical may be attached to the main structure at any heteroatom or carbon atom that results in the creation of a stable structure. Unless set forth or recited to the contrary, all heterocyclyl groups described or claimed herein may be substituted or unsubstituted.

The term "heterocyclylalkyl" refers to a heterocyclic ring radical directly bonded to an alkyl group. The heterocyclylalkyl radical may be attached to the main structure at any carbon atom in the alkyl group that results in the creation of a stable structure. Unless set forth or recited to the contrary, all heterocyclylalkyl groups described or claimed herein may be substituted or unsubstituted.

The term "heteroaryl" unless otherwise specified refers to substituted or unsubstituted 5 to 14 membered aromatic heterocyclic ring radical with one or more heteroatom(s) independently selected from N, O or S. The heteroaryl may be a mono-, bi- or tricyclic ring system. The heteroaryl ring radical may be attached to the main structure at any heteroatom or carbon atom that results in the creation of a stable structure. Examples of such heteroaryl ring radicals include, but are not limited to oxazolyl, isoxazolyl, imidazolyl, furyl, indolyl, isoindolyl, pyrrolyl, triazolyl, triazinyl, tetrazoyl, thienyl, thiazolyl, isothiazolyl, pyridyl, pyrimidinyl, pyrazinyl, pyridazinyl, benzofuranyl, benzothiazolyl, benzoxazolyl, benzimidazolyl, benzothienyl, benzopyranyl, carbazolyl, quinolinyl, isoquinolinyl, quinazolinyl, cinnolinyl, naphthyridinyl, pteridinyl, purinyl, quinoxalinyl, quinolyl, isoquinolyl, thiadiazolyl, indolizinyl, acridinyl, phenazinyl and phthalazinyl. Unless set forth or recited to the contrary, all heteroaryl groups described or claimed herein may be substituted or unsubstituted.

The term "heteroarylalkyl" refers to a heteroaryl ring radical directly bonded to an alkyl group. The heteroarylalkyl radical may be attached to the main structure at any carbon atom in the alkyl group that results in the creation of a stable structure. Unless set forth or recited to the contrary, all heteroarylalkyl groups described or claimed herein may be substituted or unsubstituted.

Unless otherwise specified, the term "substituted" as used herein refers to a group or moiety having one or more of the substituents attached to the structural skeleton of the group or moiety, including, but not limited to such substituents as hydroxy, halogen, carboxyl, cyano, nitro, oxo (=O), thio (=S), substituted or unsubstituted alkyl, substituted or unsubstituted haloalkyl, substituted or unsubstituted alkoxy, substituted or unsubstituted haloalkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted amino, substituted or unsubstituted aryl, substituted or unsubstituted heteroaryl, substituted or unsubstituted heterocyclylalkyl ring, substituted or unsubstituted heteroarylalkyl, substituted or unsubstituted heterocyclic ring, substituted or unsubstituted guanidine, —COOR$^x$, —C(O)R$^x$, —C(S)R$^x$, —C(O)NR$^x$R$^y$, —C(O)ONR$^x$R$^y$, —NR$^x$CONR$^y$R$^z$, —N(R$^x$)SOR$^y$, —N(R$^x$)SO$_2$R$^y$, —(=N—N(R$^x$)R$^y$), —NR$^x$C(O)OR$^y$, —NR$^x$R$^y$, —NR$^x$C(O)R$^y$, —NR$^x$C(S)R$^y$, —NR$^x$C(S)NR$^y$R$^z$, —SONR$^x$R$^y$, —SO$_2$NR$^x$R$^y$, —OR$^x$, —OR$^x$C(O)NR$^y$R$^z$, —OR$^x$C(O)OR$^y$, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O)NR$^y$R$^z$, —R$^x$C(O)R$^y$, —R$^x$OC(O)R$^y$, —SR$^x$, —SOR$^x$, —SO$_2$R$^x$, and —ONO$_2$, wherein R$^x$, R$^y$ and R$^z$ are independently selected from hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocyclylalkyl ring, substituted or unsubstituted heteroarylalkyl, or substituted or unsubstituted heterocyclic ring. The substituents in the aforementioned "substituted" groups cannot be further substituted. For example, when the substituent on "substituted alkyl" is "substituted aryl", the substituent on "substituted aryl" cannot be "substituted alkenyl".

The term "treating" or "treatment" of a state, disorder or condition includes: (a) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition; (b) inhibiting the state, disorder or condition, i.e., arresting or reducing the development of the disease or at least one clinical or subclinical symptom thereof; or (c) relieving the disease, i.e., causing regression of the state, disorder or condition or at least one of its clinical or subclinical symptoms.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a state, disorder or condition, is sufficient to cause the effect in the subject which is the purpose of the administration. The "therapeutically effective amount" will vary depending on the compound, the disease and its severity and the age, weight, physical condition and responsiveness of the subject to be treated.

The compound described in the present patent application may form salts. Non-limiting examples of pharmaceutically acceptable salts forming part of this patent application include salts derived from inorganic bases, salts of organic bases, salts of chiral bases, salts of natural amino acids and salts of non-natural amino acids. With respect to the overall compounds described by the Formula (I), the present patent application extends to these stereoisomeric forms and to mixtures thereof. To the extent prior art teaches synthesis or separation of particular stereoisomers, the different stereoisomeric forms of the present patent application may be separated from one another by the method known in the art, or a given isomer may be obtained by stereospecific or asymmetric synthesis. Tautomeric forms and mixtures of compounds described herein are also contemplated.

Pharmaceutical Compositions

The pharmaceutical composition provided in the present invention includes at least one compound described herein and at least one pharmaceutically acceptable excipient (such as a carrier or diluent). Preferably, the contemplated pharmaceutical compositions include the compound(s) described herein in an amount sufficient to inhibit TRPV3 receptor in a subject.

The subjects contemplated include, for example, a living cell and a mammal, including human. The compound of the present invention may be associated with a pharmaceutically acceptable excipient (such as a carrier or a diluent) or be diluted by a carrier, or enclosed within a carrier which can be in the form of a capsule, sachet, paper or other container.

Examples of suitable carriers include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicylic acid, fatty acids, fatty acid amines, fatty acid monoglycerides and diglycerides, pentaerythritol fatty acid esters, polyoxyethylene, hydroxymethylcellulose and polyvinylpyrrolidone.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be formulated so as to provide quick, sustained, or delayed release of the active ingredient after administration to the subject by employing procedures known in the art.

The pharmaceutical compositions described herein may be prepared by conventional techniques known in the art. For example, the active compound can be mixed with a carrier, or diluted by a carrier, or enclosed within a carrier, which may be in the form of an ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container, for example, in a sachet.

The pharmaceutical compositions may be in conventional forms, for example, capsules, tablets, aerosols, solutions, suspensions or products for topical application.

The route of administration may be any route which effectively transports the active compound of the invention to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment).

Solid oral formulations include, but are not limited to, tablets, capsules (soft or hard gelatin), dragees (containing the active ingredient in powder or pellet form), troches and lozenges. Tablets, dragees, or capsules having talc and/or a carbohydrate carrier or binder or the like are particularly suitable for oral application. Liquid formulations include, but are not limited to, syrups, emulsions, soft gelatin and sterile injectable liquids, such as aqueous or non-aqueous liquid suspensions or solutions. For parenteral application, particularly suitable are injectable solutions or suspensions formulation.

Liquid formulations include, but are not limited to, syrups, emulsions, soft gelatin and sterile injectable liquids, such as aqueous or non-aqueous liquid suspensions or solutions.

For parenteral application, particularly suitable are injectable solutions or suspensions, preferably aqueous solutions with the active compound dissolved in polyhydroxylated castor oil.

Suitable doses of the compounds for use in treating the diseases and disorders described herein can be determined by those skilled in the relevant art. Therapeutic doses are generally identified through a dose ranging study in humans based on preliminary evidence derived from the animal studies. Doses must be sufficient to result in a desired therapeutic benefit without causing unwanted side effects. For example, the daily dosage of the TRPV3 modulator can range from about 0.1 to about 30.0 mg/kg. Mode of administration, dosage forms, suitable pharmaceutical excipients, diluents or carriers can also be well used and adjusted by those skilled in the art. All changes and modifications are envisioned within the scope of the present invention.

Methods of Treatment

The present invention provides compounds and pharmaceutical formulations thereof that are useful in the treatment of diseases, conditions and/or disorders modulated by TRPV3. The present patent application further provides a method of treating a disease, condition and/or disorder modulated by TRPV3 in a subject in need thereof by administering to the subject a therapeutically effective amount of a compound or a pharmaceutical composition of the present invention.

Diseases, conditions, and/or disorders that are modulated by TRPV3 are believed to include, but are not limited to pain, nociceptive pain, dental pain, cardiac pain arising from an ischemic myocardium, pain due to migraine, acute pain, chronic pain, neuropathic pain, post-operative pain, pain due to neuralgia (e.g., post-herpetic neuralgia or trigeminal neuralgia), pain due to diabetic neuropathy, dental pain and cancer pain, inflammatory pain conditions (e.g. arthritis and osteoarthritis), arthralgia, neuropathies, neurodegeneration, retinopathy, neurotic skin disorder, stroke, urinary bladder hypersensitiveness, urinary incontinence, vulvodynia, gastrointestinal disorders such as irritable bowel syndrome, gastro-esophageal reflux disease, enteritis, ileitis, stomach-duodenal ulcer, inflammatory bowel disease, Crohn's disease, celiac disease, an inflammatory disease such as pancreatitis, a respiratory disorder such as allergic and non-allergic rhinitis, asthma or chronic obstructive pulmonary disease, irritation of skin, eye or mucous membrane, dermatitis, pruritic conditions such as uremic pruritus, fervescence, muscle spasms, emesis, dyskinesias, depression, Huntington's disease, memory deficits, restricted brain function, amyotrophic lateral sclerosis (ALS), dementia, arthritis, osteoarthritis, rheumatoid arthritis, diabetes, obesity, urticaria, actinic keratosis, keratocanthoma, alopecia, Meniere's disease, tinnitus, hyperacusis, anxiety disorders and benign prostate hyperplasia. Additional diseases, conditions and/or disorders modulated by TRPV3 is illustrated, for example in WO2007/056124; Wissenbach, U. et al, *Biology of the cell* (2004), 96, 47-54; Nilius, B. et al., *Physiol Rev* (2007), 87, 165-217; Okuhara, D. Y. et al, *Expert Opinion on Therapeutic Targets* (2007), 11, 391-401; Hu, H. Z. et al, *Journal of Cellular Physiology*, (2006), 208, 201-212 and references cited therein, all of which are incorporated herein by reference in their entirety and for the purpose stated.

General Methods of Preparation

The compounds described herein may be prepared by techniques known in the art. In addition, the compounds described herein may be prepared by following the reaction sequence as depicted in Schemes 1 to 3. Further, in the following schemes, where specific bases, acids, reagents, solvents, coupling agents, etc. are mentioned, it is understood that other bases, using a reducing agent such as iron and acetic acid to give intermediate of the formula (4). Intermediate (4) is cyclised to the benzimidazole derivative (5) by a dehydration reaction under strongly acidic reaction conditions. Alternatively, compound of formula (5) can be prepared by reductive cyclization of compound of formula (3) using reducing agents such as Raney nickel or iron and acetic acid. Copper (I) assisted coupling of (5) with an intermediate of the formula (6), where L is leaving group such as halogen, gives compounds of the present invention represented by the general formula (I). Compounds of the general formula (I) where Q is a benzyl group can be prepared by direct alkylation of intermediate (5) with a benzyl halide in the presence of a strong base such as cesium carbonate. In some cases, the compound of formula (I) (when $R^2$ is alkyl) can be selectively dealkylated in presence of Lewis acid such as boron tribromide in dichloromethane or HBr in acetic acid to give compound of general formula (Ia).

Scheme 1

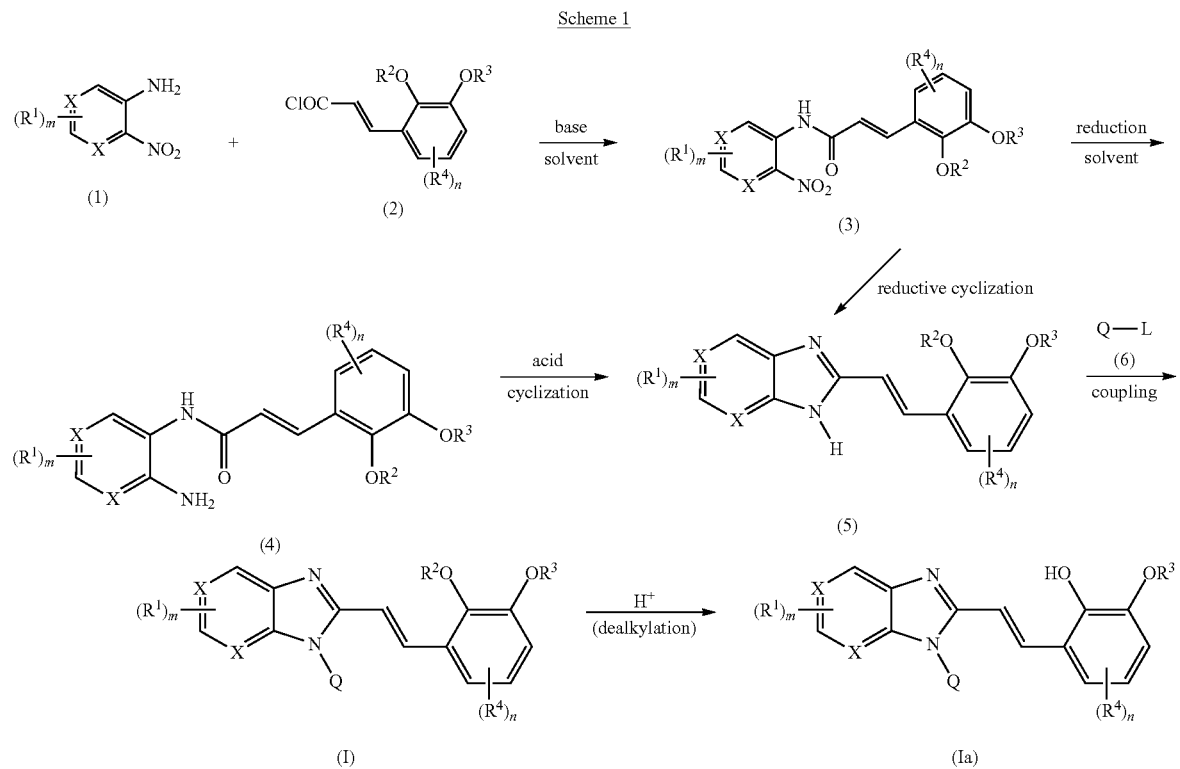

acids, reagents, solvents, coupling agents etc. known in the art may also be used and are therefore included within the scope of the present invention. Variations in reaction conditions, for example, temperature and/or duration of the reaction, which may be used as known in the art are also within the scope of the present invention. All the isomers of the compounds in described in these schemes, unless otherwise specified, are also encompassed within the scope of this invention.

The compound of the present invention represented by the general formula (I), where $R^1$, $R^2$, $R^3$, $R^4$, Q, X, m, and n are as described previously, can be prepared as described in Scheme 1. Thus, intermediate of the formula (1) (e.g., 2-nitroaniline, 2-amino-3-nitropyridine, 4-amino-3-nitropyridine) is coupled with 2,3-dialkoxycinnamyl chloride of the formula (2) in the presence of a suitable base to give amide of the formula (3). The nitro group in intermediate (3) is reduced The compounds of general formula (I), where $R^1$, $R^2$, $R^3$, $R^4$, Q, y X, m, and n are as described previously, can be also be prepared by an alternative approach as shown in Scheme 2. In this approach, intermediate of formula (1a) is coupled with an intermediate of the formula (6) prior to the cyclization step. Thus, intermediate (1a) is treated with intermediate (6) where L is preferably Cl, Br or I in the presence of a suitable base to give the coupled product (7). The nitro group of intermediate (7) is reduced using reducing agents such as iron and acetic acid to obtain intermediate (8) which is coupled with 2,3-dialkoxycinnamyl chloride of the formula (2) in the presence of a suitable base to give amide of the formula (9). Cyclization of intermediate (9) in presence of a suitable acid such as acetic acid gives compounds of the present invention represented by the formula (I).

Scheme 2

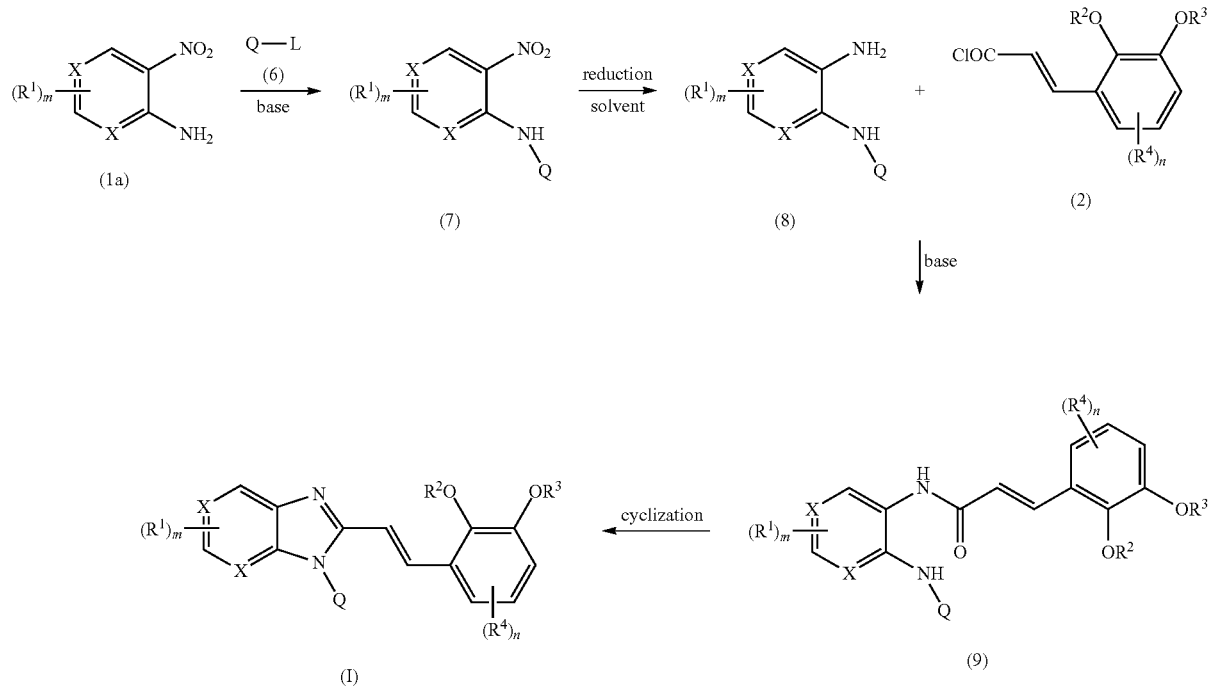

The compounds of general formula (I), where $R^1$, $R^2$, $R^3$, $R^4$, Q, X, m, and n are as described previously can also be prepared as shown in Scheme 3. Thus, intermediate of the formula (10) where L is a halogen, preferably Cl or Br on reaction with an amine of the formula (11) in the presence of a suitable base furnishes compound of the formula (7). The nitro group of the intermediate (7) is reduced using reducing agents such as iron and acetic acid to obtain intermediate (8) which is coupled with 2,3-dialkoxycinnamyl chloride of the formula (2) in the presence of a suitable base to give amide of the formula (9). Cyclization of intermediate (9) in presence of a suitable acid such as acetic acid gives compound of the present invention represented by the formula (I).

Scheme 3

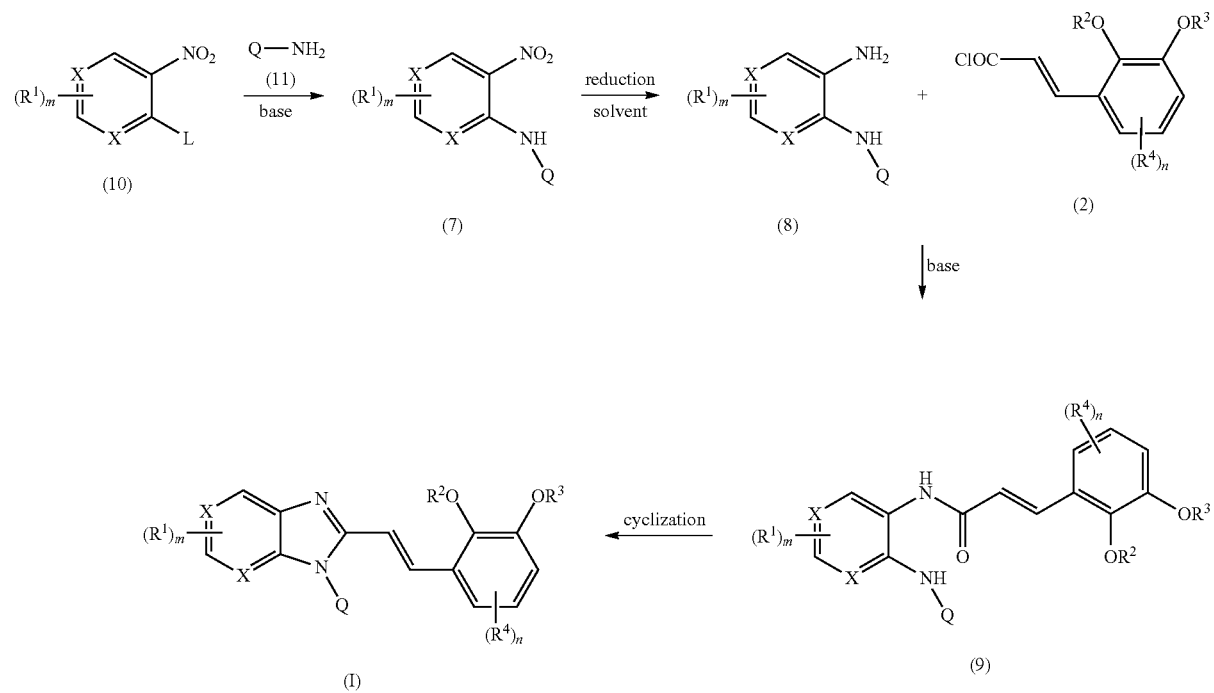

The starting raw materials and reagents required for the syntheses of intermediates and compounds of invention are commercially available (e.g. Sigma-Aldrich) or can be prepared according to methods known to one skilled in the art or by methods available in the literature. In general, the compounds of the present invention are prepared as follows:

EXPERIMENTAL

Unless otherwise stated, work-up implies the following operations: distribution of the reaction mixture between the organic and aqueous phase, separation of layers, drying the organic layer over sodium sulfate, filtration and evaporation of the organic solvent. Purification, unless otherwise mentioned, implies purification by silica gel chromatographic techniques, generally using ethyl acetate/petroleum ether mixture of a suitable polarity as the mobile phase. The following abbreviations are used in the text: DMSO-d$_6$: hexadeuterodimethyl sulfoxide; DMF: N,N-dimethylformamide, J: coupling constant in units of Hz; RT: room temperature (22-26° C.). aq.: aqueous AcOEt: ethyl acetate; equiv.: equivalents.

Preparation of Intermediates

Intermediate 1

2-[(E)-2-(2-Isopropoxy-3-methoxyphenyl)vinyl]-1H-benzimidazole

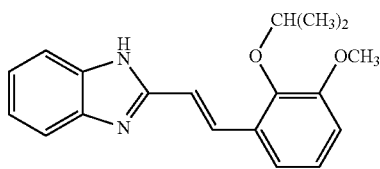 [SMILES: COc1cccc(/C=C/c2nc3ccccc3[nH]2)c1OC(C)C]

Step 1: (2E)-3-(2-isopropoxy-3-methoxyphenyl)-N-(2-nitrophenyl)acrylamide: To a well stirred solution of (2E)-3-(2-isopropoxy-3-methoxyphenyl)acrylic acid (5.0 g, 21.163 mmol) in dichloromethane (DCM) (50 ml), oxalyl chloride (4.03 g, 31.752 mmol) was added drop wise at 0° C. and the reaction mixture was stirred for 1 h at room temperature. Excess of oxalyl chloride and solvent was evaporated under vacuum. The residue obtained was directly used for the next step.

Step 2: To a well stirred solution of above acid chloride (5.4 g, 21.201 mmol) at 0° C., 2-nitro aniline (2.93 g, 21.213 mmol) in pyridine (50 ml) was added drop wise and the reaction mixture was stirred overnight at room temperature. After completion of the reaction, the reaction mixture was poured into ice cold solution of 10% hydrochloric acid (100 ml). The aqueous layer was then extracted with ethyl acetate (2×100 ml) and the combined organic layers were washed with water (2×20 ml), brine (100 ml) and dried over (Na$_2$SO$_4$). The crude product obtained after evaporation of the solvent under reduced pressure was purified by silica gel column chromatography using 1% ethyl acetate in petroleum ether to give 4.83 g of the product; $^1$H NMR (300 MHz, CDCl$_3$) δ 1.33 (d, J=6.3 Hz, 6H) 3.85 (s, 3H), 4.52 (br s, 1H), 6.63 (d, J=15.6 Hz, 1H), 6.92 (d, J=9.0 Hz, 1H), 7.04 (t, J=7.8 Hz, 1H), 7.13-7.22 (m, 2H), 7.65 (t, J=7.5 Hz, 1H), 8.13 (d, J=15.9 Hz, 1H), 8.22 (d, J=6.6 Hz, 1H), 8.93 (d, J=7.5 Hz, 1H), 10.64 (br s, 1H).

Step 3: (2E)-N-(2-aminophenyl)-3-(2-isopropoxy-3-methoxyphenyl)acrylamide: To a well stirred solution of Step 2 intermediate (4.0 g, 11.224 mmol) in ethanol was added aqueous solution of ammonium chloride (6.0 g, 112.17 mmol). The reaction mixture was refluxed for 20 min, then iron powder (1.88 g, 33.667 mmol) was added portion wise over the period of 30 min and it was further refluxed for 2 h. The reaction mixture was cooled to room temperature, diluted with ethyl acetate (100 ml) and filtered through celite bed. The ethyl acetate layer was then washed with water (2×50 ml), brine (50 ml), dried (Na$_2$SO$_4$), filtered and concentrated to give 3.5 g of the product as a white solid; $^1$H NMR (300 MHz, CDCl$_3$) δ 1.29 (d, J=6.9 Hz, 6H) 3.83 (s, 3H), 4.45 (br s, 1H), 5.08 (br s, 2H), 6.60 (d, J=15.6 Hz, 1H), 6.80 (d, J=7.8 Hz, 2H), 6.88 (d, J=7.8 Hz, 1H), 7.00 (d, J=8.1 Hz, 2H), 7.12 (d, J=7.8 Hz, 1H), 7.59 (s, 1H), 8.07 (d, J=15.6 Hz, 1H), 9.25 (s, 1H);

Step 4: 2-[(E)-2-(2-isopropoxy-3-methoxyphenyl)vinyl]-1H-benzimidazole: The above Step 3 intermediate (3.4 g, 10.147 mmol) was dissolved in glacial acetic acid (34 ml) and the reaction mixture was refluxed overnight. The excess of acetic acid was evaporated under reduced pressure and the reaction mixture was made slightly basic using aqueous sodium carbonate solution. The reaction mixture was then extracted with ethyl acetate (100 ml), washed with water (2×50 ml), brine (50 ml), dried over Na$_2$SO$_4$. The crude product obtained after evaporation of the solvent under reduced pressure was purified by silica gel column chromatography using 10% ethyl acetate in petroleum ether to give 2.84 g of the product as an off-white solid; IR (KBr) 2933, 1577, 1421, 1267, 1108, 745 cm$^{-1}$; $^1$H NMR (300 MHz, CDCl$_3$) δ 1.22 (d, J=6.6 Hz, 6H) 3.79 (s, 3H), 4.44 (br s, 1H), 6.82 (d, J=8.4 Hz, 1H), 6.97 (t, J=8.4 Hz, 1H), 7.13 (d, J=7.8 Hz, 1H), 7.17-7.23 (m, 3H), 7.54-7.62 (m, 3H), 7.86 (d, J=16.8 Hz, 1H); ESI-MS (m/z) 309.22 (M+H)$^+$.

The Intermediates 2 to 31 were prepared by following the procedure described in Intermediate 1 by using appropriate 2-nitroaniline and cinnamoyl chloride as described in synthetic Scheme 1. The structural details and characterization data are given in Table 1.

TABLE 1

Structure and $^1$H NMR data of Intermediates 2 to 31

| Intermediate | Molecular Structure | $^1$H NMR data (300 MHz) |
| --- | --- | --- |
| Intermediate 2 | 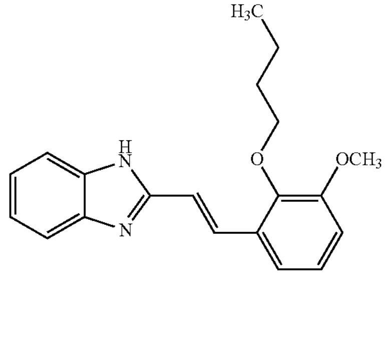 [SMILES: CCCCOc1c(/C=C/c2nc3ccccc3[nH]2)cccc1OC] | (CDCl$_3$) δ 0.90 (t, J = 7.8 Hz, 3 H), 1.38-1.45 (s, 2 H), 1.65-1.75 (m, 2 H), 3.82 (s, 3 H), 3.93 (d, J = 6.9 Hz, 2 H), 6.83 (d, J = 8.4 Hz, 1 H), 6.98 (t, J = 7.8 Hz, 1 H), 7.12 (d, J = 7.8 Hz, 1 H), 7.19-7.24 (m, 4 H), 7.55-7.61 (m, 2 H), 7.84 (d, J = 17.1 Hz, 1 H). |

TABLE 1-continued

Structure and $^1$H NMR data of Intermediates 2 to 31

| Intermediate | Molecular Structure | $^1$H NMR data (300 MHz) |
| --- | --- | --- |
| Intermediate 3 | 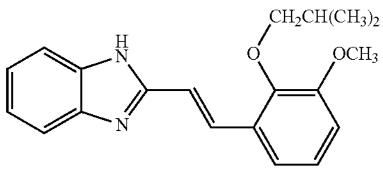 | (DMSO-$d_6$) δ 0.99 (d, J = 6.6 Hz, 6 H), 1.96-2.14 (m, 1 H), 3.69 (d, J = 6.3 Hz, 2 H), 3.79 (s, 3 H), 7.03 (t, J = 6.6 Hz, 1 H), 7.10 (d, J = 8.4 Hz, 1 H), 7.13-7.19 (m, 3 H), 7.29 (d, J = 7.2 Hz, 1 H), 7.49-7.55 (m, 2 H), 7.86 (d, J = 16.5 Hz, 1 H). |
| Intermediate 4 | 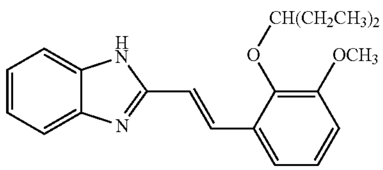 | (DMSO-$d_6$) δ 0.91 (t, J = 7.5 Hz, 6 H), 1.56-1.67 (m, 4 H), 3.80 (s, 3 H), 4.15 (t, J = 6.0 Hz, 1 H), 6.99-7.06 (m, 2 H), 7.09-7.16 (m, 3 H), 7.30 (d, J = 6.6 Hz, 1 H), 7.44 (d, J = 6.9 Hz, 1 H), 7.56 (d, J = 6.9 Hz, 1 H), 7.88 (d, J = 16.5 Hz, 1 H). |
| Intermediate 5 | 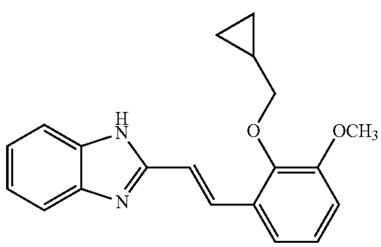 [SMILES: COc1cccc(/C=C/c2nc3ccccc3[nH]2)c1OCC1CC1] | (CDCl$_3$) δ 0.20-0.26 (m, 2 H), 0.50-0.56 (m, 2 H), 0.88 (br s, 1 H), 3.84 (s, 5 H), 6.85 (d, J = 7.2 Hz, 1 H), 7.03 (t, J = 7.2 Hz, 1 H), 7.17-7.28 (m, 4 H), 7.55-7.65 (m, 2 H), 7.87 (d, J = 17.4 Hz, 1 H). |
| Intermediate 6 | 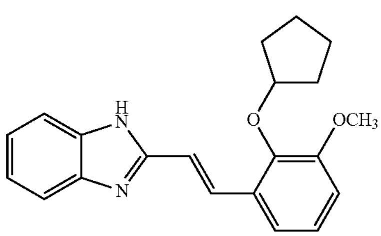 [SMILES: COc1cccc(/C=C/c2nc3ccccc3[nH]2)c1OC1CCCC1] | (CDCl$_3$) δ 1.55-1.65 (m, 4 H), 1.75-1.84 (m, 4 H), 3.82 (s, 3 H), 4.84 (br s, 1 H), 5.37 (br s, 1 H), 6.83 (d, J = 8.4 Hz, 1 H), 6.98 (t, J = 8.1 Hz, 1 H), 7.09-7.20 (m, 4 H), 7.50-7.60 (m, 2 H), 7.76 (d, J = 16.5 Hz, 1 H); APCI-MS (m/z) 335.59 (M + H)$^+$. |
| Intermediate 7 | 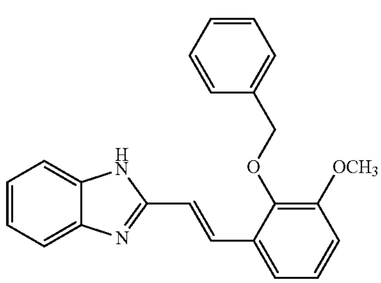 [SMILES: COc1cccc(/C=C/c2nc3ccccc3[nH]2)c1OCc1ccccc1] | (CDCl$_3$) δ 3.85 (s, 3 H), 4.96 (s, 2 H), 6.87 (d, J = 7.8 Hz, 1 H), 7.02 (t, J = 8.4 Hz, 1 H), 7.07 (s, 1 H), 7.12 (d, J = 6.0 Hz, 1 H), 7.17-7.23 (m, 3 H), 7.26-7.31 (m, 2 H), 7.36 (d, J = 4.8 Hz, 2 H), 7.50-7.56 (m, 3 H), 8.26 (br s, 1 H). |
| Intermediate 8 | 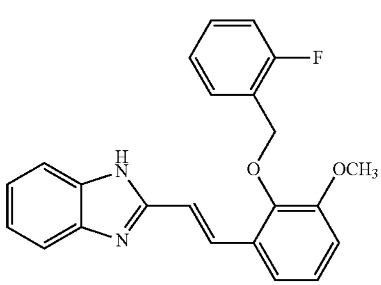 [SMILES: COc1cccc(/C=C/c2nc3ccccc3[nH]2)c1OCc1ccccc1F] | (CDCl$_3$) δ 3.88 (s, 3 H), 5.08 (s, 2 H), 6.87 (d, J = 7.8 Hz, 1 H), 6.95-7.02 (m, 1 H), 7.06 (d, J = 8.1 Hz, 2 H), 7.14 (s, 1 H), 7.20-7.30 (m, 4 H), 7.39 (t, J = 7.2 Hz, 1 H), 7.50-7.60 (m, 2 H), 7.65 (s, 1 H). |

TABLE 1-continued

Structure and ¹H NMR data of Intermediates 2 to 31

| Intermediate | Molecular Structure | ¹H NMR data (300 MHz) |
| --- | --- | --- |
| Intermediate 9 | 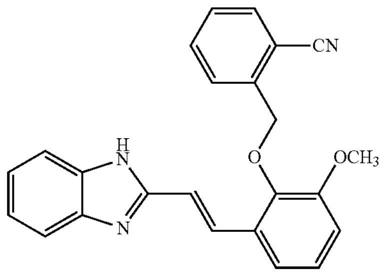 | (DMSO-d$_6$) δ 3.81 (s, 3 H), 5.23 (s, 2 H), 7.07 (d, J = 7.8 Hz, 1 H), 7.12-7.18 (m, 3 H), 7.34 (d, J = 6.9 Hz, 1 H), 7.50-7.56 (m, 3 H), 7.69 (t, J = 7.2 Hz, 1 H), 7.81-7.87 (s, 3 H). |
| Intermediate 10 | 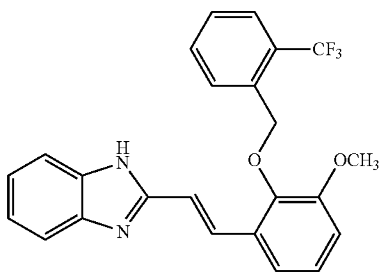 [SMILES: COc1cccc(/C=C/c2nc3ccccc3[nH]2)c1OCc1ccccc1C#N] | (DMSO-d$_6$) δ 3.81 (s, 3 H), 5.17 (s, 2 H), 7.09-7.19 (m, 5 H), 7.37 (d, J = 7.8 Hz, 1 H), 7.52-7.59 (m, 3 H), 7.74 (d, J = 6.3 Hz, 2 H), 7.88 (d, J = 16.5 Hz, 1 H), 8.01 (d, J = 7.8 Hz, 1 H). |
| Intermediate 11 | 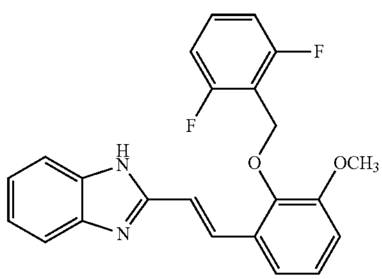 [SMILES: COc1cccc(/C=C/c2nc3ccccc3[nH]2)c1OCc1c(F)cccc1F] | (DMSO-d$_6$) δ 3.80 (s, 3 H), 5.13 (s, 2 H), 6.95-7.05 (m, 4 H), 7.08-7.18 (m, 3 H), 7.26 (d, J = 7.8 Hz, 1 H), 7.36 (t, J = 7.8 Hz, 1 H), 7.52 (br s, 2 H), 7.76 (d, J = 16.5 Hz, 1 H), 8.32 (s, 1 H). |
| Intermediate 12 | 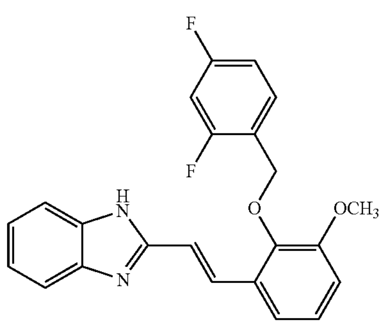 [SMILES: COc1cccc(/C=C/c2nc3ccccc3[nH]2)c1OCc1ccc(F)cc1F] | (CDCl$_3$) δ 3.89 (s, 3 H), 5.06 (s, 2 H), 6.75-6.85 (m, 2 H), 6.91 (d, J = 7.8 Hz, 1 H), 7.06-7.14 (m, 2 H), 7.17-7.21 (m, 2 H), 7.28 (br s, 1 H), 7.38-7.46 (m, 1 H), 7.60 (s, 1 H), 7.67 (s, 2 H), 7.72 (s, 1 H). |
| Intermediate 13 | 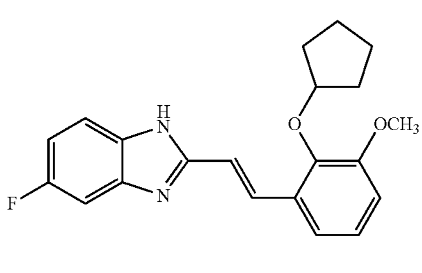 [SMILES: COc1cccc(/C=C/c2nc3cc(F)ccc3[nH]2)c1OC1CCCC1] | (CDCl$_3$) δ 1.55-1.61 (m, 2 H), 1.70-1.83 (m, 6 H), 3.82 (s, 3 H), 4.86 (br s, 1 H), 6.85 (d, J = 6.9 Hz, 1 H), 6.95-7.03 (m, 2 H), 7.10 (d, J = 6.6 Hz, 1 H), 7.14 (s, 1 H), 7.25-7.31 (m, 1 H), 7.45-7.52 (m, 1 H), 7.74 (d, J = 16.5 Hz, 1 H). |

TABLE 1-continued

Structure and ¹H NMR data of Intermediates 2 to 31

| Intermediate | Molecular Structure | ¹H NMR data (300 MHz) |
| --- | --- | --- |
| Intermediate 14 | [structure: 5-chloro-benzimidazole linked via vinyl to 2-(cyclopentyloxy)-3-methoxyphenyl] | (CDCl$_3$) δ 1.50-1.60 (m, 2 H), 1.69-1.83 (m, 6 H), 3.81 (s, 3 H), 4.86 (br s, 1 H), 6.85 (d, J = 7.2 Hz, 1 H), 7.00 (d, J = 7.8 Hz, 1 H), 7.08-7.21 (m, 3 H), 7.48 (d, J = 8.4 Hz, 1 H), 7.55 (s, 1 H), 7.75 (t, J = 17.1 Hz, 1 H). |
| Intermediate 15 | [structure: 5-methoxy-benzimidazole linked via vinyl to 2-(cyclopentyloxy)-3-methoxyphenyl] | (CDCl$_3$) δ 1.59-1.69 (m, 3 H), 1.75-1.85 (m, 5 H), 3.85 (s, 6 H), 4.86 (br s, 1 H), 6.88 (d, J = 8.4 Hz, 2 H), 7.00-7.06 (m, 2 H), 7.18 (s, 2 H), 7.50 (d, J = 8.7 Hz, 1 H), 7.71 (d, J = 17.1 Hz, 1 H). |
| Intermediate 16 | [structure: 5-(difluoromethoxy)-benzimidazole linked via vinyl to 2-(cyclopentyloxy)-3-methoxyphenyl] | (DMSO-d$_6$) δ 1.60-1.69 (m, 4 H), 1.73-1.83 (m, 4 H), 3.80 (s, 3 H), 4.85 (br s, 1 H), 6.50 (t, J = 74.4 Hz, 1 H), 6.85 (d, J = 7.8 Hz, 1 H), 6.97-7.03 (m, 2 H), 7.06-7.17 (m, 2 H), 7.37 (s, 1 H), 7.55 (d, J = 9.0 Hz, 1 H), 7.82 (d, J = 16.5 Hz, 1 H). |
| Intermediate 17 | [structure: 5,6-difluoro-benzimidazole linked via vinyl to 2-(ethoxy)-3-methoxyphenyl] | (CDCl$_3$) δ 1.35 (br s, 3 H), 3.84 (s, 3 H), 4.05-4.10 (m, 2 H), 6.88 (d, J = 8.1 Hz, 1 H), 7.04 (t, J = 7.8 Hz, 1 H), 7.13-7.19 (m, 2 H), 7.37 (t, J = 8.4 Hz, 2 H), 7.82 (d, J = 16.8 Hz, 1 H). |
| Intermediate 18 | [structure: 5,6-difluoro-benzimidazole linked via vinyl to 2-(propyloxy)-3-methoxyphenyl] | (DMSO-d$_6$) δ 0.85-0.91 (m, 3 H), 1.36-1.42 (m, 2 H), 1.66-1.72 (m, 2 H), 3.82 (s, 3 H), 3.94 (t, J = 6.9 Hz, 2 H), 6.86 (d, J = 7.8 Hz, 1 H), 7.01 (t, J = 7.8 Hz, 1 H), 7.08-7.14 (m, 1 H), 7.18 (s, 1 H), 7.36 (t, J = 8.4 Hz, 2 H), 7.83 (d, J = 16.8 Hz, 1 H). |
| Intermediate 19 | [structure: 5,6-difluoro-benzimidazole linked via vinyl to 2-(butyloxy)-3-methoxyphenyl] | (DMSO-d$_6$) δ 0.87 (s, 3 H), 1.22-1.31 (m, 2 H), 1.35-1.43 (m, 2 H), 1.74 (br s, 2 H), 3.82 (s, 3 H), 3.94 (s, 2 H), 7.06-7.12 (m, 2 H), 7.14-7.20 (m, 1 H), 7.32 (d, J = 7.5 Hz, 1 H), 7.58 (s, 2 H), 7.89 (d, J = 16.5 Hz, 1 H). |

TABLE 1-continued

Structure and ¹H NMR data of Intermediates 2 to 31

| Intermediate | Molecular Structure | ¹H NMR data (300 MHz) |
|---|---|---|
| Intermediate 20 | 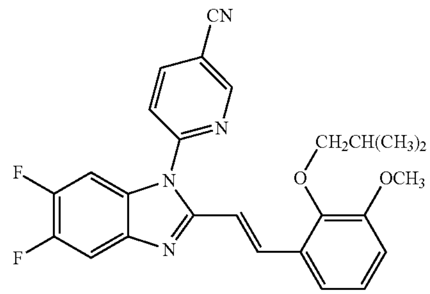 | (CDCl$_3$) δ 0.92 (d, J = 6.3 Hz, 6 H), 1.94-2.01 (m, 1 H), 3.66 (d, J = 6.3 Hz, 2 H), 3.80 (s, 3 H), 6.85 (d, J = 7.8 Hz, 1 H), 6.95-7.01 (m, 1 H), 7.03-7.09 (m, 1 H), 7.15 (d, J = 16.8 Hz, 1 H), 7.34 (t, J = 8.1 Hz, 2 H), 7.85 (d, J = 16.8 Hz, 1 H). |
| Intermediate 21 | 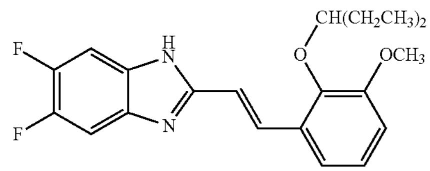 | (CDCl$_3$) δ 0.87-0.931 (m, 6 H), 1.56-1.66 (m, 4 H), 3.82 (s, 3 H), 4.14-4.20 (m, 1 H), 6.87 (d, J = 8.1 Hz, 1 H), 7.01 (t, J = 7.8 Hz, 1 H), 7.10-7.16 (m, 2 H), 7.35 (br s, 2 H), 7.82 (d, J = 17.1 Hz, 1 H). |
| Intermediate 22 | 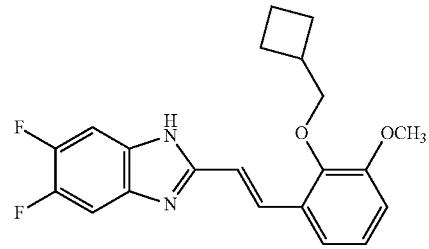 [SMILES: COc1cccc(/C=C/c2nc3cc(F)c(F)cc3[nH]2)c1OCC1CCC1] | (CDCl$_3$) δ 1.81-1.92 (m, 4 H), 2.06 (br s, 2 H), 2.73 (br s, 1 H), 3.84 (s, 3 H), 3.99 (d, J = 6.9 Hz, 2 H), 6.88 (d, J = 7.8 Hz, 1 H), 7.03 (t, J = 7.8 Hz, 1 H), 7.12-7.18 (m, 2 H), 7.37 (t, J = 8.1 Hz, 2 H), 7.78 (d, J = 16.5 Hz, 1 H). |
| Intermediate 23 | 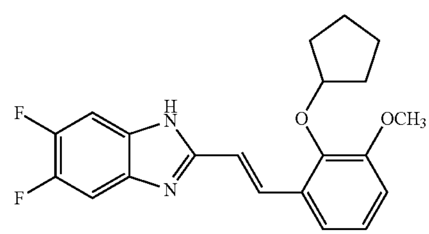 [SMILES: COc1cccc(/C=C/c2nc3cc(F)c(F)cc3[nH]2)c1OC1CCCC1] | (CDCl$_3$) δ 1.55-1.61 (m, 2 H), 1.69-1.87 (m, 6 H), 3.81 (s, 3 H), 4.86 (br s, 1 H), 6.85 (d, J = 7.8 Hz, 1 H), 6.98-7.05 (m, 2 H), 7.11 (d, J = 7.2 Hz, 1 H), 7.34 (t, J = 8.4 Hz, 2 H), 7.73 (d, J = 16.5 Hz, 1 H). |
| Intermediate 24 | 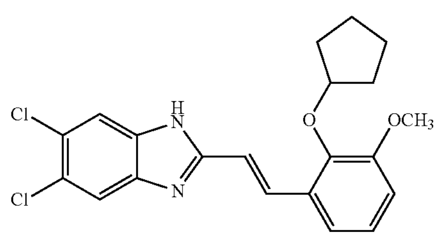 [SMILES: COc1cccc(/C=C/c2nc3cc(Cl)c(Cl)cc3[nH]2)c1OC1CCCC1] | (CDCl$_3$) δ 1.67-1.75 (m, 4 H), 1.77-1.85 (m, 4 H), 3.79 (s, 3 H), 4.89 (br s, 1 H), 6.87 (d, J = 7.8 Hz, 1 H), 6.99-7.05 (m, 2 H), 7.07-7.12 (m, 1 H), 7.68 (s, 2 H), 7.81 (d, J = 16.5 Hz, 1 H). |
| Intermediate 25 | 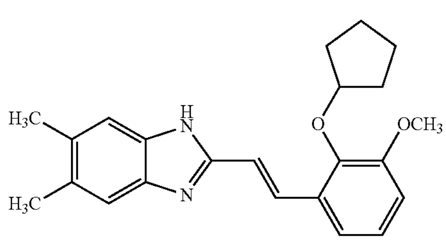 [SMILES: COc1cccc(/C=C/c2nc3cc(C)c(C)cc3[nH]2)c1OC1CCCC1] | (CDCl$_3$) δ 1.66-1.70 (m, 2 H), 1.74-1.83 (m, 6 H), 2.36 (s, 6 H), 3.82 (s, 3 H), 4.84 (br s, 1 H), 6.85 (d, J = 7.8 Hz, 1 H), 7.01 (t, J = 7.8 Hz, 1 H), 7.12-7.18 (m, 2 H), 7.37 (br s, 2 H), 7.70 (d, J = 16.5 Hz, 1 H). |

TABLE 1-continued

Structure and ¹H NMR data of Intermediates 2 to 31

| Intermediate | Molecular Structure | ¹H NMR data (300 MHz) |
| --- | --- | --- |
| Intermediate 26 | 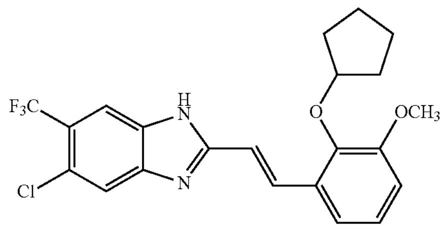 [SMILES: COc1cccc(/C=C/c2nc3cc(Cl)c(C(F)(F)F)cc3[nH]2)c1OC1CCCC1] | (DMSO-d₆) δ 1.65-1.74 (m, 4 H), 1.77-1.85 (m, 4 H), 3.83 (s, 3 H), 4.91 (br s, 1 H), 6.89 (d, J = 7.8 Hz, 1 H), 7.04 (t, J = 8.1 Hz, 1 H), 7.10-7.16 (m, 2 H), 7.70 (s, 1 H), 7.87 (d, J = 16.8 Hz, 1 H), 7.95 (s, 1 H). |
| Intermediate 27 | 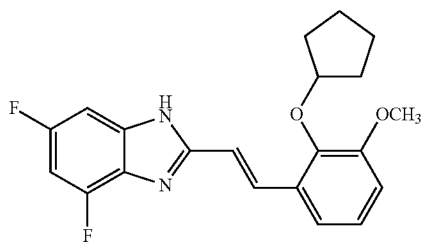 [SMILES: COc1cccc(/C=C/c2nc3c(F)cc(F)cc3[nH]2)c1OC1CCCC1] | (DMSO-d₆) δ 1.64-1.72 (m, 4 H), 1.72-1.81 (m, 4 H), 3.82 (s, 3 H), 4.85 (br s, 1 H), 7.04-7.13 (m, 4 H), 7.18 (s, 1 H), 7.32 (d, J = 6.9 Hz, 1 H), 7.88 (d, J = 16.5 Hz, 1 H). |
| Intermediate 28 | 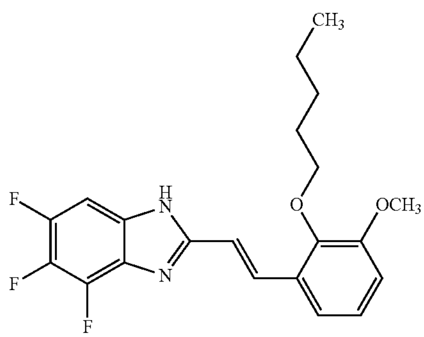 [SMILES: CCCCCOc1c(/C=C/c2nc3c(F)c(F)c(F)cc3[nH]2)cccc1OC] | (DMSO-d₆) δ 1.66-1.75 (m, 8 H), 2.67 (br s, 2 H), 2.93 (br s, 2 H), 4.73 (br s, 1 H), 7.01-7.12 (m, 6 H), 7.91 (d, J = 7.2 Hz, 2 H), 8.05-8.16 (m, 2 H), 9.40 (s, 1 H), 9.74 (s, 1 H). |
| Intermediate 29 | 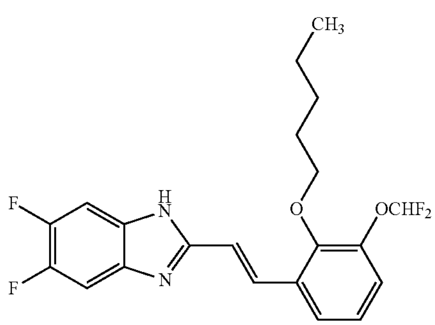 [SMILES: CCCCCOc1c(/C=C/c2nc3cc(F)c(F)cc3[nH]2)cccc1OC(F)F] | (CDCl₃) δ 0.89 (br s, 3 H), 1.25-1.36 (m, 4 H), 1.74 (t, J = 6.9 Hz, 2 H), 3.96 (t, J = 6.3 Hz, 2 H), 6.52 (t, J = 74.7 Hz, 1 H), 7.09 (d, J = 7.8 Hz, 1 H), 7.14 (d, J = 7.2 Hz, 1 H), 7.21 (s, 1 H), 7.34-7.40 (m, 3 H), 7.76 (d, J = 16.5 Hz, 1 H). |
| Intermediate 30 | 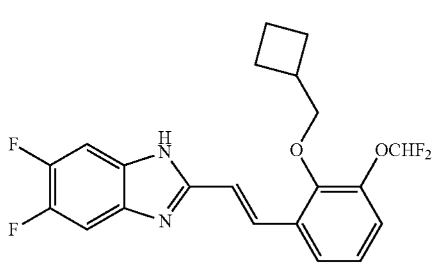 [SMILES: Fc1cc2nc(/C=C/c3cccc(OC(F)F)c3OCC3CCC3)[nH]c2cc1F] | (DMSO-d₆) δ 1.85-1.19 (m, 4 H), 2.07 (br s, 2 H), 2.77 (s, 1 H), 3.97 (br s, 2 H), 7.23 (t, J = 79.5 Hz, 1 H), 7.24-7.30 (m, 3 H), 7.64 (br s, 3 H), 7.85 (d, J = 16.5 Hz, 1 H). |

TABLE 1-continued

Structure and ¹H NMR data of Intermediates 2 to 31

| Intermediate | Molecular Structure | ¹H NMR data (300 MHz) |
|---|---|---|
| Intermediate 31 | 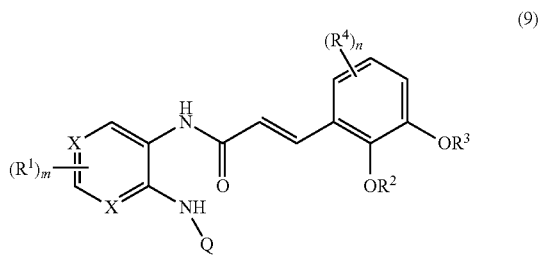 | (DMSO-$d_6$) δ 1.59-1.70 (m, 4 H), 1.72-1.82 (m, 4 H), 4.75 (s, 1 H), 7.20 (t, J = 74.1 Hz, 1 H), 7.21-7.26 (m, 3 H), 7.63 (br s, 3 H), 7.85 (d, J = 16.5 Hz, 1 H). |

It may be noted that unsymmetrically substituted benzimidazole intermediates described above (e.g. Intermediates 13 to 16, 26, 27, 28) on substitution at imidazole nitrogen leads to regioisomeric mixture of products. To overcome this problem, compounds of the present invention were also prepared from acrylamide derivatives (e.g. Intermediate 32). The synthetic method for the preparation of acrylamide derivative of the formula (9) where $R^1$, $R^2$, $R^3$, $R^4$, Q, X, m, and n are as described previously, is given below.

(9)

[Structure of formula (9)]

Intermediate 32

(2E)-N-{4-chloro-2-[(5-cyanopyridin-2-yl)amino]phenyl}-3-[3-methoxy-2-(2-methylpropoxy)phenyl]prop-2-enamide

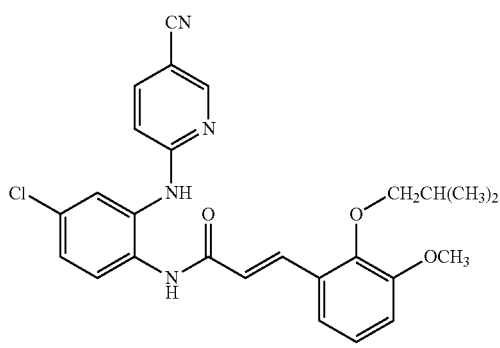

Step 1: 6-[(5-chloro-2-nitrophenyl)amino]nicotinonitrile: To a well stirred solution of 5-chloro-2-nitroaniline (2.0 g, 11.0 mmol) in dry N,N-dimethylacetamide (DMA; 15 ml), cesium carbonate ($Cs_2CO_3$; 757 mg, 2.3 mmol) and 6-chloronicotinonitrile (193 mg, 1.3 mmol) were added and reaction mixture was heated at 130° C. for 3 h. After completion of the reaction, the reaction mixture was cooled to room temperature, extracted with ethyl acetate (2×100 ml), and the combined organic layers were washed with water (2×50 ml), brine (20 ml), dried ($Na_2SO_4$), filtered and concentrated under reduced pressure to yield 2.5 g of the product.

Step 2: 6-[(2-amino-5-chlorophenyl)amino]nicotinonitrile: To a well stirred solution of step 1 intermediate (2.5 g, 9.1 mmol) in ethanol (45 ml), aqueous solution of ammonium chloride (4.87 g, 91.0 mmol) was added and the reaction mixture was refluxed at 100° C. After 15 minutes iron powder (1.5 g, 27 mmol) was added to it portionwise and was further refluxed for 2 h. After the completion of reaction, excess of ethanol was evaporated under reduced pressure; the reaction mixture was diluted with chloroform (200 ml) and filtered through celite bed. The combined organic layers were washed with water (2×50 ml) and brine, dried ($Na_2SO_4$), filtered and concentrated under reduced pressure to yield 1.8 g of the product.

Step 3: (2E)-N-{4-chloro-2-[(5-cyanopyridin-2-yl)amino]phenyl}-3-(2-isobutoxy-3-methoxyphenyl)acrylamide: To a well stirred solution of (2E)-3-(2-isobutoxy-3-methoxyphenyl)acrylic acid (613 mg, 2.4 mmol) in DCM (10 ml), oxalyl chloride (613 mg, 2.4 mmol) was added dropwise and few drops of dimethylformamide (DMF) were also added. The reaction mixture was stirred at room temperature for 3 h to obtain the corresponding acid chloride from which the excess of DCM was evaporated under reduced pressure. The solution of Step 2 intermediate (500 mg, 2 mmol) in pyridine (10 ml) was added dropwise to the acid chloride at 0° C. and the reaction mixture was stirred at room temperature for 2 h. After completion of the reaction, the reaction mixture was diluted with water (20 ml) and extracted with ethyl acetate (2×50 ml), combined organic layers washed with water (2×20 ml) and brine, dried ($Na_2SO_4$), filtered and concentrated under reduced pressure to yield 215 mg of the product. ¹H NMR (300 MHz, $CDCl_3$) δ 1.04 (d, J=6.3 Hz, 6H), 2.06-2.15 (m, 1H), 3.74 (d, J=6.6 Hz, 2H), 3.86 (s, 3H), 6.53 (d, J=15.6 Hz, 1H), 6.64 (d, J=8.4 Hz, 1H), 6.93 (d, J=7.8 Hz, 1H), 7.01 (t, J=7.8 Hz, 1H), 7.08 (d, J=7.5 Hz, 1H), 7.15 (d, J=8.7 Hz, 1H), 7.56 (d, J=6.9 Hz, 2H), 7.65 (d, J=7.8 Hz, 1H), 7.83 (s, 2H), 8.11 (d, J=15.6 Hz, 1H), 8.45 (s, 1H).

The intermediates 33 to 38 were prepared by the procedure described in Intermediate 32 by using appropriate 2-nitroaniline, 6-chloronicotinonitrile and 2,3-dialkoxycinnamic acid derivatives. The structure and characterization data for these intermediates are given in Table 2.

TABLE 2

Structure and ¹H NMR data of acrylamides 33 to 38

| Intermediate | Molecular Structure | ¹H NMR data (300 MHz) |
|---|---|---|
| Intermediate 33 | 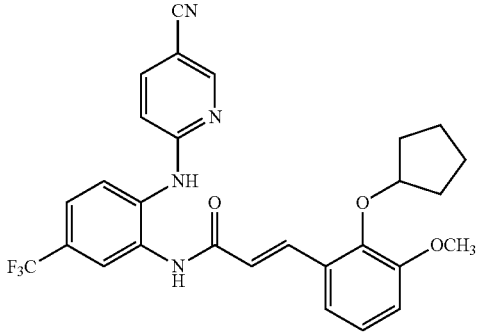 [SMILES: COc1cccc(/C=C/C(=O)Nc2cc(C(F)(F)F)ccc2Nc2ccc(C#N)cn2)c1OC1CCCC1] | (DMSO-d₆) δ 1.59-1.65 (m, 4 H), 1.70-1.80 (m, 4 H), 3.82 (s, 3 H), 4.87 (br s, 1 H), 6.88-6.99 (m, 2 H), 7.09-7.15 (m, 2 H), 7.19 (br s, 1 H), 7.50 (d, J = 8.4 Hz, 1 H), 7.88-7.98 (m, 3 H), 8.22 (s, 1 H), 8.55 (s, 1 H), 9.38 (s, 1 H), 9.83 (s, 1 H). |
| Intermediate 34 | 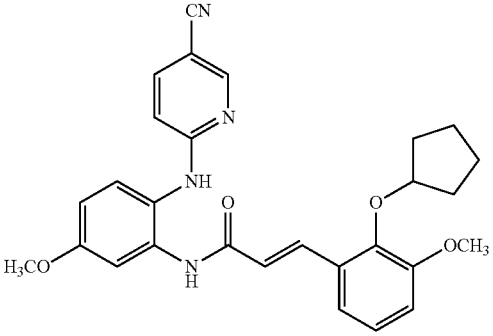 [SMILES: COc1ccc(Nc2ccc(C#N)cn2)c(NC(=O)/C=C/c2cccc(OC)c2OC2CCCC2)c1] | (CDCl₃) δ 1.57-1.67 (m, 3 H), 1.75-1.84 (m, 5 H), 3.85 (s, 6 H), 4.87 (br s, 1 H), 6.42 (d, J = 8.7 Hz, 1 H), 6.49 (d, J = 15.9 Hz, 1 H), 6.74 (d, J = 6.3 Hz, 1 H), 6.91 (d, J = 7.8 Hz, 1 H), 7.00 (t, J = 7.8 Hz, 1 H), 7.09 (d, J = 7.5 Hz, 2 H), 7.23 (d, J = 8.7 Hz, 1 H), 7.60 (d, J = 8.1 Hz, 1 H), 7.79 (br s, 2 H), 8.04 (d, J = 15.6 Hz, 1 H), 8.42 (s, 1 H). |
| Intermediate 35 | 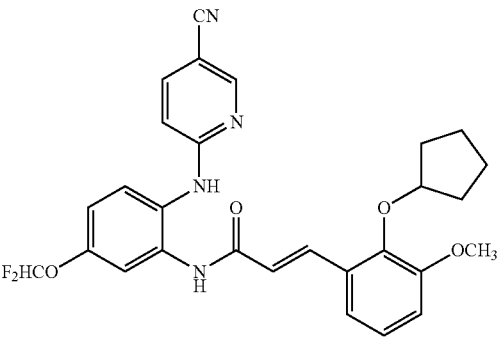 [SMILES: COc1cccc(/C=C/C(=O)Nc2cc(OC(F)F)ccc2Nc2ccc(C#N)cn2)c1OC1CCCC1] | (CDCl₃) δ 1.58-1.66 (m, 3 H), 1.84 (br s, 5 H), 3.86 (s, 3 H), 4.89 (br s, 1 H), 6.47-6.57 (m, 3 H), 6.91-7.01 (m, 3 H), 7.10 (d, J = 7.8 Hz, 1 H), 7.40 (d, J = 8.7 Hz, 1 H), 7.64 (d, J = 8.4 Hz, 1 H), 7.81 (s, 1 H), 7.92 (s, 1 H), 8.08 (d, J = 16.2 Hz, 1 H), 8.42 (s, 1 H). |
| Intermediate 36 | 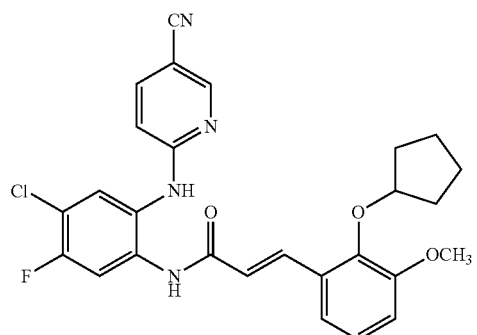 | (CDCl₃) δ 1.59-1.67 (m, 5 H), 1.83 (br s, 4 H), 3.85 (s, 3 H), 4.89 (br s, 1 H), 6.46 (d, J = 15.6 Hz, 1 H), 6.54 (d, J = 8.4 Hz, 1 H), 6.92 (d, J = 7.2 Hz, 1 H), 6.99 (t, J = 7.8 Hz, 1 H), 7.08 (d, J = 7.2 Hz, 1 H), 7.29 (s, 1 H), 7.46 (d, J = 6.9 Hz, 1 H), 7.68 (d, J = 7.8 Hz, 1 H), 7.85 (s, 1 H), 7.96 (d, J = 9.6 Hz, 1 H), 8.07 (d, J = 15.0 Hz, 1 H), 8.45 (s, 1 H). |

TABLE 2-continued

Structure and ¹H NMR data of acrylamides 33 to 38

| Intermediate | Molecular Structure | ¹H NMR data (300 MHz) |
|---|---|---|
| Intermediate 37 | 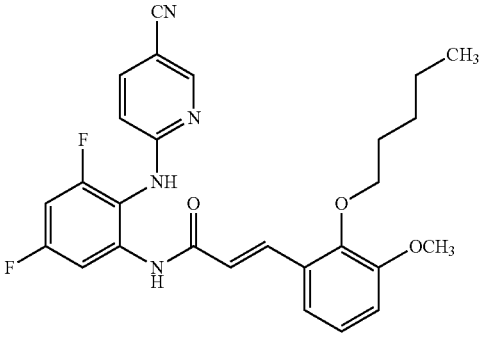 [SMILES: CCCCCOc1c(/C=C/C(=O)Nc2cc(F)cc(F)c2Nc2ccc(C#N)cn2)cccc1OC] | (DMSO-$d_6$) δ 0.86 (t, J = 6.3 Hz, 3 H), 1.29-1.36 (m, 4 H), 1.68 (t, J = 6.9 Hz, 2 H), 3.80 (s, 3 H), 3.90 (t, J = 6.3 Hz, 2 H), 6.75 (br s, 1 H), 7.02-7.16 (m, 5 H), 7.86-8.00 (m, 3 H), 8.44 (s, 1 H), 8.95 (s, 1 H), 9.71 (s, 1 H). |
| Intermediate 38 | 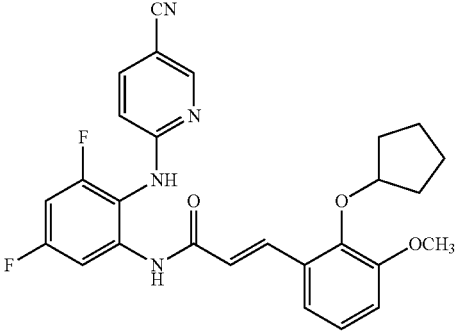 [SMILES: COc1cccc(/C=C/C(=O)Nc2cc(F)cc(F)c2Nc2ccc(C#N)cn2)c1OC1CCCC1] | (DMSO-$d_6$) δ 1.58-1.64 (m, 4 H), 1.72-1.78 (m, 4 H), 3.81 (s, 3 H), 4.85 (br s, 1 H), 6.77 (br s, 1 H), 7.01 (d, J = 15.6 Hz, 1 H), 7.08-7.18 (m, 4 H), 7.84-8.00 (m, 3 H), 8.44 (s, 1 H), 8.95 (s, 1 H), 9.69 (s, 1 H). |

Intermediates 39 to 55 were prepared by following the approach described in Scheme 3 by using appropriate aminopyridine with chloro-3-nitropyridine and 2,3-dialkoxy cinnamic acid derivative as follows:

Intermediate 39

(2E)-N-{2-[(5-cyanopyridin-2-yl)amino]pyridin-3-yl}-3-[2-(cyclopentyloxy)-3-methoxyphenyl]prop-2-enamide

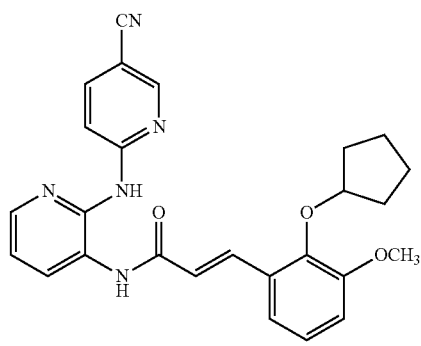 [SMILES: COc1cccc(/C=C/C(=O)Nc2cccnc2Nc2ccc(C#N)cn2)c1OC1CCCC1]

Step 1: 6-[(3-nitropyridin-2-yl)amino]nicotinonitrile: To a well stirred solution of 6-aminonicotinonitrile (0.631 g, 5.29 mmol) in dry DMA (10 ml), $CS_2CO_3$ (2.157 g, 6.62 mmol) and 2-chloro-3-nitropyridine (0.700 g, 4.415 mmol) were added and reaction mixture was heated at 80° C. under nitrogen atmosphere for 24 h. After completion the reaction mixture was cooled to room temperature, extracted with ethyl acetate (2×100 ml), combined organic layers washed with water (2×50 ml) and brine, dried ($Na_2SO_4$), filtered and concentrated under reduced pressure to yield 543 mg of the product.

Step 2: 6-[(3-aminopyridin-2-yl)amino]nicotinonitrile: To the stirred solution of step-1 intermediate (500 mg, 2.202 mmol) in ethanol (5 ml) was added aqueous solution of ammonium chloride (1.178 g, 22.026 mmol) and the reaction mixture heated to 90-100° C. Iron powder was then added to the reaction mixture portion wise and it was further refluxed for 2 h. After the completion of the reaction, the reaction mixture was diluted with chloroform (100 ml) and filtered. The filtrate was washed with minimum amount of water, brine (25 ml), dried over $Na_2SO_4$ and concentrated to yield 423 mg of the product.

Step 3: To a well stirred and cooled solution of (2E)-3-[2-(cyclopentyloxy)-3-methoxyphenyl] acrylic acid (300 mg, 1.144 mmol) in DCM (5 ml), oxalyl chloride (218 mg, 1.716 mmol) was added dropwise and few drops of DMF were also added. The reaction mixture was then stirred for 4 h at room temperature and after the formation of the acid chloride the solvent was evaporated under reduced pressure. The solution of step-2 intermediate (218 mg, 1.030 mmol) in pyridine (5 ml) was added dropwise to the concentrated reaction mixture at 0° C. over 15 mins and then it was stirred at room temperature for 3 h. After completion of the reaction, the reaction mixture was diluted with water (50 ml), extracted with ethyl acetate (3×25 ml) and the combined organic layers were washed with water (2×20 ml), brine (50 ml) and dried over ($Na_2SO_4$). The crude product obtained after evaporation of the solvent under reduced pressure was purified by recrystallization to give 312 mg of the product. ¹H NMR data (300 MHz, DMSO-$d_6$) δ 1.58-1.68 (m, 4H), 1.73-1.79 (m, 4H), 3.82 (s, 3H), 4.87 (br s, 1H), 6.86 (d, J=15.6 Hz, 1H), 7.13-7.23 (m, 4H), 7.88-7.93 (m, 2H), 8.05-8.12 (m, 2H), 8.18 (br s, 1H), 8.63 (br s, 1H), 9.55 (br s, 1H), 9.96 (br s, 1H).

The intermediates 40 to 55 were prepared by the procedure described in intermediate 39 and the structure and characterization data of these intermediates are given in Table 3.

TABLE 3

Structure and ¹H NMR data of Intermediates 40 to 55

| Intermediate | Molecular Structure | ¹H NMR data (300 MHz) |
|---|---|---|
| Intermediate 40 | 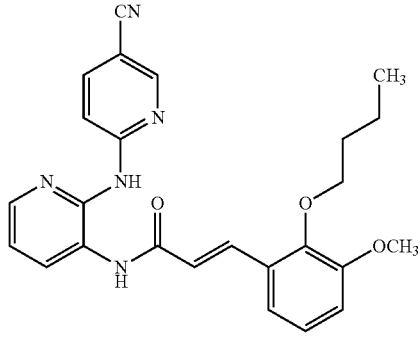 [SMILES: CCCCOc1c(/C=C/C(=O)Nc2cccnc2Nc2ccc(C#N)cn2)cccc1OC] | (DMSO-$d_6$) δ 0.92 (t, J = 7.5 Hz, 3 H), 1.47 (d, J = 6.6 Hz, 2 H), 1.67 (d, J = 6.3 Hz, 2 H), 3.82 (s, 3 H), 3.91 (br s, 2 H), 6.90 (d, J = 16.2 Hz, 1 H), 7.12-7.23 (m, 4 H), 7.87-7.93 (m, 2 H), 8.08 (d, J = 7.5 Hz, 2 H), 8.19 (br s, 1 H), 8.64 (br s, 1 H), 8.64 (br s, 1 H), 9.57 (br s, 1 H), 9.98 (br s, 1 H). |
| Intermediate 41 | 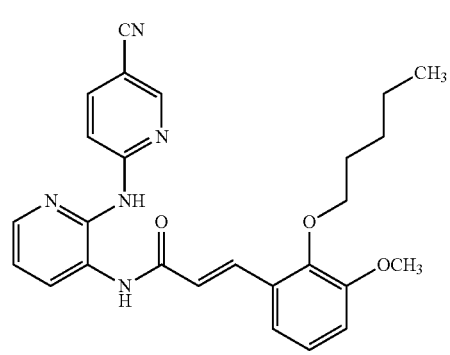 [SMILES: CCCCCOc1c(/C=C/C(=O)Nc2cccnc2Nc2ccc(C#N)cn2)cccc1OC] | (DMSO-$d_6$) δ 0.87 (s, 3 H), 1.33-1.42 (m, 4 H), 1.69 (s, 2 H), 3.82 (s, 3 H), 3.92 (br s, 2 H), 6.90 (d, J = 15.6 Hz, 1 H), 7.11-7.22 (m, 4 H), 7.87-7.92 (m, 2 H), 8.06 (d, J = 7.8 Hz, 2 H), 8.19 (br s, 1 H), 8.63 (s, 1 H), 9.55 (s, 1 H), 9.98 (s, 1 H). |
| Intermediate 42 | 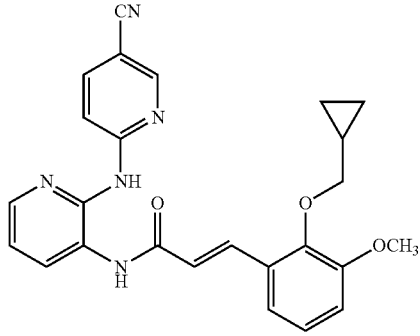 [SMILES: COc1cccc(/C=C/C(=O)Nc2cccnc2Nc2ccc(C#N)cn2)c1OCC1CC1] | (DMSO-$d_6$) δ 0.24 (s, 2 H), 0.51 (d, J = 6.6 Hz, 2 H), 1.15 (br s, 1 H), 3.80 (t, J = 6.3 Hz, 5 H), 6.91 (d, J = 16.2 Hz, 1 H), 7.11-7.22 (m, 4 H), 7.88-8.05 (m, 2 H), 8.08-8.13 (m, 2 H), 8.19 (br s, 1 H), 8.63 (br s, 1 H), 9.55 (s, 1 H), 9.98 (br s, 1 H). |
| Intermediate 43 | 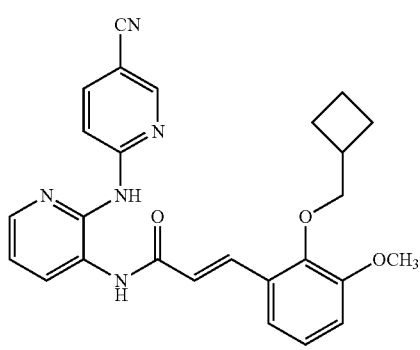 [SMILES: COc1cccc(/C=C/C(=O)Nc2cccnc2Nc2ccc(C#N)cn2)c1OCC1CCC1] | (DMSO-$d_6$) δ 1.83 (s, 4 H), 2.06 (br s, 2 H), 2.66 (br s, 1 H), 3.82 (s, 3 H), 3.92 (d, J = 6.9 Hz, 2 H), 6.89 (d, J = 16.2 Hz, 1 H), 7.11-7.22 (m, 4 H), 7.89-7.94 (m, 2 H), 8.08 (t, J = 7.8 Hz, 2 H), 8.19 (s, 1 H), 8.64 (s, 1 H), 9.55 (s, 1 H), 9.97 (s, 1 H). |

TABLE 3-continued

Structure and ¹H NMR data of Intermediates 40 to 55

| Intermediate | Molecular Structure | ¹H NMR data (300 MHz) |
|---|---|---|
| Intermediate 44 | 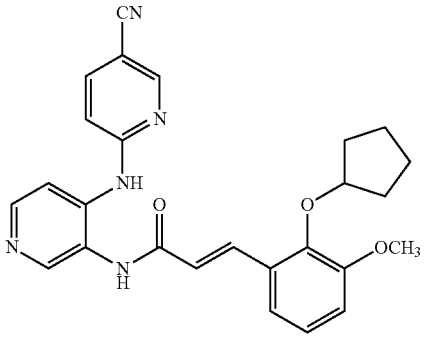 [SMILES: COc1cccc(/C=C/C(=O)Nc2cnccc2Nc2ccc(C#N)cn2)c1OC1CCCC1] | (DMSO-d₆) δ 1.56-1.66 (m, 4 H), 1.67-1.77 (m, 4 H), 3.82 (s, 3 H), 4.89 (br s, 1 H), 7.08 (s, 2 H), 7.33 (s, 2 H), 7.61 (s, 1 H), 8.04 (d, J = 8.1 Hz, 1 H), 8.23 (d, J = 16.2 Hz, 1 H), 8.43 (s, 1 H), 8.74 (d, J = 7.8 Hz, 1 H), 9.10 (s, 1 H), 9.27 (s, 1 H). |
| Intermediate 45 | 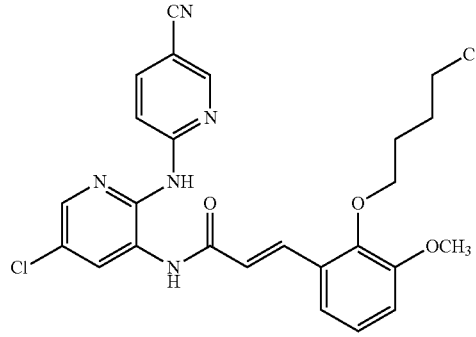 | (DMSO-d₆) δ 0.88 (d, J = 6.3 Hz, 3 H), 1.32-1.42 (m, 4 H), 1.69 (t, J = 6.3 Hz, 2 H), 3.82 (s, 3 H), 3.92 (t, J = 6.0 Hz, 2 H), 6.91 (d, J = 15.6 Hz, 1 H), 7.12 (br s, 2 H), 7.22 (br s, 1 H), 7.80 (d, J = 8.7 Hz, 1 H), 7.91 (d, J = 15.6 Hz, 1 H), 8.08 (d, J = 7.8 Hz, 1 H), 8.21 (s, 1 H), 8.36 (s, 1 H), 8.66 (s, 1 H), 9.73 (s, 1 H), 9.99 (s, 1 H). |
| Intermediate 46 | 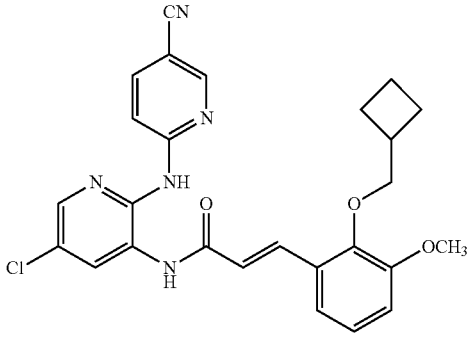 [SMILES: COc1cccc(/C=C/C(=O)Nc2cc(Cl)cnc2Nc2ccc(C#N)cn2)c1OCC1CCC1] | (DMSO-d₆) δ 1.83 (br s, 4 H), 2.05 (br s, 2 H), 2.64-2.71 (m, 1 H), 3.82 (s, 3 H), 3.93 (d, J = 6.6 Hz, 2 H), 6.90 (d, J = 15.6 Hz, 1 H), 7.11-7.21 (m, 2 H), 7.22-7.27 (m, 1 H), 7.79 (d, J = 8.7 Hz, 1 H), 7.93 (d, J = 16.2 Hz, 1 H), 8.08 (dd, J = 2.4, 9.3 Hz, 1 H), 8.21 (s, 1 H), 8.37 (s, 1 H), 8.65 (s, 1 H), 9.72 (s, 1 H), 9.98 (s, 1 H). |
| Intermediate 47 | 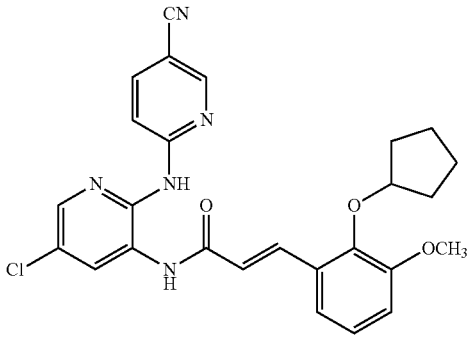 [SMILES: COc1cccc(/C=C/C(=O)Nc2cc(Cl)cnc2Nc2ccc(C#N)cn2)c1OC1CCCC1] | (DMSO-d₆) δ 1.59-1.65 (m, 4 H), 1.72-1.78 (m, 4 H), 3.82 (s, 3 H), 4.88 (br s, 1 H), 6.87 (d, J = 15.6 Hz, 1 H), 7.11 (br s, 2 H), 7.23 (br s, 1 H), 7.79 (d, J = 9.0 Hz, 1 H), 7.92 (d, J = 15.6 Hz, 1 H), 8.08 (d, J = 8.1 Hz, 1 H), 8.21 (s, 1 H), 8.38 (s, 1 H), 8.65 (s, 1 H), 9.73 (s, 1 H), 9.97 (s, 1 H). |

TABLE 3-continued

Structure and ¹H NMR data of Intermediates 40 to 55

| Intermediate | Molecular Structure | ¹H NMR data (300 MHz) |
|---|---|---|
| Intermediate 48 | 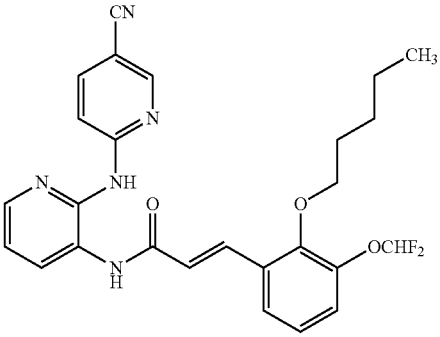 | (CDCl₃) δ 0.87 (t, J = 6.9 Hz, 3 H), 1.29-1.36 (m, 4 H), 1.73 (t, J = 6.9 Hz, 2 H), 3.94 (t, J = 6.3 Hz, 2 H), 6.94-7.00 (m, 1 H), 7.18-7.24 (m, 2 H), 7.25-7.31 (m, 2 H), 7.56 (d, J = 7.5 Hz, 1 H), 7.84 (d, J = 16.2 Hz, 1 H), 7.90 (d, J = 8.7 Hz, 1 H), 8.06 (d, J = 7.8 Hz, 2 H), 8.21 (br s, 1 H), 8.63 (s, 1 H), 9.56 (s, 1 H), 10.02 (s, 1 H). |
| Intermediate 49 | 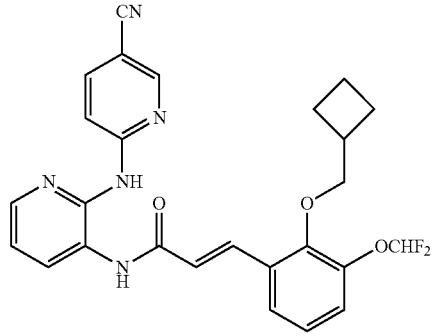 [SMILES: N#Cc1ccc(Nc2ncccc2NC(=O)/C=C/c2cccc(OC(F)F)c2OCC2CCC2)nc1] | (DMSO-d₆) δ 1.85 (s, 4 H), 2.06 (s, 2 H), 2.70 (br s, 1 H), 3.94 (d, J = 6.6 Hz, 2 H), 6.92-6.98 (m, 1 H), 7.19-7.28 (m, 4 H), 7.56 (d, J = 6.9 Hz, 1 H), 7.84-7.91 (m, 2 H), 8.05-8.12 (m, 2 H), 8.19 (s, 1 H), 8.63 (s, 1 H), 9.55 (s, 1 H), 10.01 (s, 1 H). |
| Intermediate 50 | 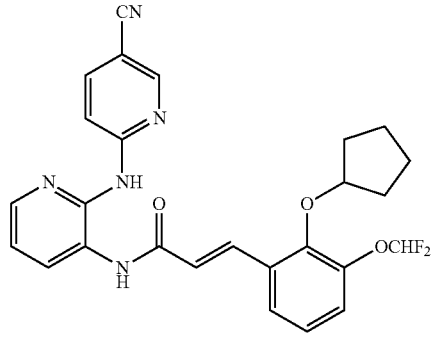 [SMILES: N#Cc1ccc(Nc2ncccc2NC(=O)/C=C/c2cccc(OC(F)F)c2OC2CCCC2)nc1] | (DMSO-d₆) δ 1.59-1.69 (m, 4 H), 1.71-1.81 (m, 4 H), 4.75 (br s, 1 H), 6.93 (d, J = 15.6 Hz, 1 H), 7.16-7.23 (m, 2 H), 7.25-7.31 (m, 2 H), 7.56 (d, J = 7.5 Hz, 1 H), 7.83-7.90 (m, 2 H), 8.05-8.13 (m, 2 H), 8.20 (s, 1 H), 8.63 (s, 1 H), 9.56 (s, 1 H), 10.00 (s, 1 H). |
| Intermediate 51 | 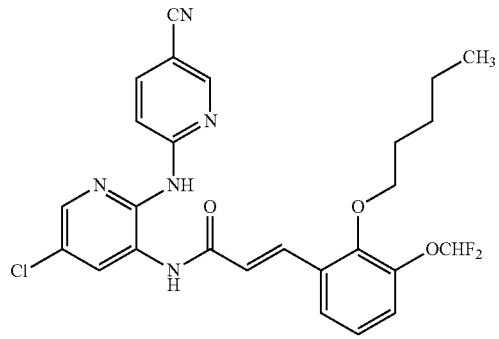 [SMILES: CCCCCOc1c(/C=C/C(=O)Nc2cc(Cl)cnc2Nc2ccc(C#N)cn2)cccc1OC(F)F] | (CDCl₃) δ 1.40 (br s, 3 H), 1.60 (br s, 2 H), 1.79 (br s, 2 H), 3.99 (br s, 2 H), 6.55 (t, J = 74.1 Hz, 1 H), 6.65 (d, J = 15.6 Hz, 1 H), 7.09 (br s, 1 H), 7.20 (br s, 2 H), 7.39 (s, 1 H), 7.80 (br s, 2 H), 8.04 (d, J = 15.6 Hz, 1 H), 8.15 (s, 2 H), 8.48 (br s, 1 H), 8.63 (s, 1 H), 9.56 (s, 1 H). |

TABLE 3-continued

Structure and ¹H NMR data of Intermediates 40 to 55

| Intermediate | Molecular Structure | ¹H NMR data (300 MHz) |
|---|---|---|
| Intermediate 52 | 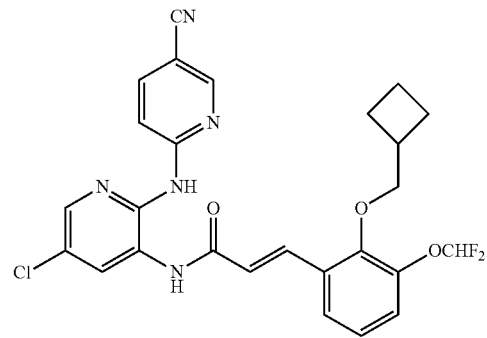 [SMILES: N#Cc1ccc(Nc2ncc(Cl)cc2NC(=O)/C=C/c2cccc(OC(F)F)c2OCC2CCC2)nc1] | (DMSO-d$_6$) δ 1.85 (s, 4 H), 2.06 (br s, 2 H), 2.70 (br s, 1 H), 3.93 (s, 2 H), 6.93-6.99 (m, 1 H), 7.21-7.29 (m, 3 H), 7.54 (br s, 1 H), 7.79-7.89 (m, 2 H), 8.07 (br s, 1 H), 8.22 (s, 1 H), 8.37 (s, 1 H), 8.66 (s, 1 H), 9.73 (s, 1 H), 10.03 (s, 1 H). |
| Intermediate 53 | 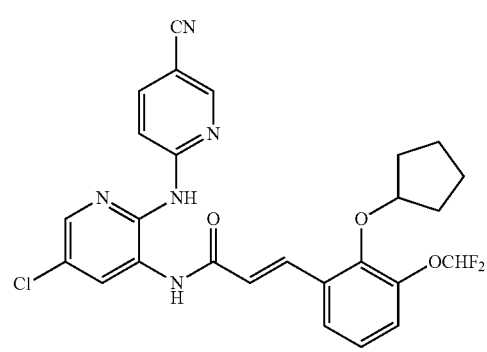 [SMILES: N#Cc1ccc(Nc2ncc(Cl)cc2NC(=O)/C=C/c2cccc(OC(F)F)c2OC2CCCC2)nc1] | (DMSO-d$_6$) δ 1.60-1.69 (m, 4 H), 1.78-1.85 (m, 4 H), 4.75 (br s, 1 H), 6.94 (d, J = 15.6 Hz, 1 H), 7.20-7.28 (m, 3 H), 7.55 (d, J = 6.9 Hz, 1 H), 7.78 (d, J = 8.4 Hz, 1 H), 7.87 (d, J = 16.2 Hz, 1 H), 8.08 (d, J = 7.8 Hz, 1 H), 8.22 (s, 1 H), 8.38 (s, 1 H), 8.65 (s, 1 H), 9.73 (s, 1 H), 10.02 (s, 1 H). |
| Intermediate 54 | 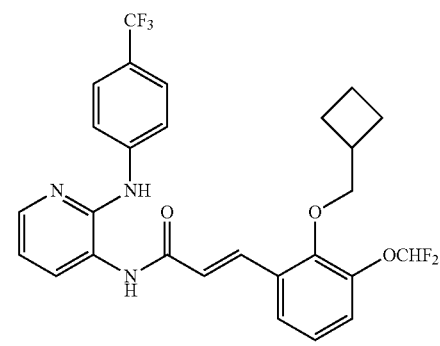 [SMILES: O=C(/C=C/c1cccc(OC(F)F)c1OCC1CCC1)Nc1cccnc1Nc1ccc(C(F)(F)F)cc1] | (CDCl$_3$) δ 1.76-1.88 (m, 4 H), 2.13 (br s, 2 H), 2.78 (br s, 1 H), 4.00 (d, J = 6.3 Hz, 2 H), 6.54 (t, J = 74.1 Hz, 1 H), 6.68 (d, J = 15.3 Hz, 1 H), 6.97 (t, J = 6.9 Hz, 1 H), 7.09 (t, J = 7.5 Hz, 1 H), 7.17-7.25 (m, 2 H), 7.39 (br s, 3 H), 7.51 (d, J = 7.5 Hz, 3 H), 7.82 (br s, 1 H), 8.06 (d, J = 15.6 Hz, 1 H), 8.18 (br s, 1 H). |
| Intermediate 55 | 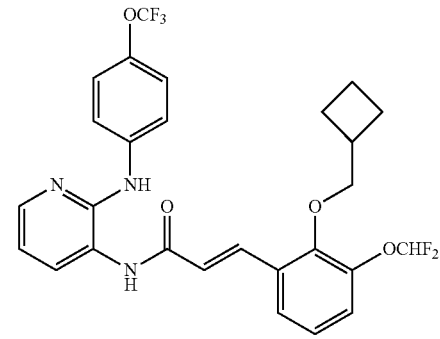 [SMILES: O=C(/C=C/c1cccc(OC(F)F)c1OCC1CCC1)Nc1cccnc1Nc1ccc(OC(F)(F)F)cc1] | |

The invention is illustrated by, but not limited to the following examples.

EXAMPLES

Example 1

2-{(E)-2-[2-(Cyclopropylmethoxy)-3-methoxyphenyl]vinyl}-1-pyridin-2-yl-1H-benzimidazole

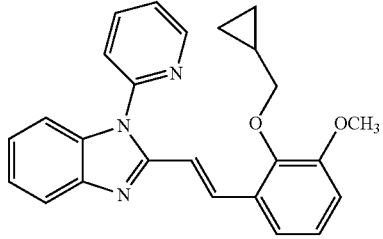 [SMILES: COc1cccc(/C=C/c2nc3ccccc3n2-c2ccccn2)c1OCC1CC1]

To a well stirred solution of Intermediate 5 (200 mg, 0.625 mmol) in dry DMA (3 ml) were added $Cs_2CO_3$ (407 mg, 1.250 mmol) and copper iodide (CuI; 24 mg, 0.125 mmol) followed by 2-iodopyridine (192 mg, 0.937 mmol) at room temperature. The reaction mixture was stirred at 130° C. under nitrogen for 5 h. After completion of the reaction, the reaction mixture was cooled to room temperature and diluted with water (10 ml) and extracted with ethyl acetate (2×10 ml). The combined organic layers were washed with water (2×30 ml), brine (30 ml) and dried over ($Na_2SO_4$). The crude product obtained after evaporation of the solvent under reduced pressure was purified by silica gel column chromatography using 20% ethyl acetate in petroleum ether to give 42 mg of the product as an off-white solid; $^1$H NMR (300 MHz, $CDCl_3$) δ 0.15-0.25 (m, 2H), 0.42-0.50 (m, 2H), 0.87 (br s, 1H), 3.78 (d, J=7.2 Hz, 2H), 3.83 (s, 3H), 6.85 (d, J=7.5 Hz, 1H), 7.00 (d, J=6.9 Hz, 1H), 7.05-7.12 (m, 1H), 7.30-7.50 (m, 6H), 7.82-7.88 (m, 1H), 7.97 (t, J=6.6 Hz, 1H), 8.20-8.30 (m, 1H), 8.70-8.80 (m, 1H); ESI-MS (m/z) 398.87 (M+H)$^+$.

Example 2

2-[(E)-2-(2-Cyclopentyloxy-3-methoxyphenyl)vinyl]-1-pyridin-2-yl-1H-benzimidazole

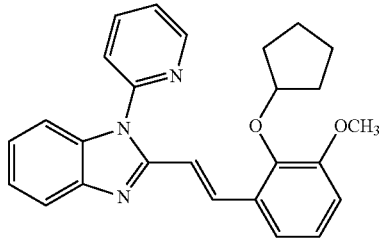 [SMILES: COc1cccc(/C=C/c2nc3ccccc3n2-c2ccccn2)c1OC1CCCC1]

This compound was prepared by coupling Intermediate 6 (300 mg, 0.898 mmol) with 2-bromopyridine (212 mg, 1.347 mmol) and $Cs_2CO_3$ (585 mg, 1.794 mmol) in presence of CuI (34 mg, 0.179 mmol) in dry DMA (5 ml) as described in Example 1 to give 104 mg of the product as an off-white solid; $^1$H NMR (300 MHz, $CDCl_3$) δ 1.61-1.75 (m, 8H), 3.83 (s, 3H), 4.82 (br s, 1H), 6.83 (d, J=7.8 Hz, 1H), 6.98 (t, J=7.8 Hz, 2H), 7.07 (d, J=7.5 Hz, 1H), 7.21-7.33 (m, 3H), 7.39-7.47 (m, 2H), 7.82 (d, J=7.8 Hz, 1H), 7.91-7.97 (m, 1H), 8.13 (d, J=16.2 Hz, 1H), 8.70-8.76 (m, 1H); APCI-MS (m/z) 412.27 (M+H)$^+$.

Example 3

1-(5-Chloropyridin-2-yl)-2-{(E)-2-[2-(cyclopentyloxy)-3-methoxyphenyl]vinyl}-1H-benzimidazole

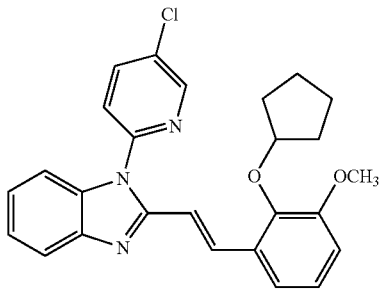

This compound was prepared by coupling Intermediate 6 (400 mg, 1.197 mmol) with 2,5-dichloropyridine (266 mg, 1.796 mmol) and $Cs_2CO_3$ (780 mg, 2.395 mmol) in presence of CuI (45 mg, 0.239 mmol) in dry DMA (5 ml) as described in Example 1 to give 214 mg of the product as an off-white solid; IR (KBr) 2964, 1574, 1471, 1287, 1017, 745 cm$^{-1}$; $^1$H NMR (300 MHz, $CDCl_3$) δ 1.70-1.80 (m, 8H), 3.84 (s, 3H), 4.85 (br s, 1H), 6.86 (d, J=6.9 Hz, 1H), 6.99 (t, J=8.4 Hz, 1H), 7.09 (d, J=7.5 Hz, 1H), 7.26-7.32 (m, 2H), 7.39-7.48 (m, 3H), 7.85 (d, J=7.8 Hz, 1H), 7.90 (d, J=8.1 Hz, 1H), 8.12 (d, J=15.0 Hz, 1H), 8.68 (s, 1H); APCI-MS (m/z) 446.27 (M+H)$^+$.

Example 4

2-[(E)-2-(2-[Cyclopentyloxy]-3-methoxyphenyl)vinyl]-1-(5-nitropyridin-2-yl)-1H-benzimidazole

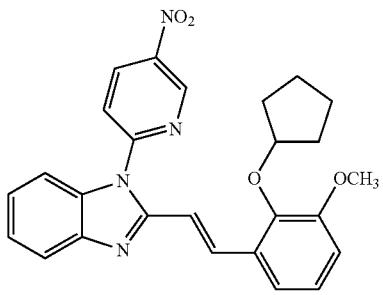 [SMILES: COc1cccc(/C=C/c2nc3ccccc3n2-c2ccc([N+](=O)[O-])cn2)c1OC1CCCC1]

The title compound was prepared by coupling Intermediate 6 (200 mg, 0.598 mmol) with 2-chloro-5-nitropyridine (189 mg, 0.898 mmol) in the presence of $Cs_2CO_3$ (390 mg, 1.197 mmol) and CuI (23 mg, 0.119 mmol) in dry DMA (3 ml) as described in Example 1 to give 80 mg of the product as an off-white solid; IR (KBr) 2959, 1601, 1525, 1465, 1265, 749 cm$^{-1}$; $^1$H NMR (300 MHz, $CDCl_3$) δ 1.70-1.80 (m, 8H), 3.86 (s, 3H), 4.88 (br s, 1H), 6.89 (d, J=7.2 Hz, 1H), 7.02 (t, J=7.8 Hz, 1H), 7.08-7.15 (m, 1H), 7.26-7.33 (m, 1H), 7.36-7.40 (m, 2H), 7.58 (d, J=7.8 Hz, 1H), 7.69 (d, J=8.4 Hz, 1H), 7.85 (d, J=8.1 Hz, 1H), 8.19 (d, J=15.9 Hz, 1H), 8.72 (dd, J=2.4, 8.7 Hz, 1H), 9.56 (s, 1H); APCI-MS (m/z) 457.17 (M+H)+.

Example 5

2-[(E)-2-(2-Benzyloxy-3-methoxyphenyl)vinyl]-1-(3,5-dichloropyridin-2-yl)-1H-benzimidazole

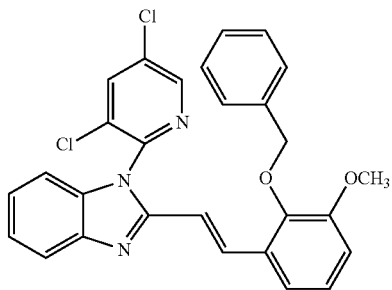 [SMILES: COc1cccc(/C=C/c2nc3ccccc3n2-c2ncc(Cl)cc2Cl)c1OCc1ccccc1]

The title compound was prepared by coupling Intermediate 7 (200 mg, 0.567 mmol) with 2,3,5-trichloropyridine (153 mg, 0.841 mmol) in presence of $Cs_2CO_3$ (365 mg, 1.189 mmol) and CuI (21 mg, 0.118 mmol) in dry DMA (5 ml) as described in Example 1 to give 109 mg of the product as an off-white solid; IR (KBr) 2934, 1601, 1454, 1268, 1070, 741 cm$^{-1}$; $^1$H NMR (300 MHz, CDCl$_3$) δ 3.83 (s, 3H), 4.92 (s, 2H), 6.80-6.88 (m, 1H), 6.96-7.04 (m, 4H), 7.12-7.20 (m, 1H), 7.27-7.36 (m, 6H), 7.75-7.83 (m, 2H), 7.89 (d, J=16.2 Hz, 1H), 8.33 (s, 1H); ESI-MS (m/z) 502.53 (M+H)+.

Example 6

1-(3,5-Dichloropyridin-2-yl)-2-{(E)-2-[2-(2-fluorobenzyloxy)-3-methoxyphenyl]vinyl}-1H-benzimidazole

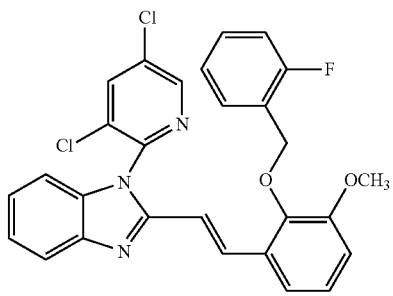 [SMILES: COc1cccc(/C=C/c2nc3ccccc3n2-c2ncc(Cl)cc2Cl)c1OCc1ccccc1F]

The title compound was prepared by coupling Intermediate 8 (200 mg, 0.574 mmol) with 2,3,5-trichloropyridine (156 mg, 0.862 mmol) in presence of $Cs_2CO_3$ (373 mg, 1.149 mmol) and CuI (28 mg, 0.149 mmol) in dry DMA (5 ml) as described in Example 1 to give 36 mg of the product as an off-white solid; $^1$H NMR (300 MHz, CDCl$_3$) δ 3.82 (s, 3H), 5.01 (s, 2H), 6.85-7.12 (m, 9H), 7.27-7.33 (m, 1H), 7.45 (t, J=6.0 Hz, 1H), 7.82 (s, 2H), 7.89 (d, J=15.9 Hz, 1H), 8.41 (s, 1H); ESI-MS (m/z) 521.32 (M+H)+.

Example 7

2-{2-[(E)-2-(2-Cyclopentyloxy-3-methoxyphenyl)vinyl]-1H-benzimidazol-1-yl}nicotinonitrile

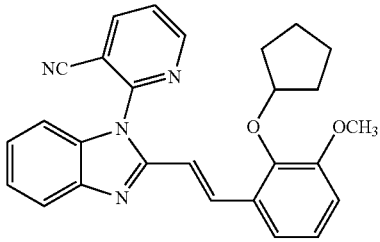 [SMILES: COc1cccc(/C=C/c2nc3ccccc3n2-c2ncccc2C#N)c1OC1CCCC1]

The title compound was prepared by coupling Intermediate 6 (200 mg, 0.598 mmol) with 2-chloronicotinonitrile (100 mg, 0.718 mmol) in presence of $Cs_2CO_3$ (390 mg, 1.198 mmol) and CuI (23 mg, 0.119 mmol) in dry DMA (3 ml) as described in Example 1 to give 82 mg of the product as an off-white solid; IR (KBr) 2936, 2233, 1628, 1580, 1455, 1266, 741 cm$^{-1}$; $^1$H NMR (300 MHz, CDCl$_3$) δ 1.68-1.80 (m, 8H), 3.84 (s, 3H), 4.80 (br s, 1H), 6.86 (d, J=7.8 Hz, 1H), 6.98-7.09 (m, 3H), 7.18 (d, J=7.8 Hz, 1H), 7.26-7.39 (m, 2H), 7.61-7.68 (m, 1H), 7.87 (d, J=7.8 Hz, 1H), 7.90 (d, J=15.9 Hz, 1H), 8.27 (d, J=6.3 Hz, 1H), 8.95 (s, 1H); APCI-MS (m/z) 437.50 (M+H)+.

Example 8

6-{2-[(E)-2-(2-Butoxy-3-methoxyphenyl)vinyl]-1H-benzimidazol-1-yl}nicotinonitrile

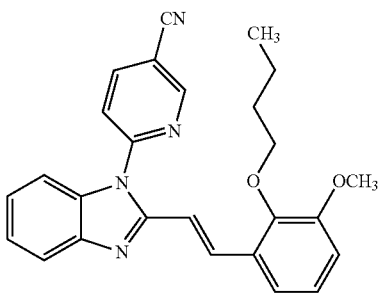 [SMILES: CCCCOc1c(/C=C/c2nc3ccccc3n2-c2ccc(C#N)cn2)cccc1OC]

The title compound was prepared by coupling Intermediate 2 (200 mg, 0.621 mmol) with 6-chloronicotinonitrile (129 mg, 0.931 mmol) in the presence of $Cs_2CO_3$ (405 mg, 1.243 mmol) and CuI (23 mg, 0.124 mmol) in dry DMA (5 ml) as described in Example 1 to give 97 mg of the product as an off-white solid; IR (KBr) 2957, 2229, 1591, 1475, 1266, 1073, 735 cm$^{-1}$; $^1$H NMR (300 MHz, CDCl$_3$) δ 0.92 (t, J=7.2 Hz, 3H), 1.35-1.47 (m, 2H), 1.63-1.73 (m, 2H), 3.85 (s, 3H), 3.96 (t, J=6.6 Hz, 2H), 6.87 (d, J=7.8 Hz, 1H), 6.99-7.09 (m, 2H), 7.28-7.38 (m, 3H), 7.52 (d, J=8.1 Hz, 1H), 7.62 (d, J=8.4 Hz, 1H), 7.83 (d, J=7.8 Hz, 1H), 8.13 (s, 1H), 8.19 (d, J=6.3 Hz, 1H), 8.98 (s, 1H); ESI-MS (m/z) 425.17 (M+H)+.

Example 9

6-{2-[(E)-2-(2-Isopropoxy-3-methoxyphenyl)vinyl]-1H-benzimidazol-1-yl}nicotinonitrile

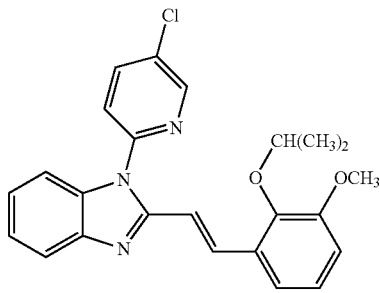 [SMILES: COc1cccc(/C=C/c2nc3ccccc3n2-c2ccc(Cl)cn2)c1OC(C)C]

The title compound was prepared by coupling Intermediate 1 (200 mg, 0.649 mmol) with 6-chloronicotinonitrile (135 mg, 0.973 mmol) in the presence of $Cs_2CO_3$ (423 mg, 1.298 mmol) and CuI (25 mg, 0.129 mmol) in dry DMA (4 ml) as described in Example 1 to give 30 mg of the product as an off-white solid; IR (KBr) 2977, 2233, 1590, 1461, 1286, 1083, 770 cm$^{-1}$; $^1$H NMR (300 MHz, CDCl$_3$) δ 1.28 (d, J=6.6 Hz, 6H), 3.84 (s, 3H), 4.50 (br s, 1H), 6.86 (d, J=7.8 Hz, 1H), 7.00 (t, J=7.8 Hz, 1H), 7.08 (d, J=7.2 Hz, 1H), 7.28-7.37 (m, 3H), 7.51 (d, J=8.4 Hz, 1H), 7.62 (d, J=8.1 Hz, 1H), 7.82 (d, J=7.8 Hz, 1H), 8.15 (d, J=16.2 Hz, 2H), 8.99 (s, 1H); ESI-MS (m/z) 411.28 (M+H)$^+$.

Example 10

6-{2-[(E)-2-(2-(1-Ethylpropoxy)-3-methoxyphenyl)vinyl]-1H-benzimidazol-1-yl}nicotinonitrile

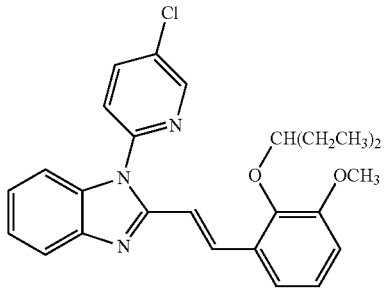

The title compound was prepared by coupling Intermediate 4 (200 mg, 0.645 mmol) with 6-chloronicotinonitrile (135 mg, 0.967 mmol) in the presence of $Cs_2CO_3$ (420 mg, 1.290 mmol) and CuI (24.57 mg, 0.129 mmol) in dry DMA (5 ml) as described in Example 1 to give 57 mg of the product as an off-white solid; IR (KBr) 2960, 2235, 1588, 1478, 1268, 1069, 737 cm$^{-1}$; $^1$H NMR (300 MHz, DMSO-d$_6$) δ 0.89 (t, J=6.3 Hz, 6H), 1.50-1.56 (m, 4H), 3.78 (s, 3H), 4.16 (br s, 1H), 7.01 (br s, 2H), 7.22-7.32 (m, 4H), 7.50 (d, J=6.3 Hz, 1H), 7.73 (d, J=6.9 Hz, 1H), 7.95 (d, J=7.5 Hz, 1H), 8.11 (d, J=16.2 Hz, 1H), 8.65 (d, J=7.8 Hz, 1H), 9.21 (s, 1H); APCI-MS (m/z) 439.20 (M+H)$^+$.

Example 11

6-(2-{(E)-2-[3-methoxy-2-(2-methylpropoxy)phenyl]ethenyl}-1H-benzimidazol-1-yl)pyridine-3-carbonitrile

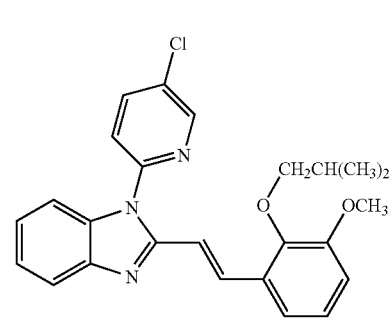

The title compound was prepared by coupling Intermediate 3 (200 mg, 0.675 mmol) with 6-chloronicotinonitrile (140 mg, 1.012 mmol) in the presence of $Cs_2CO_3$ (440 mg, 1.350 mmol) and CuI (25.71 mg, 0.135 mmol) in dry DMA (5 ml) as described in Example 1 to give 123 mg of the product as an off-white solid; IR (KBr) 2957, 2226, 1588, 1480, 1266, 1071, 747 cm$^{-1}$; $^1$H NMR (300 MHz, DMSO-d$_6$) δ 0.97 (d, J=6.9 Hz, 6H), 1.90-1.96 (m, 1H), 3.70 (d, J=6.3 Hz, 2H), 3.81 (s, 3H), 7.06 (s, 2H), 7.26-7.37 (m, 4H), 7.55 (d, J=7.5 Hz, 1H), 7.76 (d, J=7.8 Hz, 1H), 7.98 (d, J=8.1 Hz, 1H), 8.12 (d, J=16.2 Hz, 1H), 8.68 (d, J=7.8 Hz, 1H), 9.24 (s, 1H); APCI-MS (m/z) 425.28 (M+H)$^+$.

Example 12

6-{2-[(E)-2-(2-[Cyclopropylmethoxy]-3-methoxyphenyl)vinyl]-1H-benzimidazol-1-yl}nicotinonitrile

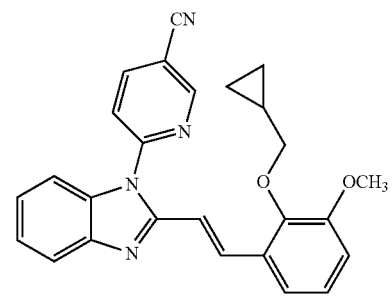 [SMILES: COc1cccc(/C=C/c2nc3ccccc3n2-c2ccc(C#N)cn2)c1OCC1CC1]

The title compound was prepared by coupling Intermediate 5 (200 mg, 0.625 mmol) with 6-chloronicotinonitrile (130 mg, 0.937 mmol) in the presence of $Cs_2CO_3$ (407 mg, 1.250 mmol) and CuI (24 mg, 0.125 mmol) in dry DMA (3 ml) as described in Example 1 to give 62 mg of the product as an off-white solid; IR (KBr) 2927, 2227, 1735, 1589, 1474, 1267, 980 cm$^{-1}$; $^1$H NMR (300 MHz, CDCl$_3$) δ 0.21 (d, J=4.8 Hz, 2H), 0.49 (d, J=7.5 Hz, 2H), 0.88 (br s, 1H), 3.81-3.88 (m, 5H), 6.89 (d, J=7.8 Hz, 1H), 7.02-7.12 (m, 2H), 7.30-7.40 (m, 3H), 7.57 (d, J=7.8 Hz, 1H), 7.68 (d, J=9 Hz, 1H), 7.88 (d, J=7.8 Hz, 1H), 8.23 (d, J=8.7 Hz, 2H), 9.02 (br s, 1H); ESI-MS (m/z) 423.27 (M+H)$^+$.

Example 13

6-{2-[(E)-2-(2-Cyclopentyloxy-3-methoxyphenyl)vinyl]-1H-benzimidazol-1-yl}nicotinonitrile

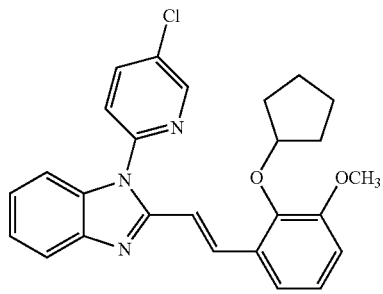 [SMILES: COc1cccc(/C=C/c2nc3ccccc3n2-c2ccc(Cl)cn2)c1OC1CCCC1]

The title compound was prepared by coupling Intermediate 6 (200 mg, 0.598 mmol) with 6-chloronicotinitrile (124 mg, 0.898 mmol) in the presence of $Cs_2CO_3$ (390 mg, 1.196 mmol) and CuI (23 mg, 0.119 mmol) in dry DMA (5 ml) as described in Example 1 to give 43 mg of the product as an off-white solid; $^1$H NMR (300 MHz, CDCl$_3$) δ 1.50-1.57 (m, 2H), 1.64-1.70 (m, 2H), 1.76-1.83 (m, 4H), 3.86 (s, 3H), 4.89 (br s, 1H), 6.89 (d, J=6.3 Hz, 1H), 6.98-7.04 (m, 1H), 7.10 (d, J=7.2 Hz, 1H), 7.24-7.29 (m, 1H), 7.31 (d, J=15.3 Hz, 1H), 7.34-7.42 (m, 1H), 7.54 (d, J=6.0 Hz, 1H), 7.64 (d, J=6.3 Hz, 1H), 7.84 (d, J=6.0 Hz, 1H), 8.15 (s, 1H), 8.20 (d, J=8.1 Hz, 1H), 9.00-9.07 (m, 1H); ESI-MS (m/z) 437.35 (M+H)$^+$.

Example 14

6-(2-{(E)-2-[2-(2-Fluorobenzyloxy)-3-methoxyphenyl]vinyl}-1H-benzimidazol-1-yl)nicotinonitrile

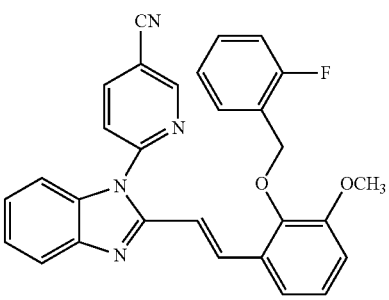 [SMILES: COc1cccc(/C=C/c2nc3ccccc3n2-c2ccc(C#N)cn2)c1OCc1ccccc1F]

The title compound was prepared by coupling Intermediate 8 (200 mg, 0.574 mmol) with 6-chloronicotinitrile (118 mg, 0.862 mmol) in the presence of $Cs_2CO_3$ (373 mg, 1.149 mmol) and CuI (28 mg, 0.149 mmol) in dry DMA (5 ml) as described in Example 1 to give 32 mg of the product as an off-white solid; $^1$H NMR (300 MHz, CDCl$_3$) δ 3.87 (s, 3H), 5.06 (s, 2H), 6.89-7.00 (m, 2H), 7.06-7.12 (m, 3H), 7.27-7.39 (m, 3H), 7.46-7.55 (m, 4H), 7.80 (d, J=7.8 Hz, 1H), 7.96-8.06 (m, 2H), 8.80 (s, 1H); ESI-MS (m/z) 477.53 (M+H)$^+$.

Example 15

6-{2-[(E)-2-(2-(2-Cyanobenzyloxy-3-methoxyphenyl)vinyl]-1H-benzimidazol-1-yl}nicotinonitrile

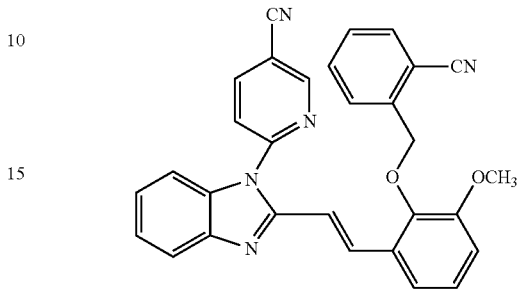

The title compound was prepared by coupling Intermediate 9 (200 mg, 0.524 mmol) with 6-chloronicotinonitrile (109.20 mg, 0.787 mmol) in the presence of $Cs_2CO_3$ (342.5 mg, 1.048 mmol) and CuI (20 mg, 0.104 mmol) in dry DMA (5 ml) as described in Example 1 to give 83 mg of the product as an off-white solid; IR (KBr) 2937, 2233, 1592, 1476, 1389, 1268, 1072 cm$^{-1}$; $^1$H NMR (300 MHz, CDCl$_3$) δ 3.83 (s, 3H), 5.20 (s, 2H), 7.11-7.15 (m, 2H), 7.23-7.35 (m, 4H), 7.52-7.58 (m, 2H), 7.72-7.83 (m, 4H), 7.91 (d, J=8.4 Hz, 1H), 8.00 (d, J=16.2 Hz, 1H), 8.61 (d, J=8.1 Hz, 1H), 9.16 (s, 1H); APCI-MS (m/z) 484.13 (M+H)$^+$.

Example 16

6-{2-[(E)-2-(3-Methoxy-2-{[2-(trifluoromethyl)benzyl]oxy}phenyl)vinyl]-1H-benzimidazole-1-yl}nicotinonitrile

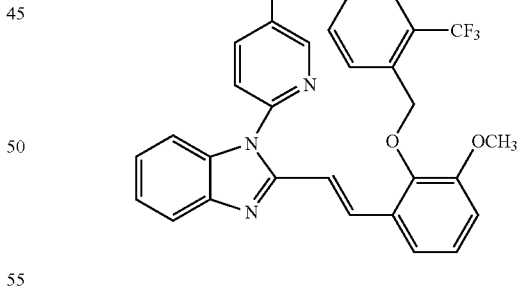

The title compound was prepared by coupling Intermediate 10 (200 mg, 0.471 mmol) with 6-chloronicotinonitrile (98 mg, 0.707 mmol) in the presence of $Cs_2CO_3$ (308 mg, 0.943 mmol) and CuI (17.96 mg, 0.094 mmol) in dry DMA (5 ml) as described in Example 1 to give 109 mg of the product as an off-white solid; IR (KBr) 2944, 2234, 1591, 1479, 1315, 1094, 744 cm$^{-1}$; $^1$H NMR (300 MHz, DMSO-d$_6$) δ 3.83 (br s, 3H), 5.14 (s, 2H), 7.14 (d, J=6.3 Hz, 2H), 7.27-7.37 (m, 5H), 7.53-7.59 (m, 2H), 7.74 (d, J=7.2 Hz, 2H), 7.89 (d, J=8.1 Hz, 2H), 8.06 (d, J=15.6 Hz, 1H), 8.57 (d, J=8.4 Hz, 1H), 9.10 (s, 1H); APCI-MS (m/z) 527.22 (M+H)$^+$.

Example 17

6-(2-{(E)-2-[2-(2,6-Difluorobenzyloxy)-3-methoxyphenyl]vinyl}-1H-benzimidazol-1-yl)nicotinonitrile

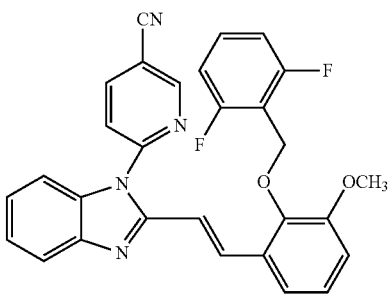 [SMILES: COc1cccc(/C=C/c2nc3ccccc3n2-c2ccc(C#N)cn2)c1OCc1c(F)cccc1F]

The title compound was prepared by coupling Intermediate 11 (201 mg, 0.509 mmol) with 6-chloronicotinonitrile (106 mg, 0.764 mmol) in the presence of $Cs_2CO_3$ (333 mg, 1.019 mmol) and CuI (20 mg, 0.101 mmol) in dry DMA (5 ml) as described in Example 1 to give 86 mg of the product as an off-white solid; IR (KBr) 2968, 2231, 1591, 1471, 1388, 1264, 1060, 728 cm$^{-1}$; $^1$H NMR (300 MHz, CDCl$_3$) δ 3.84 (s, 3H), 5.11 (s, 2H), 7.00 (t, J=7.8 Hz, 2H), 7.05-7.12 (m, 2H), 7.17-7.22 (m, 2H), 7.28-7.41 (m, 3H), 7.57 (d, J=8.4 Hz, 1H), 7.76 (d, J=7.2 Hz, 1H), 7.90 (d, J=8.7 Hz, 1H), 7.97 (d, J=15.9 Hz, 1H), 8.65 (dd, J=1.8, 8.4 Hz, 1H), 9.20 (s, 1H); APCI-MS (m/z) 495.12 (M+H)$^+$.

Example 18

6-(2-{(E)-2-[2-(2,4-Difluorobenzyloxy)-3-methoxyphenyl]vinyl}-1H-benzimidazol-1-yl)nicotinonitrile

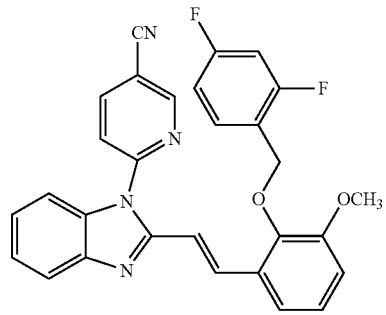 [SMILES: COc1cccc(/C=C/c2nc3ccccc3n2-c2ccc(C#N)cn2)c1OCc1ccc(F)cc1F]

The title compound was prepared by coupling Intermediate 12 (200 mg, 0.52 mmol) with 6-chloronicotinonitrile (110 mg, 0.79 mmol) in the presence of $Cs_2CO_3$ (345 mg, 1.05 mmol) and CuI (20 mg, 0.10 mmol) in dry DMA (5 ml) as described in Example 1 to give 95 mg of the product as an off-white solid; IR (KBr) 2940, 2231, 1589, 1478, 1387, 1269, 1072, 740 cm$^{-1}$; $^1$H NMR (300 MHz, DMSO-d$_6$) δ 3.85 (s, 3H), 5.04 (s, 2H), 7.04-7.13 (m, 3H), 7.16-7.25 (m, 3H), 7.28-7.38 (m, 2H), 7.49-7.57 (m, 2H), 7.77 (d, J=7.5 Hz, 1H), 7.92 (d, J=8.7 Hz, 1H), 8.01 (d, J=15.9 Hz, 1H), 8.63 (d, J=8.4 Hz, 1H), 9.18 (s, 1H); ESI-MS (m/z) 495.01 (M+H)$^+$.

Example 19

Ethyl 6-{2-[(E)-2-(2-[Cyclopentyloxy]-3-methoxyphenyl)vinyl]-1H-benzimidazol-1-yl}pyridazine-3-carboxylate

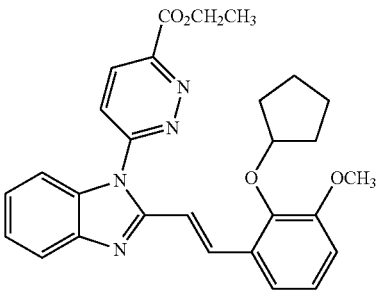

The title compound was prepared by coupling Intermediate 6 (200 mg, 0.598 mmol) with ethyl 6-chloropyridazine-3-carboxylate (168 mg, 0.898 mmol) in the presence of $Cs_2CO_3$ (890 mg, 1.19 mmol) and CuI (23 mg, 0.119 mmol) in dry DMA (5 ml) as described in Example 1. The crude product obtained after evaporation of the solvent under reduced pressure was purified by silica gel column chromatography using 12% acetone in petroleum ether to give 52 mg of the product as an off-white solid; IR (KBr) 2959, 1711, 1621, 1575, 1455, 1268, 1150 cm$^{-1}$; $^1$H NMR (300 MHz, CDCl$_3$) δ 1.60-1.70 (m, 8H), 1.78-1.85 (m, 5H), 3.86 (s, 3H), 4.87 (br s, 1H), 6.89 (d, J=7.8 Hz, 1H), 7.01 (d, J=7.8 Hz, 1H), 7.13 (d, J=7.2 Hz, 1H), 7.26-7.42 (m, 3H), 7.59 (d, J=7.8 Hz, 1H), 7.86 (t, J=8.1 Hz, 2H), 8.24 (d, J=15.9 Hz, 1H), 8.44 (d, J=8.7 Hz, 1H); APCI-MS (m/z) 485.48 (M+H)$^+$.

Example 20

6-{2-[(E)-2-(2-[Cyclopentyloxy]-3-methoxyphenyl)vinyl]-1H-benzimidazol-1-yl}pyridazine-3-carbonitrile

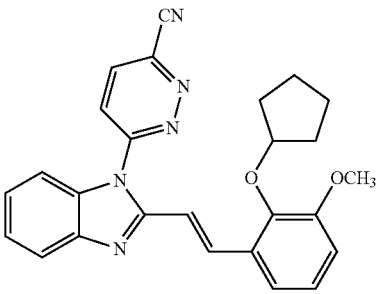 [SMILES: COc1cccc(/C=C/c2nc3ccccc3n2-c2ccc(C#N)nn2)c1OC1CCCC1]

Step 1: (6-{2-[(E)-2-(2-[Cyclopentyloxy]-3-methoxyphenyl)vinyl]-1H-benzimidazol-1-yl}pyridazin-3-yl)carboxylic acid: This compound was prepared by adding aqueous solution of lithium hydroxide (35 mg, 0.826 mmol) to a stirred solution of Example 19 that is Ethyl 6-{2-[(E)-2-(2-[Cyclopentyloxy]-3-methoxyphenyl)vinyl]-1H-benzimidazol-1-yl}pyridazine-3-carboxylate (200 mg, 0.413 mmol) in ethanol (5 ml) and stirring the reaction mixture at room temperature for 2 h. After completion of reaction the reaction mixture was acidified with 10% HCl until pH 4 was reached and at this pH the product precipitated out as a yellow solid which was filtered, washed with diethylether and dried under vaccum to get 210 mg of off-white solid.

Step 2: 6-{2-[(E)-2-(2-[Cyclopentyloxy]-3-methoxyphenyl)vinyl]-1H-benzimidazol-1-yl}pyridazine-3-carboxamide: This compound was prepared by adding triethylamine (66.44 mg, 0.657 mmol) to the stirred solution of Step 1 product (200 mg, 0.43 mmol) in dry THF (5 ml) under nitrogen atmosphere. Ethyl chloroformate (71.40 mg, 0.657 mmol) was added to the reaction mixture which was cooled to −10° C., after a time interval of 30 minutes aqueous ammonia (2 ml, 25%) was added and the reaction mixture was stirred for 30 minutes. Reaction mixture was quenched with water to get off-white solid which was filtered, washed with diethylether and dried under vaccum to get 131 mg of yellow solid.

Step 3: The final compound was prepared by adding triethylamne (80.0 mg, 0.78 mmol) to a stirred solution of Step 2 product (121 mg, 0.263 mmol) dissolved in dry DCM (5 ml) follwed by addition of triflouroacetic anhydride (84 mg, 0.395 mmol) at 0° C., under nitrogen atmosphere and the reaction mixture stirred for 1 h. The reaction mixture was then extracted with $CHCl_3$ and the combined organic layers washed with water, brine, dried ($Na_2SO_4$), filtered and concentrated under vaccum. The crude product was purified by silica gel column chromatography using 2% acetone in chloroform to give 79 mg of the product of off-white solid; IR (KBr) 2959, 2243, 1573, 1455, 1263, 743 cm$^{-1}$; $^1$H NMR (300 MHz, DMSO-d$_6$) δ 1.62-1.68 (m, 4H), 1.78-1.89 (m, 4H), 3.86 (s, 3H), 4.89 (br s, 1H), 6.90 (d, J=7.8 Hz, 1H), 7.03 (t, J=7.8 Hz, 1H), 7.11 (d, J=7.8 Hz, 1H), 7.23-7.28 (m, 1H), 7.35-7.44 (m, 2H), 7.59 (d, J=7.8 Hz, 1H), 7.87 (d, J=9.3 Hz, 2H), 8.06 (d, J=9.0 Hz, 1H), 8.19 (d, J=15.9 Hz,1H); APCI-MS (m/z) 438.21 (M+H)$^+$.

Example 21

2-{(E)-2-[2-Cyclopentyloxy)-3-methoxyphenyl]vinyl}benzimidazole

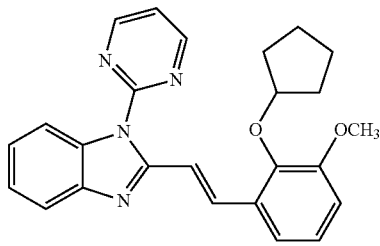 [SMILES: COc1cccc(/C=C/c2nc3ccccc3n2-c2ncccn2)c1OC1CCCC1]

The title compound was prepared by coupling Intermediate 6 (200 mg, 0.598 mmol) with 2-chloropyrimidine (103 mg, 0.898 mmol) in the presence of $Cs_2CO_3$ (391 mg, 1.197 mmol) and CuI (23 mg, 0.119 mmol) in dry DMA (5 ml) as described in Example 1 to give 73 mg of the product as an off-white solid; IR (KBr) 2950, 1568, 1421, 1266, 1065 cm$^{-1}$; $^1$H NMR (300 MHz, CDCl$_3$) δ 1.67-1.73 (m, 4H), 1.76-1.88 (m, 4H), 3.87 (s, 3H), 4.88 (br s, 1H), 6.88 (d, J=7.8 Hz, 1H), 7.04 (t, J=7.8 Hz, 1H), 7.21 (s, 1H), 7.32-7.36 (m, 3H), 7.83 (d, J=6.6 Hz, 1H), 8.02 (d, J=16.2 Hz, 1H), 8.16 (d, J=7.8 Hz, 1H), 8.25 (d, J=15.6 Hz, 1H), 8.92 (d, J=4.2 Hz, 1H); ESI-MS (m/z) 413.19 (M+H)$^+$.

Example 22

1-(5-Bromopyrimidin-2-yl)-2-{(E)-2-[2-(1-ethylpropoxy)-3-methoxyphenyl]vinyl}-1H-benzimidazole

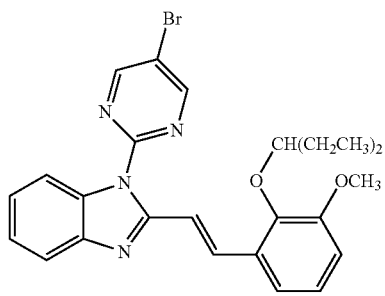

The title compound was prepared by coupling Intermediate 4 (500 mg, 1.492 mmol) with 5-bromo-2-chlororpyrimidine (434 mg, 2.238 mmol) in the presence of $Cs_2CO_3$ (973 mg, 2.985 mmol) and CuI (57 mg, 0.298 mmol) in dry DMA (10 ml) as described in Example 1 to give 380 mg of the product as an off-white solid; IR (KBr) 2922, 1560, 1417, 1259, 1088, 746 cm$^{-1}$; $^1$H NMR (300 MHz, CDCl$_3$) δ 0.95 (d, J=7.2 Hz, 6H), 1.63-1.69 (m, 4H), 3.85 (s, 3H), 4.20 (br s, 1H), 6.87 (d, J=8.1 Hz, 1H), 7.03 (t, J=7.8 Hz, 1H), 7.20-7.26 (m, 1H), 7.31-7.37 (m, 2H), 7.81 (d, J=7.5 Hz, 1H), 7.94 (d, J=7.8 Hz, 1H), 8.12 (d, J=7.8 Hz, 1H), 8.27 (d, J=15.9 Hz, 1H), 8.93 (s, 2H); APCI-MS (m/z) 493.41 (M)$^+$.

Example 23

1-(5-Bromopyrimidin-2-yl)-2-[(E)-2-(2-cyclopentyloxy-3-methoxyphenyl)vinyl]-1H-benzimidazole

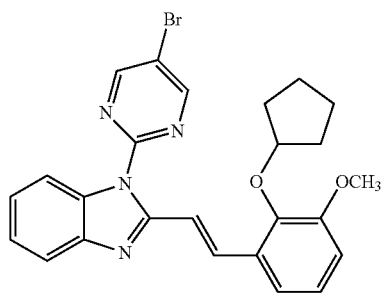

The title compound was prepared by coupling Intermediate 6 (200 mg, 0.598 mmol) with 5-bromo-2-chlororpyrimidine (174 mg, 0.898 mmol) in the presence of $Cs_2CO_3$ (391 mg, 1.197 mmol) and CuI (23 mg, 0.119 mmol) in dry DMA (5 ml) as described in Example 1. The crude product was purified by silica gel column chromatography using 12% Ethyl acetate in petroleum ether to give 175 mg of the product as an off-white solid; IR (KBr) 2957, 2233, 1589, 1477, 1267, 1068, 738 cm$^{-1}$; $^1$H NMR (300 MHz, CDCl$_3$) δ 1.60-1.70 (m, 4H), 1.89-1.96 (m, 4H), 3.87 (s, 3H), 4.87 (br s, 1H), 6.88 (d, J=8.1 Hz, 1H), 7.04 (t, J=7.8 Hz, 1H), 7.20-7.26 (m, 1H), 7.29-7.39 (m, 2H), 7.82 (d, J=7.5 Hz, 1H), 7.96 (d, J=15.9 Hz, 1H), 8.12 (d, J=8.4 Hz, 1H), 8.24 (d, J=16.2 Hz, 1H), 8.93 (s, 2H); APCI-MS (m/z) 491.41 (M)$^+$.

Example 24

2-[(E)-2-(2-Cyclopentyloxy-3-methoxyphenyl)vinyl]-1-[3-(trifluoromethyl)pyridin-2-yl]-1H-benzimidazole

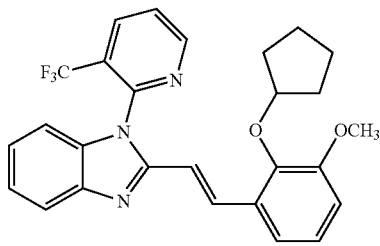

The title compound was prepared by coupling Intermediate 6 (200 mg, 0.598 mmol) with 2-chloro-3-(trifluoromethyl)pyridine (163 mg, 0.898 mmol) in presence of $Cs_2CO_3$ (390 mg, 1.197 mmol) and CuI (23 mg, 0.119 mmol) in dry DMA (5 ml) as described in Example 1 to give 83 mg of the product as an off-white solid; IR (KBr) 2959, 1591, 1456, 1267, 1031, 741 cm$^{-1}$; $^1$H NMR (300 MHz, CDCl$_3$) δ 1.50-1.75 (m, 8H), 3.81 (s, 3H), 4.89 (br s, 1H), 6.63 (d, J=15.0 Hz, 1H), 6.79-6.89 (m, 2H), 6.95 (d, J=6.3 Hz, 2H), 7.12-7.18 (m, 1H), 7.29 (t, J=6.3 Hz, 1H), 7.55-7.65 (m, 1H), 7.79 (d, J=7.5 Hz, 1H), 7.86 (d, J=15.3 Hz, 1H), 8.24 (d, J=6.0 Hz, 1H), 8.88-8.93 (m, 1H); ESI-MS (m/z) 480.51 (M+H)$^+$.

Example 25

2-[(E)-2-(2-Isopropoxy-3-methoxyphenyl)vinyl]-1-(5-trifluoromethylpyridin-2-yl)-1H-benzimidazole

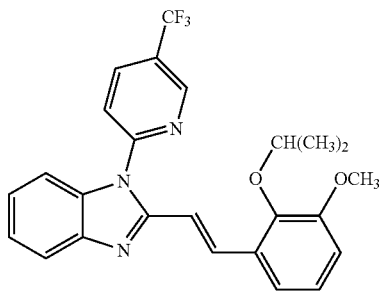

The title compound was prepared by coupling Intermediate 1 (200 mg, 0.649 mmol) with 2-chloro-5-(trifluoromethyl)pyridine (177 mg, 0.972 mmol) in presence of $Cs_2CO_3$ (418 mg, 1.282 mmol) and CuI (25 mg, 0.129 mmol) in dry DMA (5 ml) as described in Example 1 to give 43 mg of the product as an off-white solid; IR (KBr) 2976, 1603, 1464, 1325, 1130, 1080, 740 cm$^{-1}$; $^1$H NMR (300 MHz, CDCl$_3$) δ 1.23 (d, J=6.3 Hz, 6H), 3.83 (s, 3H), 4.49 (br s, 1H), 6.85 (d, J=7.8 Hz, 1H), 7.00 (t, J=8.4 Hz, 1H), 7.08 (d, J=7.8 Hz, 1H), 7.26-7.35 (m, 3H), 7.47 (d, J=8.4 Hz, 1H), 7.62 (d, J=8.4 Hz, 1H), 7.82 (d, J=7.8 Hz, 1H), 8.14 (d, J=15.9 Hz, 2H), 8.99 (s, 1H); ESI-MS (m/z) 454.20 (M+H)$^+$.

Example 26

2-[(E)-2-(2-Cyclopropyloxy-3-methoxyphenyl)vinyl]-1-(5-trifluoromethylpyridin-2-yl)-1H-benzimidazole

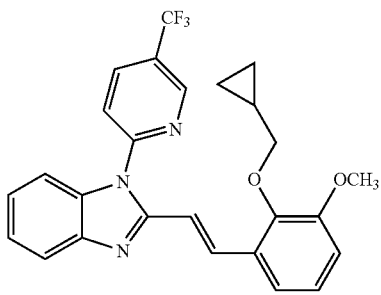

The title compound was prepared by coupling Intermediate 5 (170 mg, 0.531 mmol) with 2-chloro-5-trifluoromethylpyridine (145 mg, 0.796 mmol) in presence of $Cs_2CO_3$ (346 mg, 1.062 mmol) and CuI (20 mg, 0.106 mmol) in dry DMA (5 ml) as described in Example 1 to give 98 mg of the product as an off-white solid; IR (Neat) 2943, 1601, 1451, 1269, 1125, 1080, 988 cm$^{-1}$; $^1$H NMR (300 MHz, CDCl$_3$) δ 0.18-0.26 (m, 2H), 0.44-0.52 (m, 2H), 1.15 (br s, 1H), 3.81 (d, J=5.4 Hz, 2H), 3.85 (s, 3H), 6.87 (d, J=6.3 Hz, 1H), 7.03 (t, J=6.0 Hz, 1H), 7.10 (d, J=6.0 Hz, 1H), 7.26-7.31 (m, 1H), 7.36-7.44 (m, 2H), 7.53 (d, J=6.0 Hz, 1H), 7.65 (d, J=6.3 Hz, 1H), 7.85 (d, J=6.0 Hz, 1H), 8.15-8.24 (m, 2H), 9.02 (s, 1H); ESI-MS (m/z) 466.18 (M+H)$^+$.

Example 27

2-[(E)-2-(2-Cyclopentyloxy-3-methoxyphenyl)vinyl]-1-[5-(trifluoromethyl)pyridin-2-yl]-1H-benzimidazole

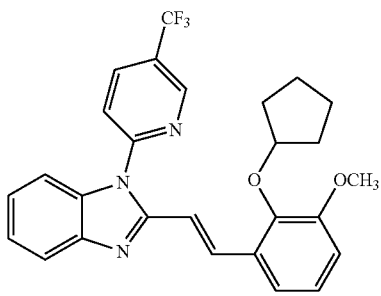

The title compound was prepared by coupling Intermediate 6 (200 mg, 0.598 mmol) with 2-chloro-5-(trifluoromethyl)pyridine (217 mg, 1.196 mmol) in presence of $Cs_2CO_3$ (389 mg, 1.196 mmol) and CuI (22 mg, 0.119 mmol) in dry DMA (5 ml) as described in Example 1 to give 110 mg of the product as an off-white solid; IR (KBr) 2951, 1605, 1474, 1325, 1133, 735 cm$^{-1}$; $^1$H NMR (300 MHz, CDCl$_3$) δ 1.15-1.25 (m, 4H), 1.35-1.42 (m, 4H), 3.78 (s, 3H), 4.48 (br s, 1H), 6.90-7.04 (m, 3H), 7.15-7.23 (m, 2H), 7.32-7.42 (m, 3H), 7.76-7.88 (m, 3H), 8.81 (s, 1H); ESI-MS (m/z) 454.10 (M+H)$^+$.

Example 28

2-[(E)-2-(2-Benzyloxy-3-methoxyphenyl)vinyl]-1-[5-(trifluoromethyl)pyridin-2-yl]-1H-benzimidazole

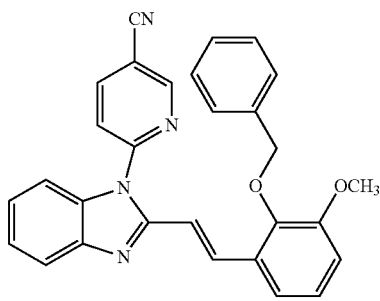 [SMILES: COc1cccc(/C=C/c2nc3ccccc3n2-c2ccc(C#N)cn2)c1OCc1ccccc1]

The title compound was prepared by coupling Intermediate 7 (500 mg, 1.404 mmol) with 2-chloro-5-(trifluoromethyl)pyridine (382 mg, 2.106 mmol) in presence of $Cs_2CO_3$ (914 mg, 2.808 mmol) and CuI (53 mg, 0.208 mmol) in dry DMA (5 ml) as described in Example 1 to give 507 mg of the product as an off-white solid; $^1$H NMR (300 MHz, $CDCl_3$) δ 3.87 (s, 3H), 4.98 (m, 2H), 6.89 (d, J=7.5 Hz, 1H), 7.00-7.10 (m, 2H), 7.20-7.28 (m, 4H), 7.34-7.45 (m, 5H), 7.49 (d, J=7.8 Hz, 1H), 7.83 (d, J=7.8 Hz, 1H), 7.92 (d, J=8.1 Hz, 1H), 8.14 (d, J=15.6 Hz, 1H), 8.79 (s, 1H); ESI-MS (m/z) 502.35 (M+H)$^+$.

Example 29

1-[3-Chloro-5-(trifluoromethyl)pyridin-2-yl]-2-[(E)-2-(2-cyclopentyloxy-3-methoxyphenyl)vinyl]-1H-benzimidazole

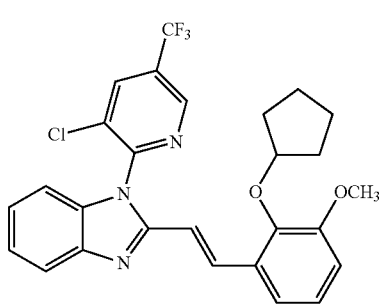 [SMILES: COc1cccc(/C=C/c2nc3ccccc3n2-c2ncc(C(F)(F)F)cc2Cl)c1OC1CCCC1]

The title compound was prepared by coupling Intermediate 6 (250 mg, 0.748 mmol) with 2,3-dichloro-5-(trifluoromethyl)pyridine (243 mg, 1.122 mmol) in the presence of $Cs_2CO_3$ (488 mg, 1.49 mmol) and CuI (29 mg, 0.149 mmol) in dry DMA (5 ml) as described in Example 1 to give 61.2 mg of the product as an off-white solid; IR (KBr) 2960, 1628, 1577, 1466, 1267, 741 cm$^{-1}$; $^1$H NMR (300 MHz, $CDCl_3$) δ 1.60-1.81 (m, 8H), 3.84 (s, 3H), 4.82 (br s, 1H), 6.85-6.91 (m, 2H), 6.96-7.06 (m, 3H), 7.28-7.35 (m, 1H), 7.86 (d, J=7.8 Hz, 1H), 7.90-7.96 (m, 1H), 8.02 (d, J=15.6 Hz, 1H), 8.23-8.28 (m, 1H), 8.91 (s, 1H); ESI-MS (m/z) 514.33 (M+H)$^+$.

Example 30

Methyl 6-(2-{(E)-2-[2-(Cyclopentyloxy)-3-methoxyphenyl]vinyl}-1H-benzimidazol-1-yl)nicotinate

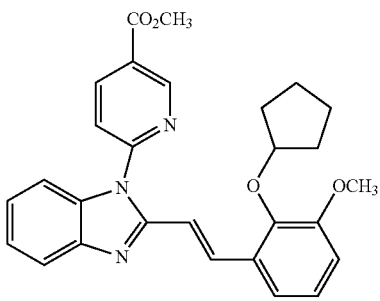 [SMILES: COC(=O)c1ccc(-n2c(/C=C/c3cccc(OC)c3OC3CCCC3)nc3ccccc32)nc1]

The title compound was prepared by coupling Intermediate 6 (200 mg, 0.59 mmol) with methyl 6-chloronicotinate (154 mg, 0.89 mmol) in the presence of $Cs_2CO_3$ (390 mg, 1.19 mmol) and CuI (23 mg, 0.11 mmol) in dry DMA (5 ml) as described in Example 1 to give 50 mg of the product as an off-white solid; IR (KBr) 2952, 1575, 1456, 1263, 1071, 740 cm$^{-1}$; $^1$H NMR (300 MHz, $CDCl_3$) δ 1.67-1.73 (m, 3H), 1.85-1.95 (m, 5H), 3.88 (s, 6H), 4.88-4.93 (m, 1H), 6.90 (d, J=8.1 Hz, 1H), 7.06 (t, J=7.8 Hz, 1H), 7.21 (d, J=7.8 Hz, 1H), 7.27-7.35 (m, 6H), 7.77 (d, J=6.3 Hz, 1H), 8.10 (d, J=16.2 Hz, 1H); ESI-MS (m/z) 470.23 (M+H)$^+$.

Example 31

2-[(E)-2-(2-Cyclopropylmethoxy-3-methoxyphenyl)vinyl]-1-(4-methylphenyl)-1H-benzimidazole

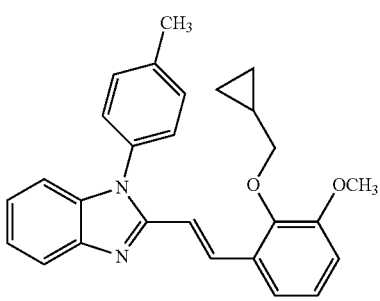

The title compound was prepared by coupling Intermediate 5 (200 mg, 0.625 mmol) with 4-iodotoluene (205 mg, 0.937 mmol) and $Cs_2CO_3$ (407 mg, 1.252 mmol) in presence of CuI (24 mg, 0.124 mmol) in dry DMA (3 ml) as described in Example 1 to give 45 mg of the product as an off-white solid; IR (Neat) 2926, 1631, 1515, 1476, 1267, 985, 742 cm$^{-1}$; $^1$H NMR (300 MHz, $CDCl_3$) δ 0.16-0.21 (m, 2H), 0.44-0.49 (m, 2H), 1.10 (br s, 1H), 2.46 (s, 3H), 3.75 (d, J=5.4 Hz, 2H), 3.83 (s, 3H), 6.83 (d, J=7.2 Hz, 1H), 6.99 (t, J=6.0 Hz, 2H), 7.05 (d, J=5.1 Hz, 2H), 7.13 (d, J=6.6 Hz, 1H), 7.25-7.32 (m, 3H), 7.38 (d, J=6.0 Hz, 2H), 7.85 (d, J=6.0 Hz, 1H), 8.17 (d, J=12.0 Hz, 1H); APCI-MS (m/z) 411.37 (M+H)$^+$.

Example 32

2-[(E)-2-(2-Cyclopentyloxy-3-methoxyphenyl)vinyl]-1-(2-methoxyphenyl)-1H-benzimidazole

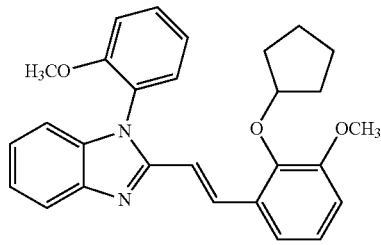

The title compound was prepared by coupling Intermediate 6 (200 mg, 0.598 mmol) with 2-iodoanisole (280 mg, 1.197 mmol) and $Cs_2CO_3$ (390 mg, 1.197 mmol) in presence of CuI (23 mg, 0.119 mmol) in dry DMA (5 ml) as described in Example 1 to give 31 mg of the product as an off-white solid; IR (KBr) 3377, 2952, 1575, 1474, 1265, 1072, 747 $cm^{-1}$; $^1$H NMR (300 MHz, $CDCl_3$) δ 1.59-1.70 (m, 4H), 1.80-1.94 (m, 4H), 3.86 (s, 6H), 4.89 (br s, 1H), 6.85-6.91 (m, 1H), 7.00-7.07 (m, 1H), 7.12-7.20 (m, 3H), 7.28-7.38 (m, 6H), 7.75 (s, 1H), 8.07 (d, J=16.5 Hz, 1H); ESI-MS (m/z) 441.20 $(M+H)^+$.

Example 33

4-{2-[(E)-2-(2-Cyclopropylmethoxy-3-methoxyphenyl)vinyl]-1H-benzimidazol-1-yl}benzonitrile

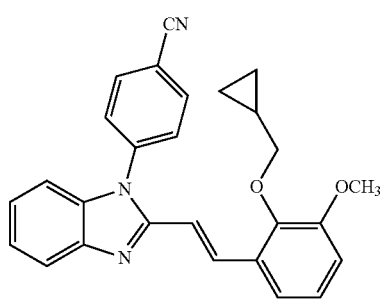

The title compound was prepared by coupling Intermediate 5 (200 mg, 0.625 mmol) with 4-iodobenzonitrile (322 mg, 1.562 mmol) in presence of $Cs_2CO_3$ (407 mg, 1.252 mmol) and CuI (24 mg, 0.124 mmol) in dry DMA (5 ml) as described in Example 1 to give 54 mg of the product as an off-white solid; IR (KBr) 3412, 2926, 2233, 1626, 1508, 1308, 1267, 1070, 751 $cm^{-1}$; $^1$H NMR (300 MHz, $CDCl_3$) δ 0.14-0.20 (m, 2H), 0.42-0.50 (m, 2H), 1.02 (br s, 1H), 3.69-3.77 (m, 2H), 3.83 (s, 3H), 6.90-6.96 (m, 1H), 7.00-7.07 (m, 1H), 7.15-7.21 (m, 2H), 7.35-7.42 (m, 3H), 7.45-7.52 (m, 2H), 7.65-7.73 (m, 2H), 7.95-8.08 (m, 1H), 8.75 (br s, 1H); APCI-MS (m/z) 422.19 $(M+H)^+$.

Example 34

4-{2-[(E)-2-(2-Benzyloxy-3-methoxyphenyl)vinyl]-1H-benzimidazol-1-yl}benzonitrile

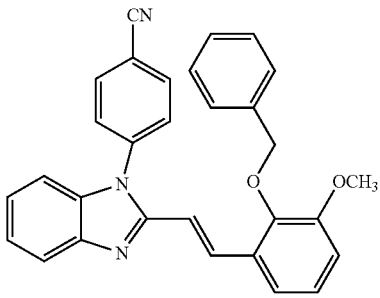

The title compound was prepared by coupling Intermediate 7 (200 mg, 0.567 mmol) with 4-iodobenzonitrile (193 mg, 0.841 mmol) in presence of $Cs_2CO_3$ (183 mg, 0.567 mmol) and CuI (21 mg, 0.118 mmol) in dry DMA (5 ml) as described in Example 1 to give 37 mg of the product as an off-white solid; IR (KBr) 2935, 2229, 1603, 1450, 1268, 742 $cm^{-1}$; $^1$H NMR (300 MHz, $CDCl_3$) δ 3.86 (s, 3H), 4.94 (s, 2H), 6.85-6.92 (m, 1H), 7.00-7.14 (m, 5H), 7.28-7.41 (m, 8H), 7.65 (d, J=7.5 Hz, 2H), 7.82 (d, J=6.9 Hz, 1H), 8.02 (d, J=15.6 Hz, 1H); ESI-MS (m/z) 458.10 $(M+H)^+$.

Example 35

2-[(E)-2-(2-Cyclopentyloxy-3-methoxyphenyl)vinyl]-1-[4-(trifluoromethyl)phenyl]-1H-benzimidazole

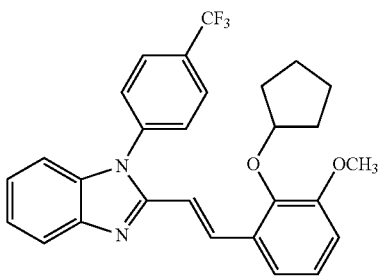 [SMILES: COc1cccc(/C=C/c2nc3ccccc3n2-c2ccc(C(F)(F)F)cc2)c1OC1CCCC1]

The title compound was prepared by coupling Intermediate 6 (100 mg, 0.299 mmol) with 1-iodo-4-(trifluoromethyl)benzene (122 mg, 0.449 mmol) in presence of $Cs_2CO_3$ (195 mg, 0.598 mmol) and CuI (11 mg, 0.059 mmol) in dry DMA (3 ml) as described in Example 1 to give 17 mg of the product as an off-white solid; IR (Neat) 3430, 2960, 1615, 1450, 1323, 1266, 1067, 742 $cm^{-1}$; $^1$H NMR (300 MHz, $CDCl_3$) δ 1.47-1.56 (m, 4H), 1.65-1.72 (m, 4H), 3.83 (s, 3H), 4.83 (br s, 1H), 6.80-6.87 (m, 1H), 6.95-7.00 (m, 3H), 7.06-7.16 (m, 1H), 7.28-7.34 (m, 2H), 7.57 (d, J=7.2 Hz, 2H), 7.80-7.87 (m, 3H), 8.08 (d, J=16.2 Hz, 1H); APCI-MS (m/z) 479.33 $(M+H)^+$.

Example 36

4-{2-[(E)-2-(2-Butoxy-3-methoxyphenyl)vinyl]-1H-benzimidazol-1-yl}benzonitrile

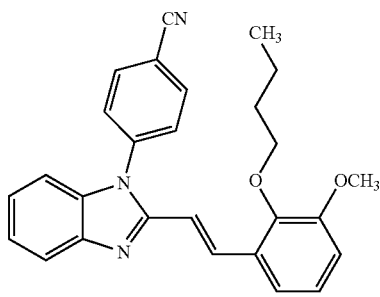

This compound was prepared by coupling Intermediate 2 (200 mg, 0.625 mmol) with 4-iodobenzonitrile (214 mg, 0.931 mmol) in presence of $Cs_2CO_3$ (405 mg, 1.242 mmol) and CuI (24 mg, 0.124 mmol) in dry DMA (3 ml) as described in Example 1 to give 98 mg of the product as an off-white solid; IR (KBr) 2925, 2231, 1602, 1476, 1385, 1271, 1074, 747 cm$^{-1}$; $^1$H NMR (300 MHz, CDCl$_3$) δ 0.92 (t, J=6.9 Hz, 3H), 1.35-1.42 (m, 2H), 2.10-2.16 (m, 2H), 3.83 (s, 3H), 3.91 (d, J=6.3 Hz, 2H), 6.80-6.86 (m, 1H), 7.00-7.07 (m, 3H), 7.11-7.18 (m, 1H), 7.30 (d, J=6.9 Hz, 2H), 7.58 (d, J=8.1 Hz, 2H), 7.82 (d, J=7.8 Hz, 1H), 7.89 (d, J=7.8 Hz, 2H), 8.08 (d, J=16.2 Hz, 1H); ESI-MS (m/z) 424.70 (M+H)$^+$.

Example 37

2-[(E)-2-(2-Cyclopropylmethoxy-3-methoxyphenyl)vinyl]-1-[4-(trifluoromethyl)phenyl]-1H-benzimidazole

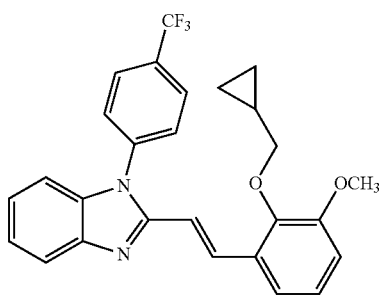

The title compound was prepared by coupling Intermediate 5 (200 mg, 0.625 mmol) with 1-iodo-4-(trifluoromethyl)benzene (340 mg, 1.249 mmol) in the presence of $Cs_2CO_3$ (407 mg, 1.249 mmol) and CuI (24 mg, 0.124 mmol) in dry DMA (5 ml) as described in Example 1 to give 34 mg of the product as an off-white solid; $^1$H NMR (300 MHz, CDCl$_3$) δ 0.18 (br s, 2H), 0.42-0.49 (m, 2H), 1.05 (br s, 1H), 3.75 (d, J=7.8 Hz, 2H), 3.83 (s, 3H), 6.82-6.90 (m, 1H), 7.00-7.09 (m, 2H), 7.14-7.20 (m, 3H), 7.30-7.36 (m, 1H), 7.59 (d, J=7.8 Hz, 2H), 7.80-7.90 (m, 3H), 8.15 (d, J=16.5 Hz, 1H); APCI-MS (m/z) 465.39 (M+H)$^+$.

Example 38

5-{2-[(E)-2-(2-Cyclopropylmethoxy-3-methoxyphenyl)vinyl]-1H-benzimidazol-1-yl}-4-fluorobenzonitrile

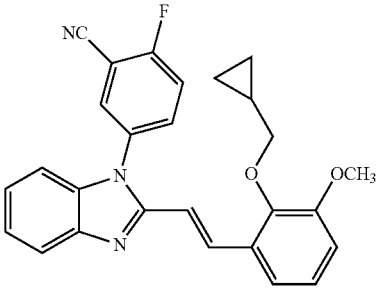 [SMILES: COc1cccc(/C=C/c2nc3ccccc3n2-c2ccc(F)c(C#N)c2)c1OCC1CC1]

The title compound was prepared by coupling Intermediate 5 (200 mg, 0.625 mmol) with 2-fluoro-5-iodobenzonitrile (232 mg, 0.937 mmol) in presence of $Cs_2CO_3$ (407 mg, 1.252 mmol) and CuI (24 mg, 0.125 mmol) in dry DMA (5 ml) as described in Example 1 to give 102 mg of the product as an off-white solid; IR (KBr) 2953, 2229, 1577, 1490, 1373, 1266, 1070, 730 cm$^{-1}$; $^1$H NMR (300 MHz, CDCl$_3$) δ 0.20 (d, J=4.2 Hz, 2H), 0.50 (d, J=4.2 Hz, 2H), 1.08 (br s, 1H), 3.70-3.77 (m, 2H), 3.83 (s, 3H), 6.84 (dd, J=2.7, 6.6 Hz, 1H), 6.93 (d, J=16.2 Hz, 1H), 6.99-7.05 (m, 3H), 7.20-7.30 (m, 2H), 7.34 (t, J=7.2 Hz, 1H), 7.82 (d, J=7.8 Hz, 1H), 8.08 (d, J=15.6 Hz, 1H), 8.13 (s, 1H), 8.20 (s, 1H); ESI-MS (m/z) 440.53 (M+H)$^+$.

Example 39

4-{2-[(E)-2-(2-Cyclopropylmethoxy-3-methoxyphenyl)vinyl]-1H-benzimidazol-1-yl}-3-fluorobenzonitrile

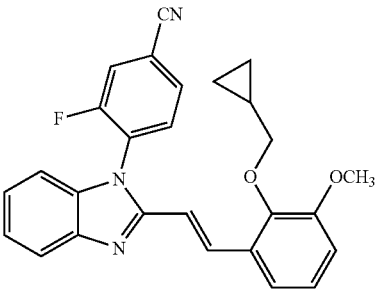

The title compound was prepared by coupling Intermediate 5 (200 mg, 0.681 mmol) with 3-fluoro-4-iodobenzonitrile (201 mg, 0.816 mmol) in presence of $Cs_2CO_3$ (442 mg, 1.362 mmol) and CuI (26 mg, 0.136 mmol) in dry DMA (5 ml) as described in Example 1 to give 36 mg of the product as an off-white solid; $^1$H NMR (300 MHz, CDCl$_3$) δ 0.19-0.24 (m, 2H), 0.50-0.56 (m, 2H), 1.12 (br s, 1H), 3.69-3.79 (m, 2H), 3.82 (s, 3H), 6.78 (d, J=15.9 Hz, 1H), 6.82-6.88 (m, 1H), 6.96-7.06 (m, 2H), 7.18-7.28 (m, 2H), 7.33 (t, J=7.5 Hz, 1H), 7.52 (dd, J=1.5, 8.1 Hz, 1H), 7.69 (s, 1H), 7.83 (d, J=8.4 Hz, 1H), 8.04 (d, J=16.2 Hz, 1H), 8.20 (d, J=8.4 Hz, 1H); ESI-MS (m/z) 440.48 (M+H)$^+$.

Example 40

2-[(E)-2-(2-Cyclopentyloxy-3-methoxyphenyl)vinyl]-1-(4-tert-butylbenzyl)-1H-benzimidazole

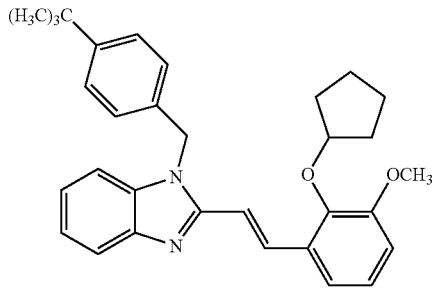 [SMILES: COc1cccc(/C=C/c2nc3ccccc3n2Cc2ccc(C(C)(C)C)cc2)c1OC1CCCC1]

The title compound was prepared by coupling Intermediate 6 (200 mg, 0.598 mmol) with 4-tert butyl benzyl bromide (203 mg, 0.898 mmol) in presence of $Cs_2CO_3$ (389 mg, 1.196 mmol) and CuI ((24 mg, 0.125 mmol)) in dry DMA (5 ml) as described in Example 1 to give 37 mg of the product as an off-white solid; IR (KBr) 2960, 1633, 1402, 1265, 1073, 737 cm$^{-1}$; $^1$H NMR (300 MHz, CDCl$_3$) δ 1.31 (s, 9H), 1.45-1.53 (m, 2H), 1.61-1.81 (m, 6H), 3.83 (s, 3H), 4.81 (br s, 1H), 5.41 (s, 2H), 6.83 (d, J=7.8 Hz, 1H), 6.99-7.09 (m, 3H), 7.19-7.29 (m, 7H), 7.77 (d, J=8.4 Hz, 1H), 8.09 (d, J=15.6 Hz, 1H); ESI-MS (m/z) 481.53 (M+H)$^+$.

Example 41

1-(2,4-Difluorobenzyl)-2-[(E)-2-(2-cyclopropylmethoxy-3-methoxyphenyl)vinyl]-1H-benzimidazole

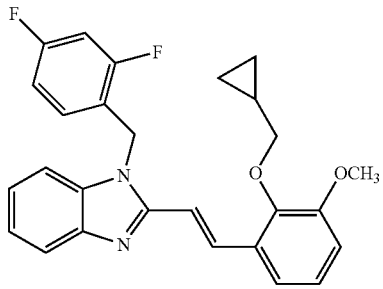 [SMILES: COc1cccc(/C=C/c2nc3ccccc3n2Cc2ccc(F)cc2F)c1OCC1CC1]

The title compound was prepared by coupling Intermediate 5 (200 mg, 0.681 mmol) with 1-(bromomethyl)-2,4-difluorobenzene (244 mg, 1.021 mmol) in presence of $Cs_2CO_3$ (442 mg, 1.362 mmol) and CuI (26 mg, 0.136 mmol) in dry DMA (5 ml) as described in Example 1 to give 36 mg of the product as an off-white solid; $^1$H NMR (300 MHz, CDCl$_3$) δ 0.18-0.24 (m, 2H), 0.48-0.54 (m, 2H), 1.21 (br s, 1H), 3.67-3.77 (m, 2H), 3.82 (s, 3H), 6.82 (s, 1H), 6.88-6.95 (m, 2H), 7.00-7.08 (m, 2H), 7.19-7.25 (m, 4H), 7.31 (t, J=7.5 Hz, 1H), 7.82 (d, J=7.8 Hz, 1H), 7.95-8.01 (m, 2H), 8.06 (s, 1H); ESI-MS (m/z) 447.53 (M+H)$^+$.

Example 42

4-({2-[(E)-2-(2-Cyclopropylmethoxy-3-methoxyphenyl)vinyl]-1H-benzimidazol-1-yl}methyl)benzonitrile

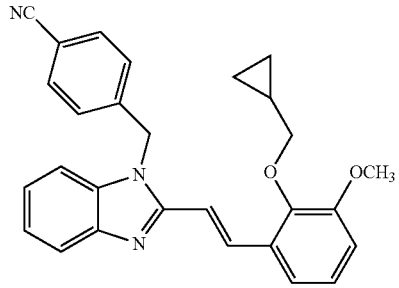 [SMILES: COc1cccc(/C=C/c2nc3ccccc3n2Cc2ccc(C#N)cc2)c1OCC1CC1]

The title compound was prepared by coupling Intermediate 5 (100 mg, 0.341 mmol) with 4-(bromomethyl)benzonitrile (73 mg, 0.372 mmol) in the presence of $Cs_2CO_3$ (221 mg, 0.682 mmol) and CuI (11 mg, 0.059 mmol) in dry DMA (5 ml) as described in Example 1 to give 56 mg of the product as an off-white solid; $^1$H NMR (300 MHz, CDCl$_3$) δ 0.15-0.21 (m, 2H), 0.45-0.51 (m, 2H), 1.12 (br s, 1H), 3.78 (d, J=5.4 Hz, 2H), 3.85 (s, 3H), 5.53 (s, 2H), 6.87 (d, J=6.3 Hz, 1H), 7.00-7.09 (m, 2H), 7.20-7.26 (m, 4H), 7.30-7.36 (m, 2H), 7.60 (d, J=6.3 Hz, 2H), 7.83 (d, J=6.3 Hz, 1H), 8.13 (d, J=12.0 Hz, 1H); ESI-MS (m/z) 436.26 (M+H)$^+$.

Example 43

4-({2-[(E)-2-(2-Cyclopentyloxy-3-methoxyphenyl)vinyl]-1H-benzimidazol-1-yl}methyl)benzonitrile

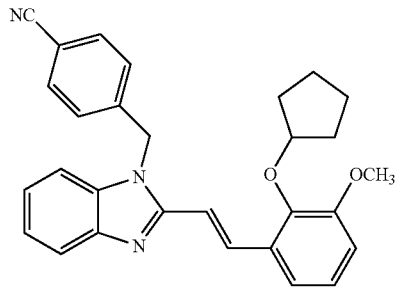 [SMILES: COc1cccc(/C=C/c2nc3ccccc3n2Cc2ccc(C#N)cc2)c1OC1CCCC1]

The title compound was prepared by coupling Intermediate 6 (200 mg, 0.598 mmol) with 4-cyanobenzylbromide (129 mg, 0.658 mmol) in the presence of $Cs_2CO_3$ (390 mg, 1.196 mmol) and CuI in dry DMF (5 ml) as described in Example 1 to give 37 mg of the product as an off-white solid; $^1$H NMR (300 MHz, CDCl$_3$) δ 1.45-1.53 (m, 2H), 1.61-1.71 (m, 3H), 1.72-1.81 (m, 5H), 3.86 (s, 3H), 4.81-4.89 (m, 1H), 6.88 (d, J=8.1 Hz, 1H), 7.02 (t, J=7.5 Hz, 1H), 7.07 (d, J=7.8 Hz, 1H), 7.14 (s, 1H), 7.16-7.26 (m, 4H), 7.31 (d, J=7.8 Hz, 1H), 7.61 (d, J=7.5 Hz, 2H), 7.83 (d, J=7.5 Hz, 1H), 8.10 (d, J=15 Hz, 1H). ESI-MS (m/z) 450 (M+H)$^+$

Example 44

4-({2-[(E)-2-(2-{2-Fluorobenzyloxy}-3-methoxyphenyl)vinyl]-1H-benzimidazol-1-yl}methyl)benzonitrile

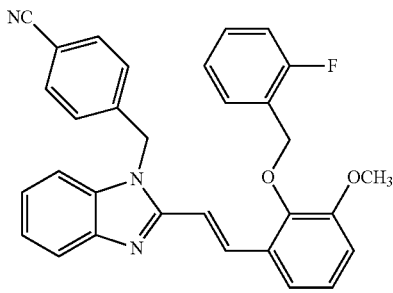 [SMILES: COc1cccc(/C=C/c2nc3ccccc3n2Cc2ccc(C#N)cc2)c1OCc1ccccc1F]

The title compound was prepared by coupling Intermediate 8 (200 mg, 0.63 mmol) with 4-(bromomethyl)benzonitrile (136 mg, 0.704 mmol) in the presence of $Cs_2CO_3$ (410 mg, 1.26 mmol) in dry DMF (5 ml) as described in Example 1 to give 141 mg of the product as an off-white solid; IR (KBr) 2945, 2230, 1581, 1478, 1275, 1071, 759 cm$^{-1}$; $^1$H NMR (300 MHz, CDCl$_3$) δ 3.85 (s, 3H), 5.11 (s, 2H), 5.37 (s, 2H), 6.89-6.94 (m, 1H), 6.96-7.02 (m, 1H), 7.04-7.10 (m, 6H), 7.12-7.22 (m, 2H), 7.28-7.33 (m, 2H), 7.53 (d, J=8.4 Hz, 2H), 7.82 (d, J=7.8 Hz, 1H), 8.01 (d, J=15.9 Hz, 1H); APCI-MS (m/z) 490.24 (M+H)$^+$.

Example 45

2-[(E)-2-(2-Cylopropymethoxy-3-methoxyphenyl)]-1-(2-thienyl)-1H-benzimidazole

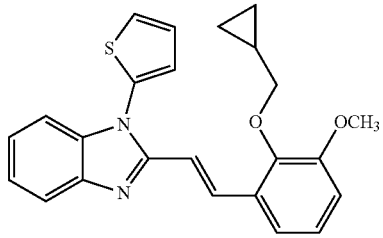 [SMILES: COc1cccc(/C=C/c2nc3ccccc3n2-c2cccs2)c1OCC1CC1]

The title compound was prepared by coupling Intermediate 5 (200 mg, 0.625 mmol) with 2-iodo thiophene (197 mg, 0.937 mmol) in presence of $Cs_2CO_3$ (407 mg, 1.251 mmol) and CuI (24 mg, 0.125 mmol) in dry DMA (5 ml) as described in Example 1 to give 59 mg of the product as an off-white solid; IR (KBr) 3061, 2924, 1631, 1577, 1478, 1270, 977, 735 cm$^{-1}$; $^1$H NMR (300 MHz, CDCl$_3$) δ 0.20-0.30 (m, 2H), 0.40-0.50 (m, 2H), 1.58 (br s, 1H), 3.79 (d, J=5.4 Hz, 2H), 3.84 (s, 3H), 6.85 (d, J=7.2 Hz, 1H), 7.00 (d, J=6.0 Hz, 1H), 7.07 (d, J=5.7 Hz, 1H), 7.14-7.20 (m, 3H), 7.24-7.30 (m, 2H), 7.34-7.42 (m, 1H), 7.43 (d, J=3.6 Hz, 1H), 7.80 (d, J=6.0 Hz, 1H), 8.15 (d, J=12.3 Hz, 1H); APCI-MS (m/z) 403.25 (M+H)$^+$.

Example 46

2-[(E)-2-(2-Cyclopropyloxy-3-methoxyphenyl)vinyl]-1-(1,3-thiazol-2-yl)-1H-benzimidazole

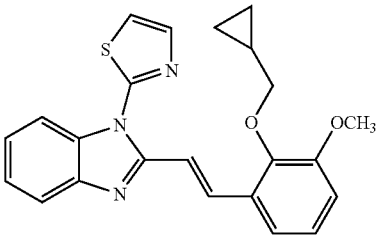 [SMILES: COc1cccc(/C=C/c2nc3ccccc3n2-c2nccs2)c1OCC1CC1]

This compound was prepared by coupling Intermediate 5 (200 mg, 0.625 mmol) with 2-bromothiazole (307 mg, 1.875 mmol) in presence of $Cs_2CO_3$ (407 mg, 1.251 mmol) and CuI (24 mg, 0.125 mmol) in dry DMA (5 ml) as described in Example 1 to give 84 mg of the product as an off-white solid; IR (Neat) 2934, 1626, 1576, 1476, 1267, 1087, 740 cm$^{-1}$; $^1$H NMR (300 MHz, CDCl$_3$) δ 0.20-0.26 (m, 2H), 0.50-60 (m, 2H), 1.26 (br s, 1H), 3.78-0.90 (m, 5H), 6.88 (d, J=9.0 Hz, 1H), 7.02 (t, J=6.0 Hz, 1H), 7.18 (d, J=5.1 Hz, 1H), 7.33-7.47 (m, 2H), 7.52-7.60 (m, 1H), 7.66 (d, J=6.6 Hz, 1H), 7.73 (d, J=6.0 Hz, 1H), 7.81 (d, J=5.7 Hz, 1H), 7.87 (d, J=9.9 Hz, 1H), 8.25 (d, J=12.6 Hz, 1H); APCI-MS (m/z) 404.30 (M+H)$^+$.

Example 47

2-[(E)-2-(2-Cyclopentyloxy-3-methoxyphenyl)vinyl]-1-(1,3-thiazol-2-yl)-1H-benzimidazole

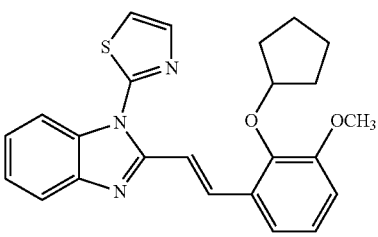 [SMILES: COc1cccc(/C=C/c2nc3ccccc3n2-c2nccs2)c1OC1CCCC1]

This compound was prepared by coupling Intermediate 6 (200 mg, 0.598 mmol) with 2-bromothiazole (147 mg, 0.898 mmol) in presence of $Cs_2CO_3$ (390 mg, 1.196 mmol) and CuI (23 mg, 0.119 mmol) in dry DMA (5 ml) as described in Example 1 to give 43 mg of the product as an off-white solid; IR (KBr) 2957, 1625, 1499, 1448, 12658, 1060, 747 cm$^{-1}$; $^1$H NMR (300 MHz, CDCl$_3$) δ 1.52-1.58 (m, 2H), 1.62-1.69 (m, 2H), 1.76-1.90 (m, 4H), 3.85 (s, 3H), 4.89 (br s, 1H), 6.88 (d, J=7.2 Hz, 1H), 7.00-7.06 (m, 1H), 7.15 (d, J=6.9 Hz, 1H), 7.28-7.38 (m, 2H), 7.45 (s, 1H), 7.49 (d, J=12.0 Hz, 1H), 7.61 (d, J=5.7 Hz, 1H), 7.82 (d, J=6.0 Hz, 1H) 7.88 (s, 1H), 8.18 (d, J=12.0 Hz, 1H); ESI-MS (m/z) 418.53 (M+H)$^+$.

Example 48

2-{2-[(E)-2-(2-[Cyclopentyloxy]-3-methoxyphenyl)vinyl]-1H-benzimidazol-1-yl}-1,3-thiazole-5-carbonitrile

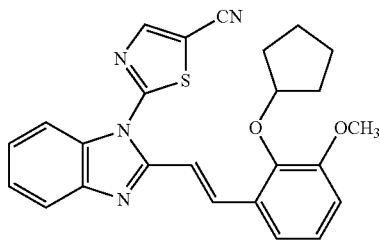 [SMILES: COc1cccc(/C=C/c2nc3ccccc3n2-c2ncc(C#N)s2)c1OC1CCCC1]

The title compound was prepared by coupling Intermediate 6 (200 mg, 0.59 mmol) with 2-bromo-1,3-thiazole-5-carbonitrile (135.8 mg, 0.71 mmol) in the presence of $Cs_2CO_3$ (390 mg, 1.19 mmol) and CuI (22 mg, 0.111 mmol) in dry DMA (5 ml) as described in Example 1 to give 37 mg of the product as an off-white solid; IR (KBr) 2955, 2221, 1508, 1462, 1267, 1150, 967 cm$^{-1}$; $^1$H NMR (300 MHz, CDCl$_3$) δ 1.60-1.69 (m, 4H), 1.74-1.83 (m, 4H), 3.88 (s, 3H), 4.92 (br s, 1H), 6.93 (d, J=7.8 Hz, 1H), 7.07 (t, J=7.8 Hz, 1H), 7.20 (d, J=7.2 Hz, 1H), 7.36-7.45 (m, 2H), 7.60 (d, J=15.9 Hz, 1H), 7.85 (d, J=6.9 Hz, 2H), 8.23 (s, 1H), 8.30 (s, 1H); ESI-MS (m/z) 443.16 (M+H)$^+$.

Example 49

2-{2-[(E)-2-(2-Cyclopentyloxy-3-methoxyphenyl)vinyl]-1H-benzimidazol-1-yl}-4-methyl-1,3-thiazole-5-carbonitrile

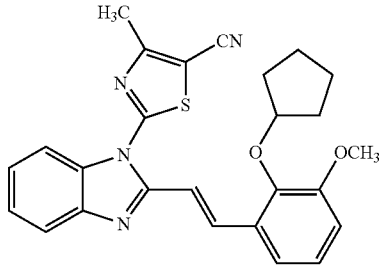 [SMILES: COc1cccc(/C=C/c2nc3ccccc3n2-c2nc(C)c(C#N)s2)c1OC1CCCC1]

The title compound was prepared by coupling Intermediate 6 (200 mg, 0.589 mmol) with 2-iodo-4-methyl-1,3-thiazole-5-carbonitrile (180 mg, 0.714 mmol) in presence of $Cs_2CO_3$ (390 mg, 1.189 mmol) and CuI (23 mg, 0.118 mmol) in dry DMA (5 ml) as described in Example 1 to give 60 mg of the product as an off-white solid; IR (KBr) 2925, 2218, 1475, 1267, 1068, 758 cm$^{-1}$; $^1$H NMR (300 MHz, CDCl$_3$) δ 1.57-1.68 (m, 4H), 1.76-1.86 (m, 4H), 2.73 (s, 3H), 3.86 (s, 3H), 4.90 (br s, 1H), 6.90 (d, J=7.2 Hz, 1H), 7.04 (d, J=7.8 Hz, 1H), 7.16 (d, J=7.8 Hz, 1H), 7.36 (t, J=6.6 Hz, 2H), 7.54 (d, J=16.2 Hz, 1H), 7.77-7.83 (m, 2H), 8.20 (d, J=15.6 Hz, 1H); ESI-MS (m/z) 457.54 (M+H)$^+$.

Example 50

2-{2-[(E)-2-(2-Cyclopropylmethoxy-3-methoxyphenyl)vinyl]-1H-benzimidazol-1-yl}-1,3-benzothiazole

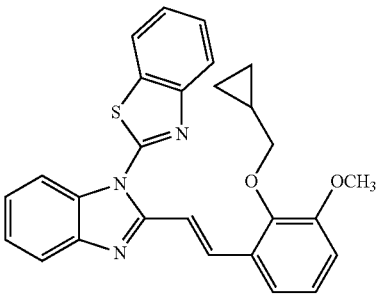 [SMILES: COc1cccc(/C=C/c2nc3ccccc3n2-c2nc3ccccc3s2)c1OCC1CC1]

The title compound was prepared by coupling Intermediate 5 (200 mg, 0.625 mmol) with 2-chloro-1,3-benzothiazole (171 mg, 1.251 mmol) in presence of $Cs_2CO_3$ (407 mg, 1.251 mmol) and CuI (24 mg, 0.125 mmol) in dry DMA (5 ml) as described in Example 1 to give 55 mg of the product as an off-white solid; IR (KBr) 2936, 1668, 1514, 1358, 1271, 1069, 736 cm$^{-1}$; $^1$H NMR (300 MHz, CDCl$_3$) δ 0.18-0.24 (m, 2H), 0.40-0.48 (m, 2H), 1.18 (br s, 1H), 3.81 (s, 2H), 3.84 (s, 3H), 6.86 (d, J=7.8 Hz, 1H), 7.02 (t, J=8.4 Hz, 1H), 7.17 (d, J=7.8 Hz, 1H), 7.30-7.37 (m, 2H), 7.48 (t, J=7.8 Hz, 1H), 7.58 (t, J=6.9 Hz, 1H), 7.74 (d, J=16.2 Hz, 1H), 7.84 (t, J=8.4 Hz, 2H) 7.92 (d, J=7.8 Hz, 1H), 8.12 (d, J=7.8 Hz, 1H), 8.34 (d, J=16.2 Hz, 1H); APCI-MS (m/z) 454.30 (M+H)$^+$.

Example 51

6-{2-[(E)-2-(2-Cyclopentyloxy-3-methoxyphenyl)vinyl]-6-methoxy-1H-benzimidazol-1-yl}nicotinonitrile

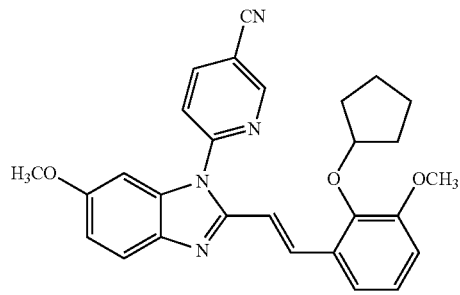 [SMILES: COc1ccc2nc(/C=C/c3cccc(OC)c3OC3CCCC3)n(-c3ccc(C#N)cn3)c2c1]

The title compound was prepared by coupling Intermediate 15 (200 mg, 0.549 mmol) with 6-chloronicotinonitrile (114 mg, 0.824 mmol) in the presence of $Cs_2CO_3$ (358 mg, 1.098 mmol) and CuI (21 mg, 0.109 mmol) in dry DMA (3 ml) as described in Example 1 The compound was further recrystallized from ethyl acetate to obtain 80 mg of the desired regioisomer as an off-white solid; IR (KBr) 2957, 2232, 1590, 1477, 1267, 1158, 969 cm$^{-1}$; $^1$H NMR (300 MHz, CDCl$_3$) δ 1.60-1.77 (m, 8H), 3.86 (s, 3H), 3.90 (s, 3H), 4.88 (br s, 1H), 6.88-6.99 (m, 1H), 6.99-7.12 (m, 2H), 7.33 (s, 1H), 7.45 (d, J=8.7 Hz, 1H), 7.62 (d, J=6.6 Hz, 1H), 7.73 (d, J=9.0 Hz, 1H), 8.07 (d, J=16.2 Hz, 1H), 8.16-8.22 (m, 2H), 9.02 (d, J=4.2 Hz, 1H); APCI-MS (m/z) 467.91 (M+H)$^+$.

Example 52

6-(6-Chloro-2-{(E)-2-[3-methoxy-2-(2-methylpropoxy)phenyl]ethenyl}-1H-benzimidazol-1-yl)pyridine-3-carbonitrile

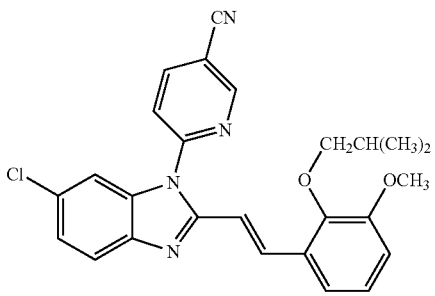

The title compound was prepared by dissolving Intermediate 32 (150 mg, 0.315 mmol) in glacial acetic acid (5 ml) and heating it at 120-130° C. for 3 h under nitrogen atmosphere. After completion of the reaction, excess of acetic acid was evaporated and the reaction mixture was diluted with water and extracted with ethyl acetate (2×25 ml). The combined organic layers were then washed with water (3×20 ml), brine (20 ml) and dried over $Na_2SO_4$, filtered and concentrated under reduced pressure. The crude product obtained was purified by silica gel column chromatography using 12% acetone in petroleum ether to give 70 mg of the product; IR (KBr) 2950, 2231, 1590, 1479, 1270, 1004, 785 cm$^{-1}$; $^1$H NMR (300 MHz, DMSO-d$_6$) δ 0.97 (d, J=6.3 Hz, 6H), 1.90-1.97 (m, 1H), 3.69 (d, J=6.3 Hz, 2H), 3.81 (s, 2H), 7.06 (br s, 2H), 7.25 (d, J=16.2 Hz, 2H), 7.37 (d, J=9.0 Hz, 1H), 7.62 (s, 1H), 7.76 (d, J=9.0 Hz, 1H), 8.00 (d, J=8.4 Hz, 1H), 8.13 (d, J=16.2 Hz, 2H), 8.69 (d, J=6.9 Hz, 1H), 9.25 (s, 1H); ESI-MS (m/z) 459.31 (M+H)$^+$.

Example 53

6-{2-[(E)-2-(2-Cyclopentyloxy-3-methoxyphenyl)vinyl]-6-fluoro-1H-benzimidazol-1-yl}nicotinonitrile

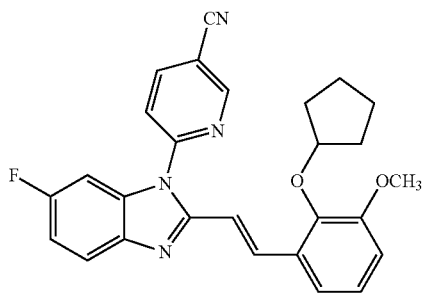 [SMILES: COc1cccc(/C=C/c2nc3ccc(F)cc3n2-c2ccc(C#N)cn2)c1OC1CCCC1]

This mixture of compounds was prepared by coupling Intermediate 13 (300 mg, 0.852 mmol) with 6-chloronicotinonitrile (177 mg, 0.1.278 mmol) in the presence of $Cs_2CO_3$ (555 mg, 1.704 mmol) and CuI (33 mg, 0.107 mmol) in dry DMA (5 ml) as described in Example 1. The compound was further recrystallized from ethyl acetate to obtain 70 mg of the desired regioisomer as an off-white solid; IR (KBr) 2959, 2232, 1592, 1477, 1267, 1173, 800 cm$^{-1}$; $^1$H NMR (300 MHz, CDCl$_3$) δ 1.61-1.78 (m, 8H), 3.85 (s, 3H), 4.87 (br s, 1H), 6.87 (d, J=7.8 Hz, 1H), 6.97-7.11 (m, 3H), 7.20-7.28 (m, 1H), 7.47 (d, J=8.4 Hz, 1H), 7.59 (d, J=6.6 Hz, 1H), 7.70-7.76 (m, 1H), 8.11 (d, J=15.0 Hz, 1H), 8.19 (d, J=7.2 Hz, 1H), 8.99 (s, 1H); APCI-MS (m/z) 455.35 (M+H)$^+$.

Example 54

6-{6-Chloro-2-[(E)-2-(2-cyclopentyloxy-3-methoxyphenyl)vinyl]-1H-benzimidazol-1-yl}nicotinonitrile

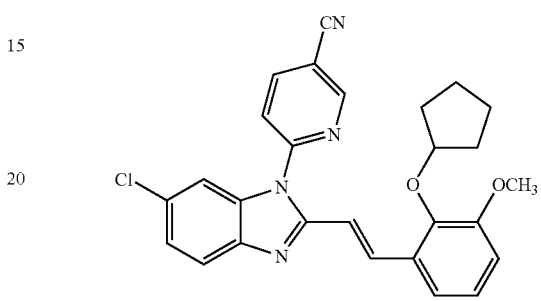

The title compound was prepared by coupling Intermediate 14 (1 g, 2.711 mmol) with 6-chloronicotinonitrile (488 mg, 3.522 mmol) in the presence of $Cs_2CO_3$ (1.76 g, 5.40 mmol) and CuI (103 mg, 0.540 mmol) in dry DMA (15 ml) as described in Example 1 to give 600 mg of the crude product which was a mixture of the regioisomers. The isomers were separated by preparative HPLC to yield 100 mg of the less polar product (6-chloro isomer) as an off-white solid; IR (KBr) 2953, 2236, 1591, 1479, 1268, 1067, 769 cm$^{-1}$; $^1$H NMR (300 MHz, DMSO-d$_6$) δ 1.55-1.65 (m, 4H), 1.68-1.76 (m, 4H), 3.81 (s, 3H), 4.87 (br s, 1H), 7.06 (s, 2H), 7.20-7.28 (m, 2H), 7.37 (d, J=9.3, 1H), 7.62 (s, 1H), 7.77 (d, J=8.4, 1H), 8.00 (d, J=8.4 Hz, 1H), 8.14 (d, J=16.2, 1H), 8.69 (d, J=7.5, 1H), 9.25 (s, 1H); ESI-MS (m/z) 471.25 (M)$^+$.

Example 55

6-{5-chloro-2-[(E)-2-(2-cyclopentyloxy-3-methoxyphenyl)vinyl]-1H-benzimidazol-1-yl}nicotinonitrile

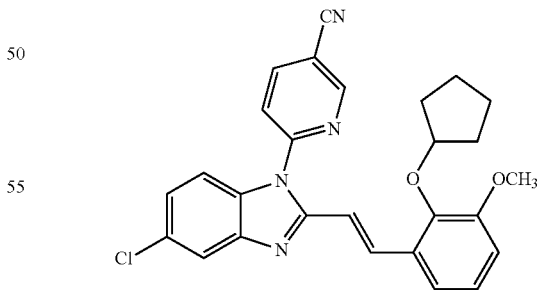

The more polar product (68 mg) obtained by preparative HPLC from Example 54 was characterized as the title compound (5-chloro isomer), which was isolated as on off-white solid; IR (KBr) 2957, 2233, 1591, 1477, 1268, 1068, 776 cm$^{-1}$; $^1$H NMR (300 MHz, DMSO-d$_6$) δ 1.59-1.67 (m, 4H), 1.69-1.77 (m, 4H), 3.81 (s, 3H), 4.87 (br s, 1H), 7.06 (s, 2H), 7.22-7.34 (m, 3H), 7.56 (d, J=8.4, 1H), 7.83 (s, 1H), 7.99 (d, J=8.4, 1H), 8.16 (d, J=16.2 Hz, 1H), 8.70 (d, J=7.8, 1H), 9.25 (s, 1H); ESI-MS (m/z) 471.21 (M+H)+.

Example 56

6-{2-[(E)-2-(2-[Cyclopentyloxy]-3-methoxyphenyl)vinyl]-5-methoxy-1H-benzimidazol-1-yl}nicotinonitrile

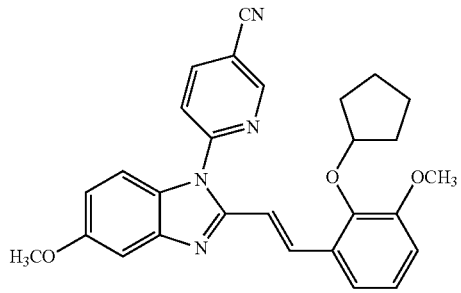 [SMILES: COc1ccc2c(c1)nc(/C=C/c1cccc(OC)c1OC1CCCC1)n2-c1ccc(C#N)cn1]

The title compound was prepared by cyclization of Intermediate 34 in glacial acetic acid as described in Example 52 to give 120 mg of the product as an off-white solid; IR (KBr) 3429, 2959, 2233, 1590, 1477, 1267, 1159 cm$^{-1}$; $^1$H NMR (300 MHz, CDCl$_3$) δ 1.69-1.77 (m, 8H), 3.86 (s, 3H), 3.90 (s, 3H), 4.89 (br s, 1H), 6.88-6.96 (m, 3H), 7.03 (t, J=7.8 Hz, 1H), 7.29-7.34 (m, 2H), 7.44 (d, J=9.3 Hz, 1H), 7.63 (d, J=8.1 Hz, 1H), 8.21 (d, J=6.9 Hz, 2H), 9.01 (s, 1H); ESI-MS (m/z) 467.25 (M+H)+.

Example 57

6-{2-[(E)-2-(2-[Cyclopentyloxy]-3-methoxyphenyl)vinyl]-5-(trifluoromethyl)-1H-benzimidazol-1-yl}nicotinonitrile

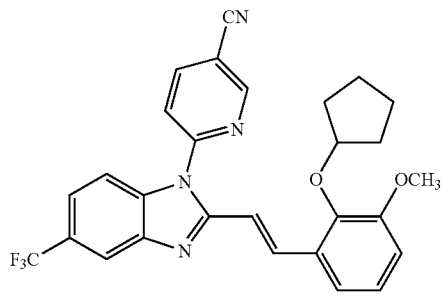 [SMILES: COc1cccc(/C=C/c2nc3cc(C(F)(F)F)ccc3n2-c2ccc(C#N)cn2)c1OC1CCCC1]

The title compound was prepared by cyclization of Intermediate 33 in glacial acetic acid as described in Example 52 to give 268 mg of the product as an off-white solid; IR (KBr) 2954, 2233, 1590, 1480, 1267, 1119, 771 cm$^{-1}$; $^1$H NMR (300 MHz, CDCl$_3$) δ 1.61-1.68 (m, 4H), 1.70-1.80 (m, 4H), 3.87 (s, 3H), 4.91 (br s, 1H), 6.91 (d, J=7.5 Hz, 1H), 7.03 (t, J=7.8 Hz, 1H), 7.10 (d, J=7.8 Hz, 1H), 7.21 (s, 1H), 7.54 (d, J=8.4 Hz, 1H), 7.60-7.66 (m, 2H), 8.11 (s, 1H), 8.23-8.29 (m, 2H), 9.02 (s, 1H); ESI-MS (m/z) 505.17 (M+H)+.

Example 58

6-{6-(Difluoromethoxy)-2-[(E)-2-(2-[cyclopentyloxy]-3-methoxyphenyl)vinyl]-1H-benzimidazol-1-yl}nicotinonitrile

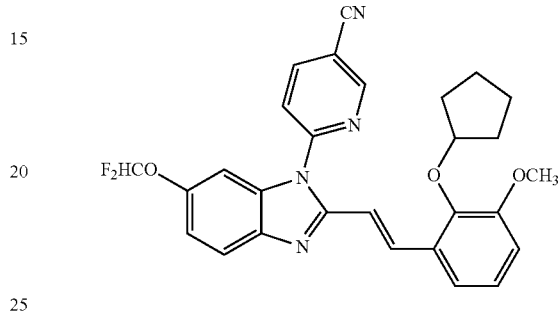

The title compound was prepared by coupling Intermediate 16 (200 mg, 0.50 mmol) with 6-chloronicotinonitrile (104 mg, 0.75 mmol) in the presence of Cs$_2$CO$_3$ (326 mg, 1.0 mmol) and CuI (19.5 mg, 0.10 mmol) in dry DMA (3 ml) as described in Example 1 as the crude product. This product was further recrystallized from ethyl acetate to obtain 82 mg of the desired regioisomer as an off-white solid; IR (KBr) 3429, 2960, 2232, 1591, 1476, 1267, 1120, 773 cm$^{-1}$; APCI-MS (m/z) 503.18 (M+H)+.

Example 59

6-{2-[(E)-2-(2-[Cyclopentyloxy]-3-methoxyphenyl)vinyl]-5-(difluoromethoxy)-1H-benzimidazol-1-yl}nicotinonitrile

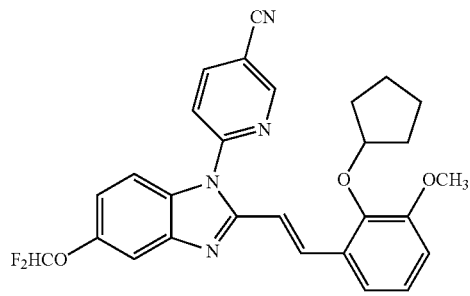 [SMILES: COc1cccc(/C=C/c2nc3cc(OC(F)F)ccc3n2-c2ccc(C#N)cn2)c1OC1CCCC1]

The title compound was prepared by cyclization of Intermediate 35 in glacial acetic acid as described in Example 52 to give 268 mg of the product as an off-white solid; IR (KBr) 2966, 2235, 1595, 1478, 1267, 1124, 784 cm$^{-1}$; $^1$H NMR (300 MHz, CDCl$_3$) δ 1.60-1.69 (m, 4H), 1.72-1.80 (m, 4H), 3.87 (s, 3H), 4.90 (br s, 1H), 6.56 (t, J=73.8 Hz, 1H), 6.90 (d, J=7.8 Hz, 1H), 7.03 (t, J=7.8 Hz, 1H), 7.10 (d, J=7.8 Hz, 1H), 7.28 (s, 1H), 7.52 (d, J=8.7 Hz, 1H), 7.59-7.66 (m, 3H), 8.19-8.24 (m, 2H), 9.02 (s, 1H); ESI-MS (m/z) 503.16 (M+H)+.

Example 60

Methyl 6-{2-[(E)-2-(2-Cyclopentyloxy-3-methoxyphenyl)vinyl]-6-fluoro-1H-benzimidazol-1-yl}nicotinate

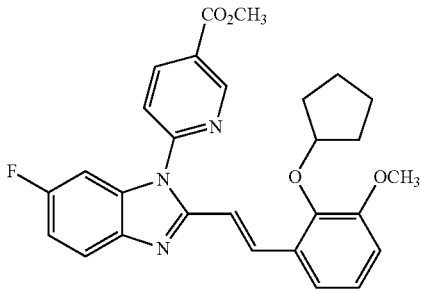 [SMILES: COC(=O)c1ccc(-n2c(/C=C/c3cccc(OC)c3OC3CCCC3)nc3ccc(F)cc32)nc1]

This mixture of compounds was prepared by coupling Intermediate 13 (200 mg, 0.568 mmol) with methyl 6-chloronicotinate (117 mg, 0.681 mmol) in presence of Cs$_2$CO$_3$ (370 mg, 1.136 mmol) and CuI (22 mg, 0.113 mmol) in dry DMA (5 ml) as described in Example 1. The compound was further recrystallized from ethyl acetate to obtain 75 mg of the desired regio-isomer as an off-white solid; IR (KBr) 2951, 1632, 1575, 1475, 1265, 1071, 772 cm$^{-1}$; $^1$H NMR (300 MHz, CDCl$_3$) δ 1.56-1.66 (m, 4H), 1.78-1.85 (m, 4H), 3.81 (s, 3H), 3.89 (d, J=7.8 Hz, 3H), 4.85 (br s, 1H), 6.98-7.11 (m, 4H), 7.33-7.44 (m, 3H), 7.50-7.60 (m, 3H), 8.02-8.11 (m, 1H); ESI-MS (m/z) 488.83 (M+H)+.

Example 61

2-{2-[(E)-2-(2-Cyclopentyloxy-3-methoxyphenyl)vinyl]-5,6-difluoro-1H-benzimidazol-1-yl}nicotinonitrile

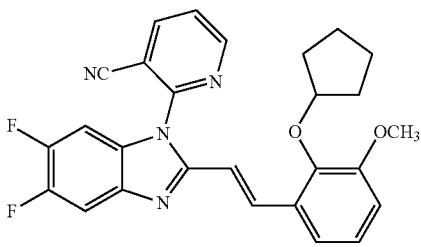 [SMILES: COc1cccc(/C=C/c2nc3cc(F)c(F)cc3n2-c2ncccc2C#N)c1OC1CCCC1]

The title compound was prepared by coupling Intermediate 23 (200 mg, 0.54 mmol) with 2-chloronicotinonitrile (113 mg, 0.810 mmol) in the presence of Cs$_2$CO$_3$ (352 mg, 1.081 mmol) and CuI (21 mg, 0.108 mmol) in dry DMA (5 ml) as described in Example 1. The crude product was purified by silica gel column chromatography using 12% acetone in petroleum ether to give 111 mg of the product as an off-white solid; IR (KBr) 2960, 2233, 1624, 1467, 1437, 1261, 1072, 778 cm$^{-1}$; $^1$H NMR (300 MHz, CDCl$_3$) δ 1.60-1.68 (m, 4H), 1.72-1.80 (m, 4H), 3.84 (s, 3H), 4.81 (br s, 1H), 6.87 (d, J=7.2 Hz, 1H), 6.93-7.05 (m, 4H), 7.60-7.65 (m, 2H), 7.97 (d, J=16.2 Hz, 1H), 8.29 (d, J=7.2 Hz, 1H), 8.95 (s, 1H); APCI-MS (m/z) 473.24 (M+H)+.

Example 62

6-{2-[(E)-2-(2-[Cyclopentyloxy]-3-methoxyphenyl)vinyl]-5,6-dimethyl-1H-benzimidazol-1-yl}nicotinonitrile

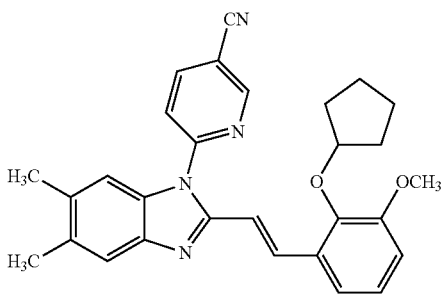 [SMILES: COc1cccc(/C=C/c2nc3cc(C)c(C)cc3n2-c2ccc(C#N)cn2)c1OC1CCCC1]

The title compound was prepared by coupling Intermediate 25 (200 mg, 0.552 mmol) with 6-chloronicotinonitrile (116 mg, 0.828 mmol) in the presence of Cs$_2$CO$_3$ (360 mg, 1.104 mmol) and CuI (21 mg, 0.110 mmol) in dry DMA (3 ml) as described in Example 1 to give 92 mg of the product as an off-white solid; IR (KBr) 2960, 2230, 1593, 1476, 1269, 1069, 979 cm$^{-1}$; $^1$H NMR (300 MHz, CDCl$_3$) δ 1.64-1.82 (m, 8H), 2.32 (d, J=9.3 Hz, 6H), 3.81 (s, 3H), 4.86 (br s, 1H), 7.02 (s, 2H), 7.24 (d, J=15.6 Hz, 2H), 7.36 (s, 1H), 7.53 (s, 1H), 7.94 (d, J=8.1 Hz, 1H), 8.07 (d, J=16.2 Hz, 1H), 8.66 (d, J=8.4 Hz, 1H), 9.23 (s, 1H); APCI-MS (m/z) 465.28 (M+H)+.

Example 63

6-{2-[(E)-2-(2-Ethoxy-3-methoxyphenyl)vinyl]-5,6-difluoro-1H-benzimidazol-1-yl}nicotinonitrile

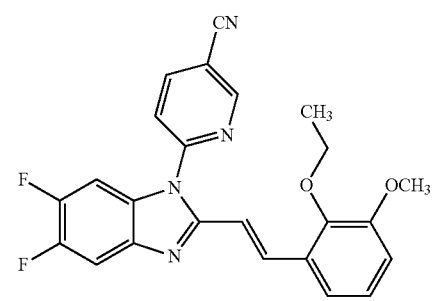 [SMILES: CCOc1c(/C=C/c2nc3cc(F)c(F)cc3n2-c2ccc(C#N)cn2)cccc1OC]

The title compound was prepared by coupling Intermediate 17 (250 mg, 0.62 mmol) with 6-chloronicotinonitrile (128 mg, 0.93 mmol) in the presence of Cs$_2$CO$_3$ (303 mg, 0.93 mmol) and CuI (11 mg, 0.062 mmol) in dry DMF (6 ml) as described in Example 1 to give 90 mg of the product as an off-white solid; IR (KBr) 2973, 2231, 1593, 1470, 1269, 1156, 778 cm$^{-1}$; $^1$H NMR (300 MHz, CDCl$_3$) δ 1.33 (t, J=7.2 Hz, 3H), 3.88 (s, 3H), 4.04-4.11 (m, 2H), 6.93 (s, 1H), 7.02-7.08 (m, 2H), 7.28 (s, 1H), 7.43-7.49 (m, 1H), 7.58-7.63 (m, 2H), 8.14 (d, J=16.2 Hz, 1H), 8.23 (d, J=7.2 Hz, 1H), 9.02 (s, 1H); APCI-MS (m/z) 433.25 (M+H)+.

Example 64

6-{2-[(E)-2-(2-Butoxy-3-methoxyphenyl)vinyl]-5,6-difluoro-1H-benzimidazol-1-yl}-nicotinonitrile

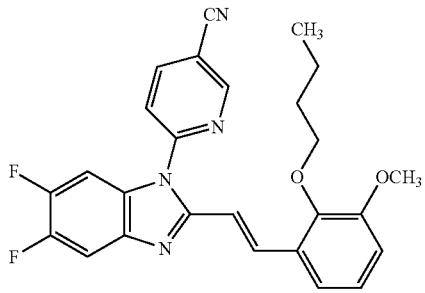 [SMILES: CCCCOc1c(/C=C/c2nc3cc(F)c(F)cc3n2-c2ccc(C#N)cn2)cccc1OC]

The title compound was prepared by coupling Intermediate 18 (200 mg, 0.558 mmol) with 6-chloronicotinonitrile (116 mg, 0.837 mmol) in the presence of $Cs_2CO_3$ (355 mg, 1.117 mmol) and CuI (22 mg, 0.111 mmol) in dry DMA (3 ml) as described in Example 1 to give 110 mg of the product as an off-white solid; IR (KBr) 2961, 2233, 1592, 1470, 1270, 1157, 781 cm$^{-1}$; $^1$H NMR (300 MHz, CDCl$_3$) δ 0.932 (t, J=7.2 Hz, 3H), 1.39-1.46 (m, 2H), 1.62-1.68 (m, 2H), 3.87 (s, 3H), 3.97 (t, J=6.3 Hz, 2H), 6.91 (t, J=6.9 Hz, 1H), 7.02-7.07 (m, 2H), 7.23-7.28 (m, 1H), 7.46 (t, J=7.5 Hz, 1H), 7.61 (d, J=8.1 Hz, 2H), 8.13 (d, J=16.2 Hz, 1H), 8.22 (d, J=7.8 Hz, 1H), 9.02 (s, 1H); ESI-MS (m/z) 461.40 (M+H)+.

Example 65

6-{5,6-Difluoro-2-[(E)-2-(2-pentoxy-3-methoxyphenyl)vinyl]-1H-benzimidazol-1-yl}nicotinonitrile

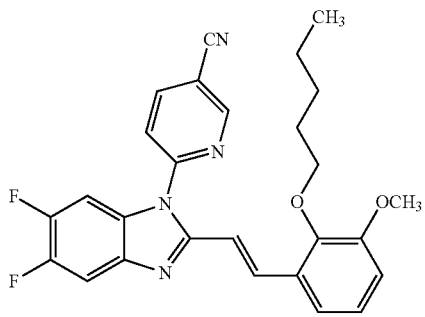 [SMILES: CCCCCOc1c(/C=C/c2nc3cc(F)c(F)cc3n2-c2ccc(C#N)cn2)cccc1OC]

The title compound was prepared by coupling Intermediate 19 (200 mg, 0.537 mmol) with 6-chloronicotinonitrile (112 mg, 0.806 mmol) in the presence of $Cs_2CO_3$ (350.2 mg, 1.074 mmol) and CuI (21 mg, 0.107 mmol) in dry DMA (5 ml) as described in Example 1 to give 93 mg of the product as an off-white solid; IR (KBr) 2956, 2236, 1593, 1471, 1270, 1159, 782 cm$^{-1}$; $^1$H NMR (300 MHz, DMSO-d$_6$) δ 0.88-0.9 (m, 3H), 1.32-1.39 (m, 4H), 1.62 (d, J=6.3 Hz, 2H), 3.81 (s, 3H), 3.91 (br s, 2H), 7.05 (s, 2H), 7.24-7.29 (m, 2H), 7.65-7.71 (m, 1H), 7.80-7.86 (m, 1H), 7.99 (d, J=7.8 Hz, 1H), 8.11 (d, J=15.9 Hz, 1H), 8.70 (d, J=6.3 Hz, 1H), 9.24 (s, 1H); APCI-MS (m/z) 475.22 (M+H)+.

Example 66

6-{5,6-Difluoro-2-[(E)-2-(2-isobutoxy-3-methoxyphenyl)vinyl]-1H-benzimidazol-1-yl}nicotinonitrile

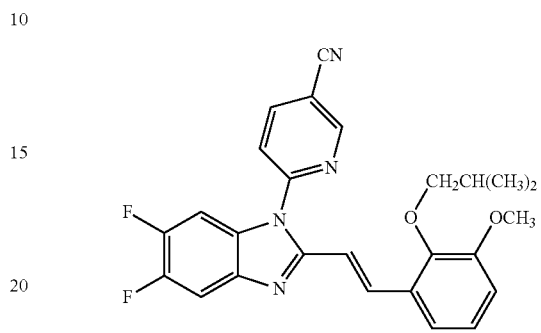

The title compound was prepared by coupling Intermediate 20 (200 mg, 0.55 mmol) with 6-chloronicotinonitrile (116 mg, 0.83 mmol) in the presence of $Cs_2CO_3$ (364 mg, 1.1 mmol) and CuI (22 mg, 0.11 mmol) in dry DMA (5 ml) as described in Example 1 to give 83 mg of the product as an off-white solid; IR (KBr) 2958, 2234, 1593, 1470, 1270, 1158, 779 cm$^{-1}$; $^1$H NMR (300 MHz, CDCl$_3$) δ 0.97 (d, J=6.3 Hz, 6H), 1.98-2.06 (m, 1H), 3.73 (d, J=6.9 Hz, 2H), 3.86 (s, 3H), 6.91 (d, J=6.3 Hz, 1H), 7.01-7.10 (m, 2H), 7.36 (s, 1H), 7.43-7.49 (m, 1H), 7.56-7.61 (m, 2H), 8.15 (d, J=16.3 Hz, 1H), 8.19-8.24 (m, 1H), 9.01 (s, 1H); ESI-MS (m/z) 461.25 (M+H)+.

Example 67

6-{2-[(E)-2-(2-Cyclobutylmethoxy-3-methoxyphenyl)vinyl]-5,6-difluoro-1H-benzimidazol-1-yl nicotinonitrile

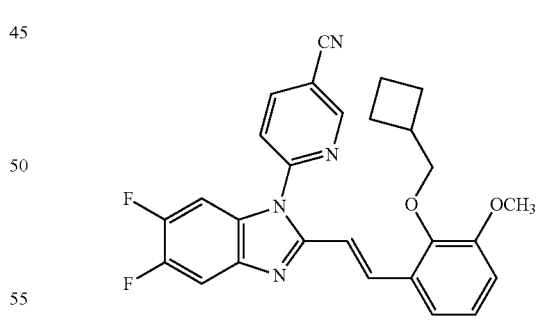

The title compound was prepared by coupling Intermediate 22 (200 mg, 0.54 mmol) with 6-chloronicotinonitrile (112 mg, 0.81 mmol) in the presence of $Cs_2CO_3$ (352.5 mg, 1.0 mmol) and CuI (20.6 mg, 0.10 mmol) in dry DMF (5 ml) as described in Example 1 to give 109 mg of the product as an off-white solid; IR (KBr) 2937, 2233, 1592, 1471, 1395, 1269, 1158, 782 cm$^{-1}$; $^1$H NMR (300 MHz, CDCl$_3$) δ 1.76-1.86 (m, 4H), 1.95-2.04 (m, 2H), 2.65-2.72 (m, 1H), 3.87 (s, 3H), 3.97 (d, J=6.9 Hz, 2H), 6.90 (t, J=6.3 Hz, 1H), 7.01-7.09 (m, 2H), 7.20 (s, 1H), 7.44-7.49 (m, 1H), 7.56-7.61 (m, 2H), 8.14 (d, J=15.6 Hz, 1H), 8.22 (d, J=7.8 Hz, 1H), 9.02 (s, 1H); APCI-MS (m/z) 473.27 (M+H)+.

Example 68

6-{2-[(E)-2-(2-Cyclopentyloxy-3-methoxyphenyl)vinyl]-5,6-difluoro-1H-benzimidazol-1-yl}nicotinonitrile

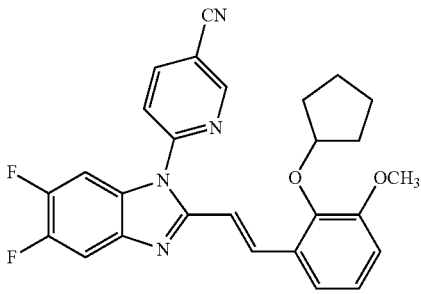 [SMILES: COc1cccc(/C=C/c2nc3cc(F)c(F)cc3n2-c2ccc(C#N)cn2)c1OC1CCCC1]

This compound was prepared by coupling Intermediate 23 (200 mg, 0.541 mmol) with 6-chloronicotinonitrile (112 mg, 0.811 mmol) in presence of $Cs_2CO_3$ (351 mg, 1.081 mmol) and CuI (20 mg, 0.108 mmol) in dry DMA (5 ml) as described in Example 1 to give 97 mg of the product as an off-white solid; $^1$H NMR (300 MHz, CDCl$_3$) δ 1.65-1.81 (m, 8H), 3.85 (s, 3H), 4.88 (br s, 1H), 6.87 (dd, J=1.5, 7.8 Hz, 1H), 6.97-7.07 (m, 2H), 7.17 (d, J=15.9 Hz, 1H), 7.39-7.45 (m, 1H), 7.54-7.60 (m, 2H), 8.11 (d, J=15.9 Hz, 1H), 8.20 (dd, J=2.7, 9.0 Hz, 1H), 8.99 (d, J=1.5 Hz, 1H); ESI-MS (m/z) 473.53 (M+H)+.

Example 69

6-{5,6-Difluoro-2-[(E)-2-(2-hydroxy-3-methoxyphenyl)vinyl]-1H-benzimadazol-1-yl}nicotinonitrile

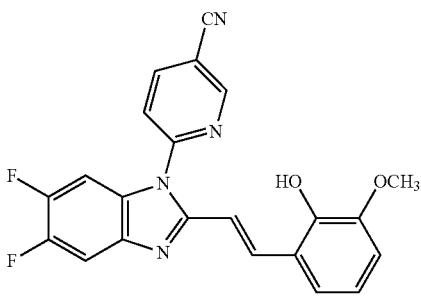 [SMILES: COc1cccc(/C=C/c2nc3cc(F)c(F)cc3n2-c2ccc(C#N)cn2)c1O]

To a well stirred solution of Example 68 (500 mg, 1.059 mmol) in dry DCM (20 ml), cooled to −70° C., was added boron tribromide (BBr$_3$) under nitrogen atmosphere and the reaction mixture was stirred for 30 minutes at −70° C. After completion of the reaction, the reaction mixture was neutralized with saturated NaHCO$_3$ solution and the precipitated solid was filtered. The crude product obtained was purified by silica gel column chromatography using 3% methanol in chloroform to give 35 mg of the product; IR (KBr) 2922, 2239, 1592, 1472, 1266, 1125, 769 cm$^{-1}$; $^1$H NMR (300 MHz, DMSO-d$_6$) δ 3.81 (s, 3H), 6.77 (t, J=7.8 Hz, 1H), 6.96 (d, J=7.8 Hz, 1H), 7.17-7.27 (m, 2H), 7.67 (d, J=7.2 Hz, 1H), 7.82 (t, J=7.8 Hz, 1H), 7.98 (d, J=8.1 Hz, 1H), 8.16 (d, J=15.6 Hz, 1H), 8.68 (d, J=8.4 Hz, 1H), 9.25 (d, J=15.9 Hz, 1H); APCI-MS (m/z) 405.37 (M+H)+

Example 70

6-{6-Chloro-2-[(E)-2-(2-[cyclopentyloxy]-3-methoxyphenyl)vinyl]-5-fluoro-1H-benzimidazol-1-yl}nicotinonitrile

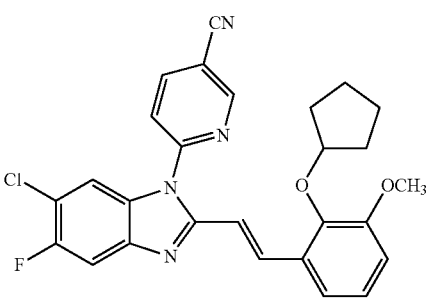 [SMILES: COc1cccc(/C=C/c2nc3cc(F)c(Cl)cc3n2-c2ccc(C#N)cn2)c1OC1CCCC1]

The title compound was prepared by cyclization of Intermediate 36 in glacial acetic acid as described in Example 52 to give 115 mg of the product as an off-white solid; IR (KBr) 2953, 2234, 1592, 1459, 1266, 1149, 757 cm$^{-1}$; $^1$H NMR (300 MHz, CDCl$_3$) δ 1.60-1.69 (m, 4H), 1.71-1.78 (m, 4H), 3.87 (s, 3H), 4.90 (br s, 1H), 6.91 (d, J=7.2 Hz, 1H), 7.00-7.10 (m, 2H), 7.20 (d, J=15.6 Hz, 1H), 7.56-7.65 (m, 3H), 8.20 (d, J=16.2 Hz, 2H), 9.03 (s, 1H); ESI-MS (m/z) 489.15 (M+H)+.

Example 71

6-{5-Chloro-2-[(E)-2-(2-cyclopentyloxy-3-methoxyphenyl)vinyl]-6-(trifluoromethyl)-1H-benzimidazol-1-yl}nicotinonitrile

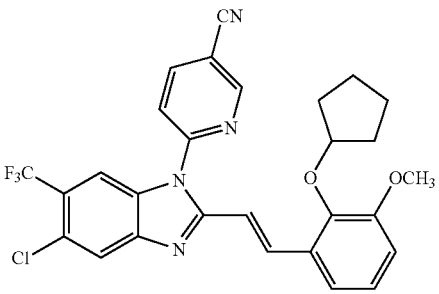 [SMILES: COc1cccc(/C=C/c2nc3cc(Cl)c(C(F)(F)F)cc3n2-c2ccc(C#N)cn2)c1OC1CCCC1]

The title compound was prepared by coupling Intermediate 26 (200 mg, 0.45 mmol) with 6-chloronicotinonitrile (96 mg, 0.68 mmol) in the presence of $Cs_2CO_3$ (299 mg, 0.91 mmol) and CuI (18 mg, 0.09 mmol) in dry DMA (5 ml) as described in Example 1 to give 45 mg of the product as an off-white solid; IR (KBr) 2963, 2232, 1591, 1478, 1269, 1132, 1072, 775 cm$^{-1}$; $^1$H NMR (300 MHz, CDCl$_3$) δ 1.60-1.70 (m, 4H), 1.75-1.82 (m, 4H), 3.87 (s, 3H), 4.92 (br s, 1H), 6.90-9.96 (m, 1H), 7.03-7.10 (m, 1H), 7.16-7.26 (m, 1H), 7.63 (d, J=8.4 Hz, 1H), 7.71 (s, 1H), 7.90-7.98 (m, 1H), 8.17 (s, 1H), 8.23-8.30 (m, 2H), 9.06 (s, 1H); APCI-MS (m/z) 539.17 (M+H)+.

Example 72

6-{5,6-Dichloro-2-[(E)-2-(2-cyclopentyloxy-3-methoxyphenyl)vinyl]-1H-benzimidazol-1-yl}nicotinonitrile

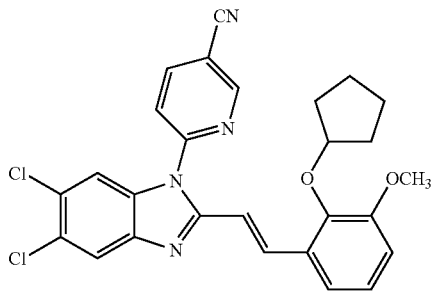 [SMILES: COc1cccc(/C=C/c2nc3cc(Cl)c(Cl)cc3n2-c2ccc(C#N)cn2)c1OC1CCCC1]

The title compound was prepared by coupling Intermediate 24 (200 mg, 0.497 mmol) with 6-chloronicotinonitrile (103 mg, 0.746 mmol) in the presence of Cs$_2$CO$_3$ (354 mg, 0.99 mmol) and CuI (20 mg, 0.099 mmol) in dry DMA (5 ml) as described in Example 1 to give 30 mg of the product as an off-white solid; IR (KBr) 2951, 2234, 1590, 1442, 1270, 1070, 776 cm$^{-1}$; $^1$H NMR (300 MHz, CDCl$_3$) δ 1.66-1.79 (m, 8H), 3.87 (s, 3H), 4.91 (br s, 1H), 6.91 (d, J=7.2 Hz, 1H), 7.00-7.10 (m, 2H), 7.17-7.26 (m, 1H), 7.61 (d, J=8.4 Hz, 1H), 7.71 (s, 1H), 7.91 (s, 1H), 8.18-8.26 (m, 2H), 9.04 (s, 1H); ESI-MS (m/z) 505.14 (M+H)+.

Example 73

Ethyl 6-{2-[(E)-2-(2-cyclopentyloxy-3-methoxyphenyl)vinyl]-5,6-difluoro-1H-benzimidazol-1-yl}pyridazine-3-carboxylate

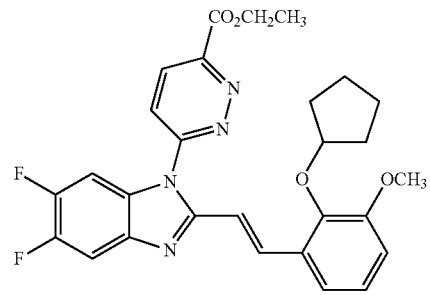

The title compound was prepared by coupling Intermediate 23 (2.0 g, 5.13 mmol) with ethyl 6-chloropyridazine-3-carboxylate (1.5 g, 7.699 mmol) in the presence of Cs$_2$CO$_3$ (3.4 g, 10.36 mmol) and CuI (0.20 g, 1.023 mmol) in dry DMA (20 ml) as described in Example 1 to give 710 mg of the product as an off-white solid; IR (KBr) 2955, 2233, 1728, 1576, 1465, 1269, 1155, 773 cm$^{-1}$; $^1$H NMR (300 MHz, CDCl$_3$) δ 1.58-1.66 (m, 8H), 1.68-1.79 (m, 3H), 3.86 (s, 3H), 4.59-4.66 (m, 2H), 4.88 (br s, 1H), 6.90 (d, J=7.8 Hz, 1H), 7.02 (t, J=7.8 Hz, 1H), 7.08-7.18 (m, 2H), 7.52-7.65 (m, 2H), 7.80 (d, J=8.7 Hz, 1H), 8.17 (d, J=16.2 Hz, 1H), 8.45 (d, J=8.7 Hz, 1H); ESI-MS (m/z) 521.23 (M+H)+.

Example 74

6-{2-[(E)-2-(2-Cyclopentyloxy-3-methoxyphenyl)vinyl]-5,6-difluoro-1H-benzimidazol-1-yl}pyridazine-3-carboxylic acid

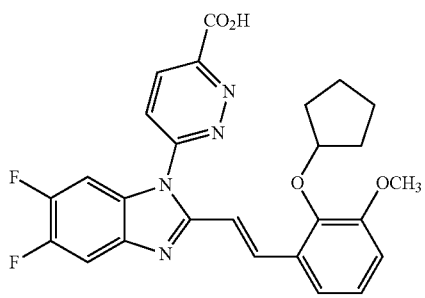 [SMILES: COc1cccc(/C=C/c2nc3cc(F)c(F)cc3n2-c2ccc(C(=O)O)nn2)c1OC1CCCC1]

The title compound was prepared by lithium hydroxide (97 mg, 2.30 mmol) assisted hydrolysis of Example 73 (601 mg, 0.528 mmol) as described in Step 1 of Example 20 to yield 210 mg of yellow solid; IR (KBr) 3427, 2954, 2233, 1623, 1575, 1477, 1267, 1145, 775 cm$^{-1}$; $^1$H NMR (300 MHz, DMSO-d$_6$) δ 1.65-1.75 (m, 8H), 3.81 (s, 3H), 4.87 (br s, 1H), 7.05 (s, 2H), 7.15 (s, 1H), 7.20 (s, 1H), 7.67 (t, J=7.8 Hz, 1H), 7.89 (t, J=7.8 Hz, 1H), 8.14 (d, J=16.2 Hz, 1H), 8.26 (d, J=9.0, 1H), 8.53 (d, J=8.7, 1H); ESI-MS (m/z) 492.22 (M)+.

Example 75

6-{2-[(E)-2-(2-Cyclopentyloxy-3-methoxyphenyl)vinyl]-5,6-difluoro-1H-benzimidazol-1-yl}pyridazine-3-carboxamide

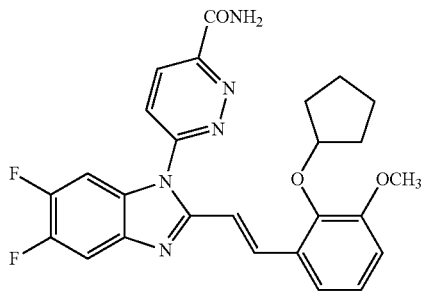 [SMILES: COc1cccc(/C=C/c2nc3cc(F)c(F)cc3n2-c2ccc(C(N)=O)nn2)c1OC1CCCC1]

The title compound was prepared from Example 74 (200 mg, 0.43 mmol) by mixed anhydride method as described in Step 2 of Example 20 to get 285 mg of product as a yellow solid; IR (KBr) 3410, 2962, 1693, 1477, 1264, 1066, 738 cm$^{-1}$; $^1$H NMR (300 MHz, DMSO-d$_6$) δ 1.64-1.74 (m, 8H), 3.81 (s, 3H), 4.87 (br s, 1H), 7.05 (br s, 2H), 7.16-7.26 (m, 2H), 7.66 (t, J=7.2 Hz, 1H), 7.90 (t, J=7.5 Hz, 1H), 8.14 (d, J=15.6 Hz, 2H), 8.32 (d, J=8.7, 1H), 8.52 (d, J=8.7, 1H), 8.83 (s, 1H); ESI-MS (m/z) 491.22 (M)+.

Example 76

6-{2-[(E)-2-(2-Cyclopentyloxy-3-methoxyphenyl)vinyl]-5,6-difluoro-1H-benzimidazol-1-yl}pyridazine-3-carbonitrile

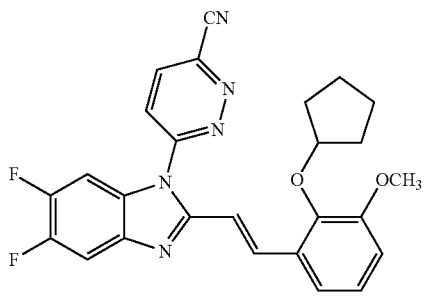 [SMILES: COc1cccc(/C=C/c2nc3cc(F)c(F)cc3n2-c2ccc(C#N)nn2)c1OC1CCCC1]

The title compound was prepared by dehydration Example 75 (200 mg, 0.40 mmol) using trifluoroacetic anhydride (128.5 mg, 0.610 mmol) in the presence of triethylamine (124 mg, 1.22 mmol) as described in Step 3 of Example 20 to give 79 mg of the product as an off-white solid; IR (KBr) 2957, 1623, 1574, 1474, 1269, 757 cm$^{-1}$; $^1$H NMR (300 MHz, DMSO-d$_6$) δ 1.62-1.79 (m, 8H), 3.81 (s, 3H), 4.88 (br s, 1H), 7.06 (s, 2H), 7.15 (d, J=16.2 Hz, 1H), 7.27 (s, 1H), 7.65-7.71 (m, 1H), 7.88-7.94 (m, 1H), 8.17 (d, J=16.2 Hz, 1H), 8.47 (d, J=9.3, 1H), 8.78 (d, J=8.7, 1H); APCI-MS (m/z) 474.17 (M+H)$^+$.

Example 77

6-{2-[(E)-2-(2-(1-ethylpropoxy)-3-methoxyphenyl)vinyl]-5,6-difluoro-1H-benzimidazol-1-yl}nicotinonitrile

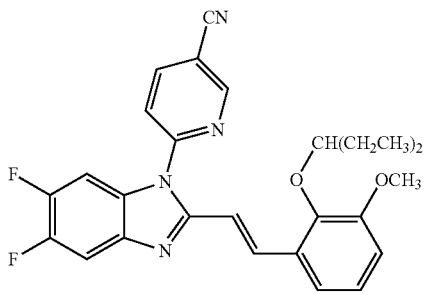

The title compound was prepared by coupling Intermediate 21 (301 mg, 0.809 mmol) with 6-chloronicotinonitrile (168 mg, 1.209 mmol) in the presence of Cs$_2$CO$_3$ (525 mg, 1.612 mmol) and CuI (30.8 mg, 0.161 mmol) in dry DMA (5 ml) as described in Example 1 to give 169 mg of the product as an off-white solid; IR (KBr) 2965, 2235, 1593, 1471, 1268, 1073, 771 cm$^{-1}$; $^1$H NMR (300 MHz, CDCl$_3$) δ 1.58-1.67 (m, 10H), 3.86 (s, 3H), 4.23 (t, J=6.0 Hz, 1H), 6.90 (d, J=7.8 Hz, 1H), 7.01 (t, J=7.8 Hz, 1H), 7.08 (d, J=7.8 Hz, 1H), 7.17-7.25 (m, 1H), 7.42-7.47 (m, 1H), 7.55-7.61 (m, 2H), 8.14 (s, 1H), 8.17-8.23 (m, 1H), 9.02 (s, 1H); ESI-MS (m/z) 475.21 (M)$^+$.

Example 78

6-{5,7-Difluoro-2-[(E)-2-(2-pentyloxy-3-methoxyphenyl)vinyl]-1H-benzimidazol-1-yl}nicotinonitrile

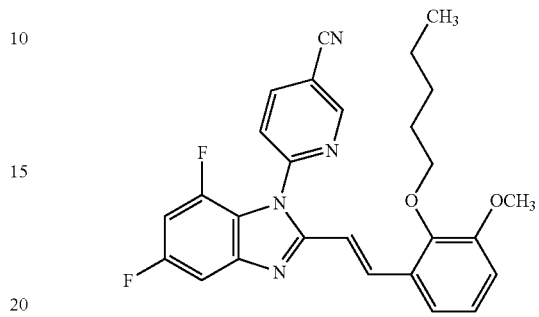

The title compound was prepared by cyclization of Intermediate 37 in glacial acetic acid as described in Example 52 to give 33 mg of the product as an off-white solid; IR (KBr) 3020, 2935, 2238, 1600, 1477, 1217, 1125, 771 cm$^{-1}$; $^1$H NMR (300 MHz, CDCl$_3$) δ 0.85-0.95 (m, 3H), 1.30-1.40 (m, 4H), 1.69-1.74 (m, 2H), 3.86 (s, 3H), 3.95 (t, J=6.9 Hz, 2H), 6.81 (t, J=10.2 Hz, 1H), 6.90 (d, J=5.4 Hz, 1H), 7.00-7.06 (m, 2H), 7.19 (d, J=15.9 Hz, 1H), 7.33 (d, J=8.1 Hz, 1H), 7.57-7.62 (m, 1H), 8.18 (m, 2H), 8.97 (s, 1H); APCI-MS (m/z) 475.42 (M+H)$^+$.

Example 79

6-{5,7-Difluoro-2-[(E)-2-(2-[cyclopentyloxy]-3-methoxyphenyl)vinyl]-1H-benzimidazol-1-yl}nicotinonitrile

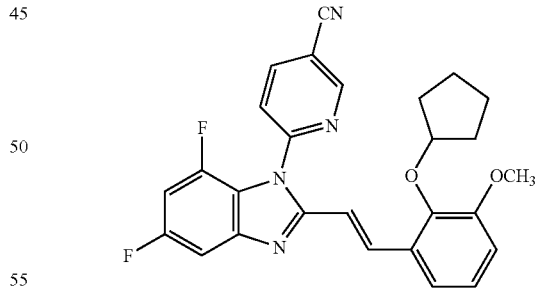

The title compound was prepared by cyclization of intermediate 38 in glacial acetic acid as described in Example 52 to give 39 mg of the product as an off-white solid; IR (KBr) 3020, 2400, 2238, 1600, 1499, 1215, 1126, 758 cm$^{-1}$; $^1$H NMR (300 MHz, CDCl$_3$) δ 1.67-1.78 (m, 8H), 3.86 (s, 3H), 4.88 (br s, 1H), 6.80 (t, J=9.3 Hz, 1H), 6.89 (d, J=6.9 Hz, 1H), 7.01-7.06 (m, 2H), 7.15 (d, J=15.9 Hz, 1H), 7.33 (d, J=8.4 Hz, 1H), 7.56-7.62 (m, 1H), 8.17-8.22 (m, 2H), 8.97 (s, 1H); APCI-MS (m/z) 473.42 (M+H)$^+$.

Example 80

6-{4,6-Difluoro-2-[(E)-2-(2-[cyclopentyloxy]-3-methoxyphenyl)vinyl]-1H-benzimidazol-1-yl}nicotinonitrile

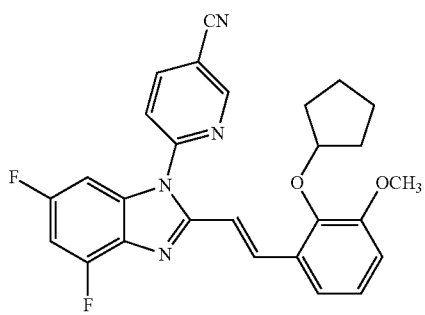 [SMILES: COc1cccc(/C=C/c2nc3c(F)cc(F)cc3n2-c2ccc(C#N)cn2)c1OC1CCCC1]

This compound was prepared by coupling Intermediate 27 (200 mg, 0.540 mmol) with 6-chloronicotinonitrile (113 mg, 0.810 mmol) in the presence of $Cs_2CO_3$ (352 mg, 1.081 mmol) and CuI (22 mg, 0.108 mmol) in dry DMA (3 ml) as described in Example 1 to give the crude product. This product was further recrystallized from ethyl acetate to obtain 91 mg of the desired regioisomer as an off-white solid; IR (KBr) 2956, 2232, 1592, 1429, 1225, 1069, 772 cm$^{-1}$; $^1$H NMR (300 MHz, DMSO-d$_6$) δ 1.60-1.75 (m, 8H), 3.81 (s, 3H), 4.88 (br s, 1H), 7.06 (s, 2H), 7.24-7.30 (m, 4H), 8.00 (d, J=8.4 Hz, 1H), 8.14 (d, J=15.9 Hz, 1H), 8.71 (d, J=7.8 Hz, 1H), 9.25 (s, 1H); APCI-MS (m/z) 473.17 (M+H)$^+$.

Example 81

6-{2-[(E)-2-(2-pentyloxy-3-methoxyphenyl)vinyl]-4,5,6-trifluoro-1H-benzimidazol-1-yl}nicotinonitrile

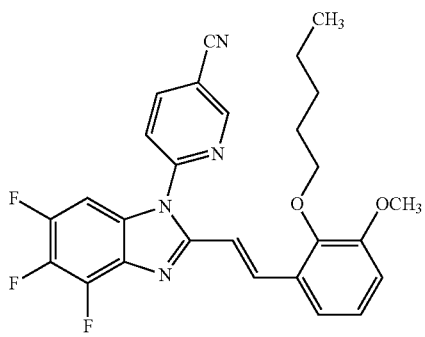 [SMILES: CCCCCOc1c(/C=C/c2nc3c(F)c(F)c(F)cc3n2-c2ccc(C#N)cn2)cccc1OC]

The title compound was prepared by coupling Intermediate 28 (200 mg, 0.537 mmol) with 6-chloronicotinonitrile (112 mg, 0.806 mmol) in the presence of $Cs_2CO_3$ (350.2 mg, 1.074 mmol) and CuI (21 mg, 0.107 mmol) in dry DMA (5 ml) as described in Example 1 to give the crude product. This product was further recrystallized from ethyl acetate to obtain 93 mg of the desired regioisomer as an off-white solid; IR (KBr) 2935, 2236, 1578, 1480, 1271, 1074, 778 cm$^{-1}$; $^1$H NMR (300 MHz, DMSO-d$_6$) δ 0.910 (t, J=6.0 Hz, 3H), 1.32-1.39 (m, 4H), 1.62 (br s, 2H), 3.81 (s, 3H), 3.92 (br s, 2H), 7.06 (s, 1H), 7.21 (s, 2H), 7.57 (br s, 1H), 8.00 (d, J=6.0 Hz, 1H), 8.17 (d, J=15.0 Hz, 1H), 8.72 (d, J=6.0 Hz, 1H), 9.25 (br s, 1H); ESI-MS (m/z) 493.27 (M+H)$^+$.

Example 82

6-(2-{(E)-2-[3-(Difluoromethoxy)-2-pentyloxyphenyl]vinyl}-5,6-difluoro-1H-benzimidazol-1-yl)nicotinonitrile

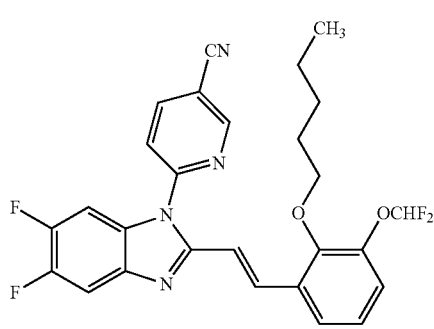 [SMILES: CCCCCOc1c(/C=C/c2nc3cc(F)c(F)cc3n2-c2ccc(C#N)cn2)cccc1OC(F)F]

The title compound was prepared by coupling Intermediate 29 (150 mg, 0.36 mmol) with 6-chloronicotinonitrile (66.2 mg, 0.47 mmol) in the presence of $Cs_2CO_3$ (239.5 mg, 0.73 mmol) and CuI (14 mg, 0.073 mmol) in dry DMA (3 ml) as described in Example 1 to give 53 mg of the product as an off-white solid; IR (KBr) 2933, 2233, 1592, 1473, 1267, 1122, 795 cm$^{-1}$; $^1$H NMR (300 MHz, CDCl$_3$) δ 0.93 (br s, 3H), 1.39 (br s, 4H), 1.73 (br s, 2H), 4.00 (br s, 2H), 6.55 (d, J=74.7 Hz, 1H), 7.10 (d, J=7.8 Hz, 1H), 7.17 (d, J=7.8 Hz, 1H), 7.22 (s, 1H), 7.36 (d, J=6.9 Hz, 1H), 7.44 (t, J=7.2 Hz, 1H), 7.61 (d, J=7.8 Hz, 2H), 8.15 (d, J=15.6 Hz, 1H), 8.25 (d, J=6.9 Hz, 1H), 9.03 (s, 1H); ESI-MS (m/z) 511.15 (M+H)$^+$.

Example 83

6-(2-{(E)-2-[2-(Cyclobutylmethoxy)-3-difluoromethoxyphenyl]vinyl}-5,6-difluoro-1H-benzimidazol-1-yl)nicotinonitrile

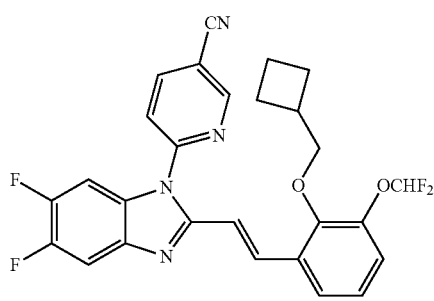 [SMILES: N#Cc1ccc(-n2c(/C=C/c3cccc(OC(F)F)c3OCC3CCC3)nc3cc(F)c(F)cc32)nc1]

The title compound was prepared by coupling Intermediate 30 (200 mg, 0.558 mmol) with 6-chloronicotinonitrile (116 mg, 0.837 mmol) in the presence of $Cs_2CO_3$ (355 mg, 1.117 mmol) and CuI (22 mg, 0.111 mmol) in dry DMA (3 ml) as described in Example 1 to give 110 mg of the product as an off-white solid; IR (KBr) 2929, 2238, 1471, 1269, 1124, 758 cm$^{-1}$; $^1$H NMR (300 MHz, CDCl$_3$) δ 1.80-1.92 (m, 4H), 2.04 (br s, 2H), 3.99 (d, J=6.3 Hz, 2H), 6.55 (t, J=74.4 Hz, 1H), 7.09 (d, J=7.8 Hz, 1H), 7.14-7.21 (m, 2H), 7.36 (d, J=6.9 Hz, 1H), 7.44 (t, J=7.2 Hz, 1H), 7.61 (br s, 2H), 8.14 (d, J=16.2 Hz, 1H), 8.25 (d, J=7.8 Hz, 2H), 9.03 (s, 1H); ESI-MS (m/z) 509.08 (M+H)+.

Example 84

6-(2-{(E)-2-[2-(Cyclopentyloxy)-3-difluoromethoxyphenyl-]vinyl}-5,6-difluoro-1H-benzimidazol-1-yl)nicotinonitrile

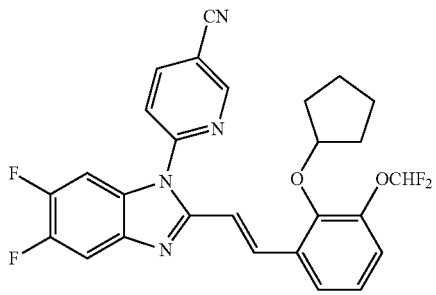 [SMILES: N#Cc1ccc(-n2c(/C=C/c3cccc(OC(F)F)c3OC3CCCC3)nc3cc(F)c(F)cc32)nc1]

The title compound was prepared by coupling Intermediate 31 (200 mg, 0.492 mmol) with 6-chloronicotinonitrile (102 mg, 0.738 mmol) in the presence of Cs$_2$CO$_3$ (320 mg, 0.98 mmol) and CuI (18 mg, 0.098 mmol) in dry DMA (5 ml) as described in Example 1 to give 119 mg of the product as an off-white solid; IR (KBr) 2961, 2236, 1590, 1462, 1121, 1036, 770 cm$^{-1}$; $^1$H NMR (300 MHz, CDCl$_3$) δ 1.59-1.66 (m, 4H), 1.70-1.82 (m, 4H), 4.84 (br s, 1H), 6.53 (t, J=74.7 Hz, 1H), 7.06 (t, J=7.8 Hz, 1H), 7.15 (d, J=7.2 Hz, 1H), 7.24 (d, J=12.6 Hz, 1H), 7.35-7.45 (m, 2H), 7.61 (br s, 2H), 8.16 (d, J=15.9 Hz, 1H), 8.26 (br s, 1H), 9.03 (s, 1H); ESI-MS (m/z) 509.14 (M+H)+.

Example 85

2-[(E)-2-(2-butoxy-3-methoxyphenyl)vinyl]-1-(5-trifluoromethylpyridin-2-yl)-1H-benzimidazole

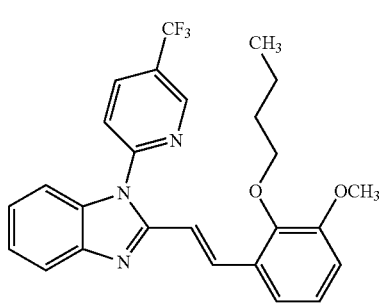

The title compound was prepared by coupling Intermediate 2 (200 mg, 0.625 mmol) with 2-chloro-5-(trifluoromethyl)pyridine (169 mg, 0.931 mmol) in presence of Cs$_2$CO$_3$ (405 mg, 1.242 mmol) and CuI (24 mg, 0.124 mmol) in dry DMA (3 ml) as described in Example 1 to give 45 mg of the product as an off-white solid; IR (KBr) 2964, 1579, 1375, 1267, 1137, 717 cm$^{-1}$; $^1$H NMR (300 MHz, CDCl$_3$) δ 0.90 (t, J=7.2 Hz, 3H), 1.34-1.44 (m, 2H), 1.60-1.68 (m, 2H), 3.84 (s, 3H), 3.94 (t, J=6.3 Hz, 2H), 6.86 (d, J=7.5 Hz, 1H), 6.99-7.09 (m, 2H), 7.27-7.39 (m, 3H), 7.50 (d, J=7.8 Hz, 1H), 7.61 (d, J=8.4 Hz, 1H), 7.82 (d, J=7.8 Hz, 1H), 8.14 (d, J=15.3 Hz, 1H), 8.18 (s, 1H), 8.99 (s, 1H); ESI-MS (m/z) 468.31 (M+H)+.

Example 86

6-{2-[(E)-2-(2-Butoxy-3-methoxyphenyl)vinyl]-3H-imidazo[4,5-b]pyridin-3-yl}nicotinonitrile

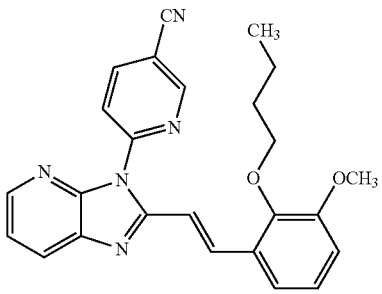

The title compound was prepared by cyclization of Intermediate 40 in glacial acetic acid as described in Example 52 to give 219 mg of the product as an off-white solid; IR (KBr) 2952, 2233, 1578, 1479, 1271, 1048 cm$^{-1}$; $^1$H NMR (300 MHz, DMSO-d$_6$) δ 0.88-0.95 (m, 3H), 1.39-1.46 (m, 2H), 1.59-1.68 (m, 2H), 3.82 (s, 3H), 3.91-3.98 (m, 2H), 7.08 (s, 2H), 7.29 (br s, 1H), 7.42-7.55 (m, 2H), 8.18-8.27 (m, 3H), 8.36 (br s, 1H), 8.60-8.73 (m, 1H), 9.22 (s, 1H); APCI-MS (m/z) 426.30 (M+H)+.

Example 87

6-{2-[(E)-2-(2-Pentyloxy-3-methoxyphenyl)vinyl]-3H-imidazo[4,5-b]pyridin-3-yl}nicotinonitrile

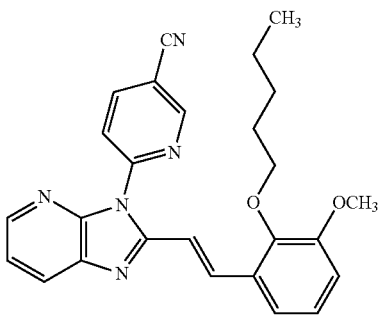 [SMILES: CCCCCOc1c(/C=C/c2nc3cccnc3n2-c2ccc(C#N)cn2)cccc1OC]

The title compound was prepared by cyclization of Intermediate 41 in glacial acetic acid as described in Example 52 to give 131 mg of the product as an off-white solid; IR (KBr) 2930, 2232, 1592, 1479, 1368, 1269, 1075 cm$^{-1}$; $^1$H NMR (300 MHz, CDCl$_3$) δ 0.921 (s, 3H), 1.37-1.42 (m, 2H), 1.56 (br s, 2H), 1.77 (br s, 2H), 3.87 (s, 3H), 4.00 (br s, 2H), 6.91 (d, J=7.2 Hz, 1H), 7.06 (t, J=7.8 Hz, 1H), 7.17 (d, J=7.8 Hz, 1H), 7.34 (br s, 1H), 7.68 (d, J=16.2 Hz, 1H), 8.10 (d, J=6.9 Hz, 1H), 8.26-8.34 (m, 4H), 8.97 (s, 1H); APCI-MS (m/z) 440.23 (M+H)+.

Example 88

6(2-{(E)-2-[3-methoxy-2-(pentyloxy)phenyl]ethenyl}-4-oxido-3H-imidazo[4,5-b]pyridin-3-yl)pyridine-3-carbonitrile

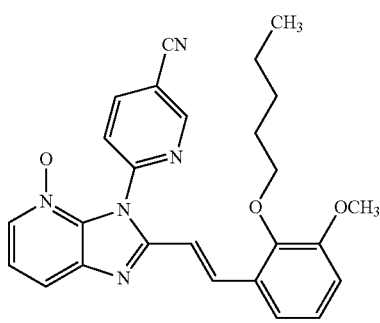

To a well stirred solution of Example 87 (150 mg, 0.341 mmol) in acetic acid (5 ml) was added m-chloroperbenzoic acid (117.2 mg, 0.683 mmol) and the reaction mixture was stirred at room temperature for 12 h. After completion of the reaction, the reaction mixture was diluted with water (20 ml) and extracted with ethyl acetate (2×25 ml). The combined organic layers were then washed with water (3×20 ml), brine (20 ml) and dried over $Na_2SO_4$, filtered and concentrated under reduced pressure. The crude product obtained was purified by silica gel column chromatography using 1.5% methanol in chloroform ether to give 39 mg of the product; $^1$H NMR (300 MHz, DMSO-$d_6$) δ 0.90 (t, J=6.3 Hz, 3H), 1.33-1.39 (m, 4H), 1.58 (br s, 2H), 3.89 (br s, 2H), 6.93 (d, J=16.2 Hz, 1H), 7.07 (br s, 2H), 7.21 (br s, 1H), 7.38 (t, J=7.2 Hz, 1H), 7.81 (d, J=8.4 Hz, 1H), 7.97 (d, J=8.1 Hz, 1H), 8.16-8.21 (m, 2H), 8.61 (d, J=8.4 Hz, 1H), 9.12 (s, 1H); APCI-MS (m/z) 456.20 (M+H)$^+$.

Example 89

6-{2-[(E)-2-(2-[Cyclopropylmethoxy]-3-methoxyphenyl)vinyl]-3H-imidazo[4,5-b]pyridin-3-yl}nicotinonitrile

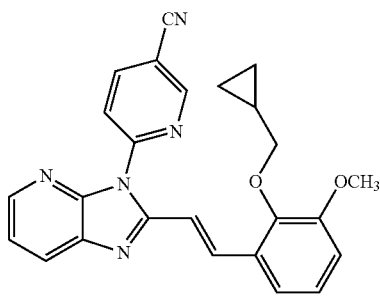 [SMILES: COc1cccc(/C=C/c2nc3cccnc3n2-c2ccc(C#N)cn2)c1OCC1CC1]

The title compound was prepared by cyclization of Intermediate 42 in glacial acetic acid as described in Example 52 to give 119 mg of the product as an off-white solid; IR (KBr) 3063, 2951, 2238, 1629, 1591, 1476, 1267, 977 cm$^{-1}$; $^1$H NMR (300 MHz, CDCl$_3$) δ 0.26 (d, J=4.8 Hz, 2H), 0.53 (d, J=7.2 Hz, 2H), 1.6 (br s, 1H), 3.87 (s, 5H), 6.90 (d, J=4.8 Hz, 1H), 7.06 (t, J=7.8 Hz, 1H), 7.16 (d, J=7.2 Hz, 1H), 7.30-7.36 (m, 1H), 7.71 (d, J=16.2 Hz, 1H), 8.11 (d, J=7.8 Hz, 1H), 8.23-8.29 (m, 2H), 8.32-8.40 (m, 2H), 8.97 (s, 1H); APCI-MS (m/z) 424.21 (M+H)$^+$

Example 90

6-[2-{(E)-2-[2-(Cyclobutylmethoxy)-3-methoxyphenyl]vinyl}-3H-imidazo[4,5-b]pyridine-3-yl]nicotinonitrile

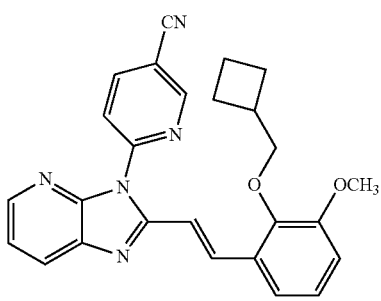 [SMILES: COc1cccc(/C=C/c2nc3cccnc3n2-c2ccc(C#N)cn2)c1OCC1CCC1]

The title compound was prepared by cyclization of Intermediate 43 in glacial acetic acid as described in Example 52 to give 153 mg of the product as an off-white solid; IR (KBr) 2934, 2241, 1591, 1475, 1384, 1267, 1074, 990 cm$^{-1}$; $^1$H NMR (300 MHz, DMSO-$d_6$) δ 1.83 (s, 4H), 2.03 (d, J=5.7 Hz, 2H), 2.66 (br s, 1H), 3.82 (s, 3H), 3.94 (d, J=6.3 Hz, 2H), 7.07 (s, 1H), 7.29 (br s, 1H), 7.42-7.46 (m, 2H), 7.52 (s, 1H), 8.19 (br s, 2H), 8.25 (d, J=7.2 Hz, 1H), 8.36 (s, 1H), 8.70 (d, J=7.8 Hz, 1H), 9.23 (s, 1H); ESI-MS (m/z) 438.18 (M+H)$^+$.

Example 91

6-{2-[(E)-2-(2-[Cyclopentyloxy]-3-methoxyphenyl)vinyl]-3H-imidazo[4,5-b]pyridin-3-yl}nicotinonitrile

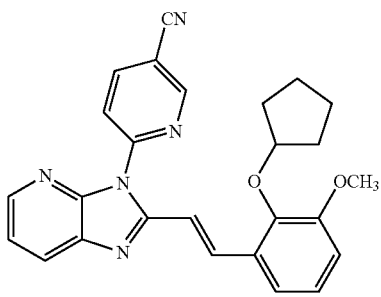 [SMILES: COc1cccc(/C=C/c2nc3cccnc3n2-c2ccc(C#N)cn2)c1OC1CCCC1]

The title compound was prepared by cyclization of Intermediate 39 in glacial acetic acid as described in Example 52 to give 27 mg of the product as an off-white solid; $^1$H NMR (300 MHz, CDCl$_3$) δ 1.68-1.74 (m, 4H), 1.76-1.86 (m, 4H), 3.87 (s, 3H), 4.90 (br s, 1H), 6.91 (t, J=7.5 Hz, 1H), 6.03 (d, J=7.8 Hz, 1H), 7.10 (t, J=7.8 Hz, 1H), 7.21 (s, 1H), 7.54 (d, J=7.8 Hz, 1H), 7.61-7.67 (m, 2H), 8.11 (s, 1H), 8.20-8.28 (m, 2H), 9.04 (s, 1H); APCI-MS (m/z) 438.13 (M+H)$^+$.

Example 92

6 (2-{(E)-2-[2-(cyclopentyloxy)-3-methoxyphenyl]ethenyl}-4-oxido-3H-imidazo[4,5-b]pyridin-3-yl)pyridine-3-carbonitrile

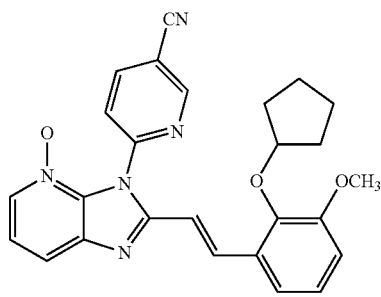

The title compound was prepared from Example 91 (80 mg, 0.183 mmol) in acetic acid (3 ml) using m-chloroperbenzoic acid (64 mg, 0.365 mmol) as described in Example 88 to give 26 mg of the product as an off-white solid; $^1$H NMR (300 MHz, DMSO-d$_6$) δ 1.55-1.65 (m, 4H), 1.65-1.75 (m, 4H), 3.81 (s, 3H), 4.88 (br s, 1H), 6.89 (d, J=15.9 Hz, 1H), 7.06 (br s, 2H), 7.21 (d, J=6.6 Hz, 1H), 7.36 (t, J=7.2 Hz, 1H), 7.83 (d, J=8.1 Hz, 1H), 7.94 (d, J=7.8 Hz, 1H), 8.15 (d, J=6.9 Hz, 1H), 8.22 (s, 1H), 8.60 (d, J=8.4 Hz, 1H), 9.12 (s, 1H); APCI-MS (m/z) 454.13 (M+H)$^+$.

Example 93

6-{6-Chloro-2-[(E)-2-(2-pentyloxy-3-methoxyphenyl)vinyl]-3H-imidazo[4,5-b]pyridin-3-yl}nicotinonitrile

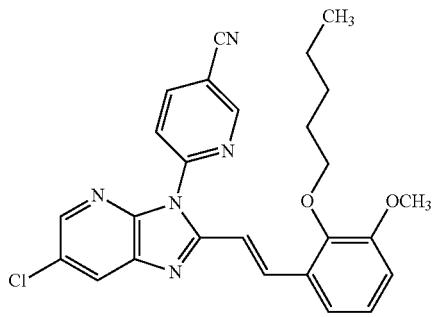 [SMILES: CCCCCOc1c(/C=C/c2nc3cc(Cl)cnc3n2-c2ccc(C#N)cn2)cccc1OC]

The title compound was prepared by cyclization of Intermediate 45 in glacial acetic acid as described in Example 52 to give 143 mg of the product as an off-white solid; IR (KBr) 2959, 2253, 1589, 1477, 1267, 1081, 734 cm$^{-1}$; $^1$H NMR (300 MHz, CDCl$_3$) δ 0.926 (t, J=6.9 Hz, 3H), 1.35-1.44 (m, 4H), 1.77 (t, J=6.6 Hz, 2H), 3.87 (s, 3H), 4.00 (t, J=6.9 Hz, 2H), 6.92 (d, J=7.8 Hz, 1H), 7.06 (t, J=7.8 Hz, 1H), 7.16 (d, J=7.2 Hz, 1H), 7.66 (d, J=16.2 Hz, 1H), 8.09 (s, 1H), 8.21-8.29 (m, 2H), 8.39 (d, J=16.2 Hz, 1H), 8.97 (s, 1H); APCI-MS (m/z) 474.30 (M+H)$^+$.

Example 94

6-(6-Chloro-2-{(E)-2-[2-(cyclobutylmethoxy)-3-methoxyphenyl]vinyl}-3H-imidazo[4,5-b]pyridin-3-yl)nicotinonitrile

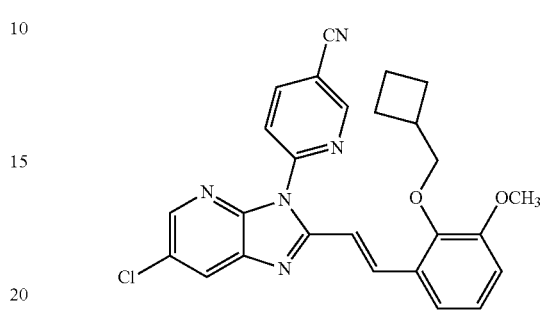

The title compound was prepared by cyclization of Intermediate 46 in glacial acetic acid as described in Example 52 to give 58 mg of the product as an off-white solid; IR (Neat) 3019, 2238, 1589, 1404, 1215, 758 cm$^{-1}$; $^1$H NMR (300 MHz, CDCl$_3$) δ 1.80-1.94 (m, 4H), 2.06-2.12 (m, 2H), 2.70-2.79 (m, 1H), 3.87 (s, 3H), 4.01 (d, J=6.9 Hz, 2H), 6.91 (d, J=7.8 Hz, 1H), 7.05 (t, J=8.1 Hz, 1H), 7.15 (d, J=7.5 Hz, 1H), 7.62 (d, J=16.2 Hz, 1H), 8.07 (s, 1H), 8.21-8.31 (m, 3H), 8.36 (s, 1H), 8.97 (s, 1H); ESI-MS (m/z) 472.21 (M+H)$^+$.

Example 95

6-{6-Chloro-2-[(E)-2-(2-(cyclopentyloxy)-3-methoxyphenyl)vinyl]-3H-imidazo[4,5-b]pyridin-3-yl}nicotinonitrile

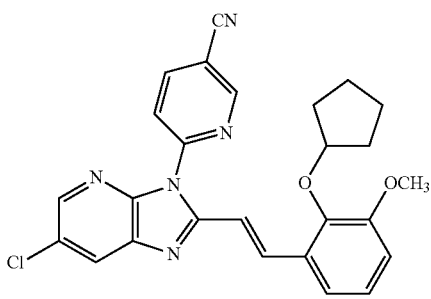 [SMILES: COc1cccc(/C=C/c2nc3cc(Cl)cnc3n2-c2ccc(C#N)cn2)c1OC1CCCC1]

The title compound was prepared by cyclization of Intermediate 47 in glacial acetic acid as described in Example 52 to give 52 mg of the product as an off-white solid; IR (KBr) 2962, 2227, 1575, 1477, 1266, 1070, 771 cm$^{-1}$; $^1$H NMR (300 MHz, DMSO-d$_6$) δ 1.60-1.70 (m, 4H), 1.71-1.77 (m, 4H), 3.82 (s, 3H), 4.89 (br s, 1H), 7.08 (s, 2H), 7.30 (s, 1H), 7.43 (d, J=16.2 Hz, 1H), 8.18-8.23 (m, 1H), 8.29 (s, 1H), 8.38 (s, 2H), 8.71 (d, J=7.8 Hz, 1H), 9.23 (s, 1H); APCI-MS (m/z) 472.21 (M+H)$^+$.

Example 96

6-(2-{(E)-2-[3-(Difluoromethoxy)-2-pentyloxyphenyl]vinyl}-3H-imidazo[4,5-b]pyridin-3-yl)nicotinonitrile

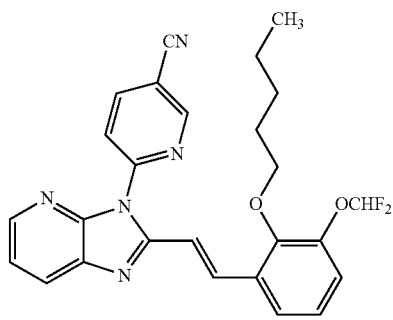 [SMILES: CCCCCOc1c(/C=C/c2nc3cccnc3n2-c2ccc(C#N)cn2)cccc1OC(F)F]

The title compound was prepared by cyclization of Intermediate 48 in glacial acetic acid as described in Example 52 to give 71 mg of the product as an off-white solid; IR (KBr) 2927, 2236, 1638, 1413, 1215, 757 cm$^{-1}$; $^1$H NMR (300 MHz, CDCl$_3$) δ 0.928 (t, J=6.9 Hz, 3H), 1.33-1.47 (m, 4H), 1.74-1.81 (m, 2H), 4.02 (t, J=6.9 Hz, 2H), 6.56 (t, J=74.7 Hz, 1H), 7.10 (t, J=7.8 Hz, 1H), 7.17 (d, J=7.2 Hz, 1H), 7.34-7.39 (m, 1H), 7.45 (d, J=7.5 Hz, 1H), 7.72 (d, J=16.2 Hz, 1H), 8.12 (d, J=7.2 Hz, 1H), 8.26-8.31 (m, 2H), 8.33-8.38 (m, 2H), 8.96 (s, 1H); ESI-MS (m/z) 476.17 (M+H)$^+$.

Example 97

6-(2-{(E)-2-[2-(Cyclobutylmethoxy)-3-difluoromethoxyphenyl]vinyl}-3H-imidazo[4,5-b]pyridin-3-yl)nicotinonitrile

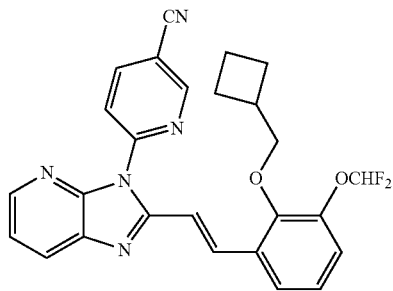 [SMILES: N#Cc1ccc(-n2c(/C=C/c3cccc(OC(F)F)c3OCC3CCC3)nc3cccnc32)nc1]

The title compound was prepared by cyclization of Intermediate 49 in glacial acetic acid as described in Example 52 to give 86 mg of the product as an off-white solid; IR (KBr) 2941, 2232, 1493, 1265, 1124, 1033, 774 cm$^{-1}$; $^1$H NMR (300 MHz, CDCl$_3$) δ 1.86 (br s, 4H), 2.10 (br s, 2H), 2.76 (t, J=7.2 Hz, 1H), 4.02 (d, J=6.6 Hz, 2H), 6.56 (t, J=74.7 Hz, 1H), 7.07-7.18 (m, 2H), 7.34-7.40 (m, 1H), 7.44 (d, J=7.2 Hz, 1H), 7.69 (d, J=15.9 Hz, 1H), 8.13 (d, J=7.2 Hz, 1H), 8.27-8.36 (m, 4H), 8.97 (s, 1H); APCI-MS (m/z) 474.25 (M+H)$^+$.

Example 98

6-(2-{(E)-2-[2-(Cyclopentyloxy)-3-difluoromethoxyphenyl]vinyl}-3H-imidazo[4,5-b]pyridin-3-yl)nicotinonitrile

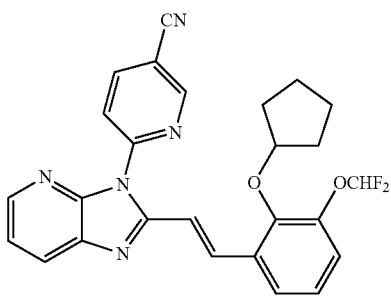 [SMILES: N#Cc1ccc(-n2c(/C=C/c3cccc(OC(F)F)c3OC3CCCC3)nc3cccnc32)nc1]

The title compound was prepared by cyclization of Intermediate 50 in glacial acetic acid as described in Example 52 to give 93 mg of the product as an off-white solid; IR (KBr) 2943, 2230, 1594, 1409, 1265, 1048, 798 cm$^{-1}$; $^1$H NMR (300 MHz, CDCl$_3$) δ 1.59-1.72 (m, 4H), 1.74-1.88 (m, 4H), 4.84 (br s, 1H), 6.55 (t, J=75.3 Hz, 1H), 7.08 (t, J=7.8 Hz, 1H), 7.16 (d, J=7.8 Hz, 1H), 7.33-7.39 (m, 1H), 7.45 (d, J=7.2 Hz, 1H), 7.68 (d, J=16.2 Hz, 1H), 8.12 (d, J=8.4 Hz, 1H), 8.27-8.36 (m, 4H), 8.97 (s, 1H); ESI-MS (m/z) 474.09 (M+H)$^+$.

Example 99

2-[(E)-2-(2-Cyclobutylmethoxy-3-difluoromethoxyphenyl)vinyl]-3-[4-(trifluoromethyl)phenyl]-3H-imidazo[4,5-b]pyridine

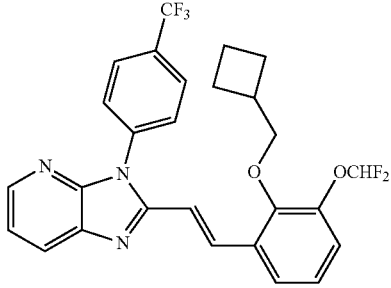 [SMILES: FC(F)Oc1cccc(/C=C/c2nc3cccnc3n2-c2ccc(C(F)(F)F)cc2)c1OCC1CCC1]

The title compound was prepared by cyclization of Intermediate 54 in glacial acetic acid as described in Example 52 to give 47 mg of the product as an off-white solid; IR (KBr) 2981, 1420, 1321, 1102, 1068, 791 cm$^{-1}$; $^1$H NMR (300 MHz, CDCl$_3$) δ 1.76-1.89 (m, 4H), 1.92-2.02 (m, 2H), 2.55-2.62 (m, 1H), 3.96 (d, J=6.0 Hz, 2H), 6.53 (t, J=72.0 Hz, 1H), 7.04-7.16 (m, 3H), 7.29-7.35 (m, 2H), 7.68 (d, J=6.0 Hz, 2H), 7.92 (d, J=6.0 Hz, 2H), 8.12 (d, J=6.0 Hz, 1H), 8.20 (d, J=15.0 Hz, 1H), 8.35 (br s, 1H); ESI-MS (m/z) 516.22 (M+H)$^+$.

Example 100

2-{(E)-2-[2-Cylobutylmethoxy-3-(difluoromethoxy)phenyl]vinyl}-3-[4-(trifluoro methoxy)phenyl]-3H-imidazo[4,5-b]pyridine

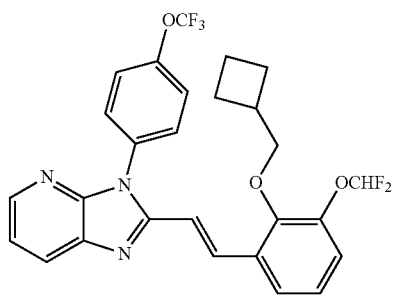 [SMILES: FC(F)Oc1cccc(/C=C/c2nc3cccnc3n2-c2ccc(OC(F)(F)F)cc2)c1OCC1CCC1]

The title compound was prepared by cyclization of Intermediate 55 in glacial acetic acid as described in Example 52 to give 67.5 mg of the product as an off-white solid; IR (KBr) 2936, 2231, 1511, 1423, 1256, 1102, 770 cm$^{-1}$; $^1$H NMR (300 MHz, CDCl$_3$) δ 1.77-1.90 (m, 4H), 1.93-2.01 (m, 2H), 2.59 (t, J=6.0 Hz, 1H), 3.96 (d, J=6.0 Hz, 2H), 6.53 (t, J=72.0 Hz, 1H), 7.06-7.11 (m, 3H), 7.26-7.32 (m, 3H), 7.53 (dd, J=6.0, 15.0 Hz, 3H), 8.11 (d, J=6.0 Hz, 1H), 8.18 (d, J=15.0 Hz, 1H), 8.35 (br s, 1H); ESI-MS (m/z) 532.23 (M+H)$^+$.

Example 101

6-(6-Chloro-2-{(E)-2-[3-(difluoromethoxy)-2-pentyloxyphenyl]vinyl}-3H-imidazo[4,5-b]pyridin-3-yl)nicotinonitrile

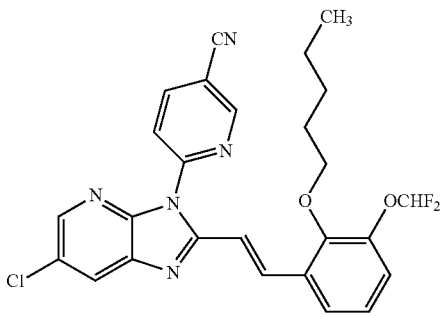 [SMILES: CCCCCOc1c(/C=C/c2nc3cc(Cl)cnc3n2-c2ccc(C#N)cn2)cccc1OC(F)F]

The title compound was prepared by cyclization of Intermediate 51 in glacial acetic acid as described in Example 52 to give 30 mg of the product as an off-white solid; IR (KBr) 2930, 2234, 1413, 1273, 1135, 701 cm$^{-1}$; $^1$H NMR (300 MHz, CDCl$_3$) δ 0.93 (s, 3H), 1.38-1.44 (m, 4H), 1.79 (br s, 2H), 4.02 (s, 2H), 6.56 (t, J=74.4 Hz, 1H), 7.10-7.17 (m, 2H), 7.43 (br s, 1H), 7.69 (d, J=16.2 Hz, 1H), 8.04 (s, 1H), 8.28 (s, 4H), 8.96 (s, 1H); ESI-MS (m/z) 510.17 (M+H)$^+$.

Example 102

6-(6-Chloro-2-{(E)-2-[2-(cyclobutylmethoxy)-3-difluoromethoxyphenyl]vinyl}-3H-imidazo[4,5-b]pyridin-3-yl)nicotinonitrile

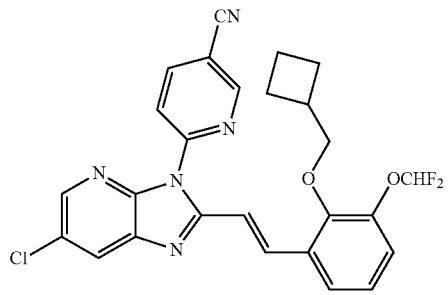 [SMILES: N#Cc1ccc(-n2c(/C=C/c3cccc(OC(F)F)c3OCC3CCC3)nc3cc(Cl)cnc32)nc1]

The title compound was prepared by cyclization of Intermediate 52 in glacial acetic acid as described in Example 52 to give 49 mg of the product as an off-white solid; IR (KBr) 2926, 2236, 1497, 1215, 1120, 758 cm$^{-1}$; $^1$H NMR (300 MHz, CDCl$_3$) δ 1.85 (br s, 4H), 2.05 (br s, 2H), 2.63 (br s, 1H), 3.96 (br s, 2H), 7.18-7.28 (m, 4H), 7.53 (d, J=15.6 Hz, 1H), 7.64 (d, J=7.2 Hz, 1H), 8.17-8.3 (m, 2H), 8.40 (s, 1H), 8.72 (d, J=6.9 Hz, 1H), 9.23 (s, 1H); ESI-MS (m/z) 508.19 (M+H)$^+$.

Example 103

6-(6-Chloro-2-{(E)-2-[2-(cyclopentyloxy)-3-difluoromethoxyphenyl]vinyl}-3H-imidazo[4,5-b]pyridin-3-yl)nicotinonitrile

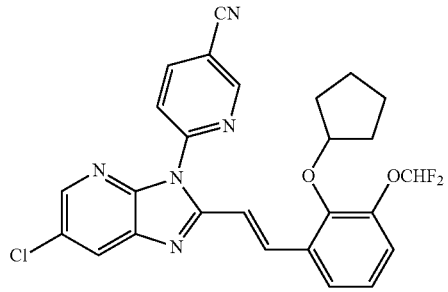 [SMILES: N#Cc1ccc(-n2c(/C=C/c3cccc(OC(F)F)c3OC3CCCC3)nc3cc(Cl)cnc32)nc1]

The title compound was prepared by cyclization of Intermediate 53 in glacial acetic acid as described in Example 52 to give 48 mg of the product as an off-white solid; IR (KBr) 2950, 2231, 1588, 1401, 1267, 1044, 770 cm$^{-1}$; $^1$H NMR (300 MHz, CDCl$_3$) δ 1.57-1.65 (m, 4H), 1.72-1.88 (m, 4H), 4.84 (br s, 1H), 6.54 (t, J=74.7 Hz, 1H), 7.08 (t, J=7.8 Hz, 1H), 7.17 (d, J=7.8 Hz, 1H), 7.45 (br s, 1H), 7.64 (d, J=16.2 Hz, 1H), 8.09 (s, 1H), 8.27-8.35 (m, 4H), 8.97 (s, 1H); ESI-MS (m/z) 508.10 (M+H)$^+$.

Example 104

6-{2-[(E)-2-(2-[Cyclopentyloxy]-3-methoxyphenyl)vinyl]-1H-imidazo[4,5-c]pyridin-1-yl}nicotinonitrile

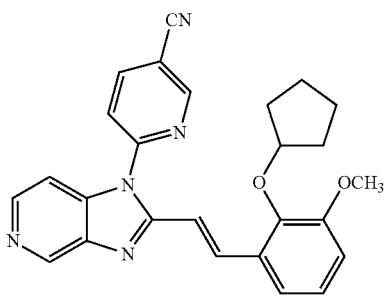 [SMILES: COc1cccc(/C=C/c2nc3cnccc3n2-c2ccc(C#N)cn2)c1OC1CCCC1]

The title compound was prepared by cyclization of Intermediate 44 in glacial acetic acid as described in Example 52 to give 19 mg of the product as an off-white solid; IR (KBr) 2957, 2232, 1590, 1480, 1266, 1048 cm$^{-1}$; $^1$H NMR (300 MHz, DMSO-d$_6$) δ 1.56-1.66 (m, 4H), 1.73-1.77 (m, 4H), 3.82 (s, 3H), 4.89 (s, 1H), 7.08 (s, 2H), 7.30 (d, J=16.2 Hz, 2H), 7.61 (br s, 1H), 8.04 (d, J=8.1 Hz, 1H), 8.23 (d, J=16.2 Hz, 1H), 8.43 (br s, 1H), 8.74 (d, J=7.8 Hz, 1H), 9.10 (s, 1H), 9.27 (s, 1H); APCI-MS (m/z) 438.24 (M+H)$^+$.

Pharmacological Activity

The illustrative examples of the present invention are screened for TRPV3 activity according to a modified procedure described in Tóth, A., Kedei, N., Wang, Y. and Blumberg, P. M. *Life Sciences* (2003), 73, 487-498. The screening of the compounds can be carried out by other methods and procedures known to a person skilled in the art. Such screening methods may be found in (a) Hu, H.-Z. et al. *J. Biol. Chem.* (2004), 279, 35741-35747; (b) Smith, G. D. et al. *Nature* (2002), 418, 186-190; (c) Peier, A. M. et al. *Science* (2002), 296, 2046-2049.

Screening for TRPV3 antagonist using the $^{45}$Calcium uptake assay The inhibition of TRPV3 receptor activation was followed as inhibition of 2-aminoethoxydiphenylborate (2-APB) induced cellular uptake of radioactive calcium. Test compounds were dissolved in dimethyl sulfoxide (DMSO) to prepare 20 mM stock solution and then diluted using plain medium with DMEM/F-12 containing 1.8 mM CaCl$_2$ to get desired concentration. Final concentration of DMSO in the reaction was 0.5% (v/v). Human TRPV3 expressing CHO cells were grown in DMEM/F-12 medium with 10% FBS, 1% penicillin-streptomycin solution, 400 µg/ml of G-418. Cells were seeded 24 h prior to the assay in 96 well plates so as to get ~50,000 cells per well on the day of experiment. Cells were treated with test compounds for 10 minutes followed by addition of 2-APB at a final concentration of 500 µM and 5 µCi/ml$^{45}$Ca$^{+2}$ for 4 minutes. Cells were washed and lysed using buffer containing 1% Triton X-100, 0.1% deoxycholate and 0.1% SDS. Radioactivity in the lysate was measured in Packardt Top count after addition of liquid scintillant. Concentration response curves were plotted as a % of maximal response obtained in the absence of test antagonist. IC$_{50}$ value was calculated from concentration response curve by nonlinear regression analysis using GraphPad PRISM software.

The compounds prepared were tested using the above assay procedure and the results obtained are given in Table 4. Percentage inhibition at concentrations of 1.0 µM and 10.0 µM are given in the table along with IC$_{50}$ details for selected examples. The IC$_{50}$ (nM) values of the compounds are set forth in Table 4 wherein "A" refers to an IC$_{50}$ value of less than 50 nM, "B" refers to IC$_{50}$ value in range of 50.01 to 100.0 nM and "C" refers to an IC$_{50}$ value in range of 100.01 to 500.0 nM and "D" refers to IC$_{50}$ values above 500.0 nM.

TABLE 4

In-vitro screening results of compounds of invention

| Examples | Percentage Inhibition (1 µM) | Percentage Inhibition (10 µM) | IC$_{50}$ in nM |
|---|---|---|---|
| Example 1 | 12.79 | 78.51 | — |
| Example 2 | 3.64 | 85.01 | — |
| Example 3 | 62.12 | 86.59 | D |
| Example 4 | 50.86 | 81.69 | — |
| Example 5 | 38.76 | 69.33 | — |
| Example 6 | 66.84 | 88.95 | D |
| Example 7 | 6.40 | 92.79 | — |
| Example 8 | 91.57 | 97.00 | C |
| Example 9 | 79.71 | 97.94 | D |
| Example 10 | 96.64 | 99.06 | C |
| Example 11 | 94.80 | 97.39 | C |
| Example 12 | 81.44 | 97.65 | C |
| Example 13 | 89.11 | 95.80 | C |
| Example 14 | 93.23 | 97.68 | C |
| Example 15 | 90.33 | 95.11 | D |
| Example 16 | 97.72 | 98.95 | B |
| Example 17 | 84.34 | 95.76 | C |
| Example 18 | 94.25 | 97.28 | C |
| Example 19 | 82.92 | 95.87 | C |
| Example 20 | 0.00 | 52.69 | — |
| Example 21 | 12.96 | 81.94 | — |
| Example 22 | 70.60 | 89.25 | C |
| Example 23 | 56.03 | 84.49 | — |
| Example 24 | 84.68 | 98.01 | D |
| Example 25 | 86.71 | 97.47 | C |
| Example 26 | 70.62 | 91.61 | D |
| Example 27 | 41.77 | 94.66 | — |
| Example 28 | 77.12 | 92.59 | C |
| Example 29 | 78.84 | 93.61 | C |
| Example 30 | 16.42 | 27.53 | — |
| Example 31 | 47.26 | 86.64 | — |
| Example 32 | 9.07 | 0.00 | — |
| Example 33 | 78.17 | 95.34 | C |
| Example 34 | 69.86 | 86.85 | D |
| Example 35 | 54.33 | 77.81 | — |
| Example 36 | 82.80 | 95.96 | C |
| Example 37 | 72.21 | 84.60 | C |
| Example 38 | 48.27 | 59.21 | — |
| Example 39 | 76.81 | 94.20 | C |
| Example 40 | 11.65 | 12.28 | — |
| Example 41 | 57.68 | 86.50 | — |
| Example 42 | 60.18 | 87.34 | — |
| Example 43 | 88.78 | 97.49 | C |
| Example 44 | 60.01 | 87.13 | — |
| Example 45 | 43.35 | 83.81 | — |
| Example 46 | 16.05 | 81.09 | — |
| Example 47 | 22.40 | 79.65 | — |
| Example 48 | 43.49 | 75.78 | — |
| Example 49 | 56.12 | 76.91 | — |
| Example 50 | 26.08 | 46.65 | — |
| Example 51 | 96.19 | 97.83 | B |
| Example 52 | 97.71 | 98.40 | B |
| Example 53 | 95.97 | 98.73 | C |
| Example 54 | 95.31 | 97.66 | B |
| Example 55 | 95.90 | 97.56 | C |
| Example 56 | 96.77 | 98.94 | C |
| Example 57 | 93.01 | 96.10 | C |
| Example 58 | 96.29 | 97.88 | C |
| Example 59 | 95.85 | 97.86 | B |
| Example 60 | 32.14 | 30.23 | — |

TABLE 4-continued

In-vitro screening results of compounds of invention

| Examples | Percentage Inhibition (1 µM) | Percentage Inhibition (10 µM) | IC$_{50}$ in nM |
|---|---|---|---|
| Example 61 | 44.80 | 95.97 | — |
| Example 62 | 92.02 | 95.86 | C |
| Example 63 | 80.81 | 97.71 | C |
| Example 64 | 96.39 | 99.88 | C |
| Example 65 | 94.93 | 97.43 | B |
| Example 66 | 98.56 | 99.55 | C |
| Example 67 | 95.45 | 99.04 | A |
| Example 68 | 95.01 | 99.06 | B |
| Example 69 | 32.72 | 95.54 | — |
| Example 70 | 96.24 | 98.13 | B |
| Example 71 | 53.74 | 79.41 | — |
| Example 72 | 90.81 | 95.55 | C |
| Example 73 | 53.53 | 75.50 | — |
| Example 74 | 1.70 | 1.51 | — |
| Example 75 | 34.36 | 90.74 | — |
| Example 76 | 96.26 | 96.97 | C |
| Example 77 | 93.16 | 98.70 | B |
| Example 78 | 92.67 | 96.81 | B |
| Example 79 | 93.67 | 96.85 | 69.17 (B) |
| Example 80 | 97.56 | 98.80 | B |
| Example 81 | 90.69 | 95.68 | A |
| Example 82 | 97.00 | 98.87 | B |
| Example 83 | 96.71 | 97.74 | A |
| Example 84 | 98.38 | 99.28 | A |
| Example 85 | 71.07 | 90.18 | C |
| Example 86 | 92.64 | 95.21 | C |
| Example 87 | 95.67 | 99.09 | C |
| Example 88 | 25.12 | 71.10 | — |
| Example 89 | 74.21 | 96.63 | C |
| Example 90 | 93.30 | 98.15 | B |
| Example 91 | 95.27 | 99.72 | C |
| Example 92 | 3.02 | 24.46 | |
| Example 93 | 95.17 | 97.63 | B |
| Example 94 | 94.49 | 97.97 | B |
| Example 95 | 93.71 | 97.75 | B |
| Example 96 | 97.10 | 98.11 | B |
| Example 97 | 96.04 | 99.18 | B |
| Example 98 | 95.87 | 100.00 | C |
| Example 99 | 89.52 | 95.83 | D |
| Example 100 | 66.35 | 94.87 | — |
| Example 101 | 30.32 | 85.17 | — |
| Example 102 | 95.07 | 98.07 | B |
| Example 103 | 98.35 | 97.83 | B |
| Example 104 | 48.69 | 98.26 | — |

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above.

All publications, patents, and patent applications cited in this application are herein incorporated by reference to the same extent as if each individual publication, patent, or patent application was specifically and individually indicated to be incorporated herein by reference.

The invention claimed is:

1. A compound of the formula (II):

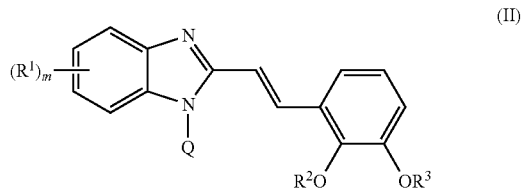

(II)

wherein,
at each occurrence, $R^1$ is independently selected from hydrogen, halogen, substituted or unsubstituted alkyl, alkoxy, haloalkyl, and haloalkoxy;
'm' is an integer ranging from 1 to 4, both inclusive;
Q is substituted or unsubstituted, aryl, arylalkyl, or heteroaryl;
wherein substituents, may be one or more and are independently selected from halogen, hydroxyl, nitro, cyano, amino, COOR$^a$, C(O)NR$^5$R$^6$, substituted or unsubstituted alkyl, alkoxy, haloalkyl, haloalkoxy, cycloalkyl, and cycloalkoxy;
R$^a$ is hydrogen or substituted or unsubstituted alkyl;
R$^2$ and R$^3$, may be same or different, are independently selected from the group consisting of hydrogen, substituted or unsubstituted alkyl, haloalkyl, alkoxyalkyl, cycloalkyl, cycloalkylalkyl, arylalkyl, heteroarylalkyl, heterocyclic group, and heterocyclylalkyl; and
at each occurrence, R$^5$ and R$^6$, may be same or different, are independently selected from hydrogen, substituted or unsubstituted alkyl, haloalkyl, cycloalkyl, aryl and heteroaryl, cycloalkylalkyl, arylalkyl, and heteroarylalkyl;
or a pharmaceutically acceptable salt thereof.

2. The compound according to claim 1, wherein Q is substituted or unsubstituted aryl.

3. The compound according to claim 2, wherein aryl is substituted or unsubstituted phenyl.

4. The compound according to claim 1, wherein Q is substituted or unsubstituted arylalkyl.

5. The compound according to claim 4, wherein arylalkyl is benzyl.

6. The compound according to claim 1, wherein Q is substituted or unsubstituted heteroaryl.

7. The compound according to claim 6, wherein heteroaryl is pyridine.

8. The compound according to claim 1, wherein $R^2$ is hydrogen, substituted or unsubstituted alkyl, cycloalkyl, cycloalkylalkyl or arylalkyl.

9. The compound according to claim 1, wherein $R^3$ is hydrogen, substituted or unsubstituted alkyl or haloalkyl.

10. The compound according to claim 1 selected from:
2-{(E)-2-[2-(Cyclopropylmethoxy)-3-methoxyphenyl]vinyl}-1-pyridin-2-yl-1H-benzimidazole;
2-[(E)-2-(2-Cyclopentyloxy-3-methoxyphenyl)vinyl]-1-pyridin-2-yl-1H-benzimidazole;
1-(5-Chloropyridin-2-yl)-2-{(E)-2[2-(cyclopentyloxy)-3-methoxyphenyl]vinyl}-1H-benzimidazole;
2-[(E)-2-(2-[Cyclopentyloxy]-3-methoxyphenyl)vinyl]-1-(5-nitropyridin-2-yl)-1H-benzimidazole;
2-[(E)-2-(2-Benzyloxy-3-methoxyphenyl)vinyl]-1-(3,5-dichloropyridin-2-yl)-1H-benzimidazole;
or a pharmaceutically acceptable salt thereof.

11. The compound according to claim 1 selected from:
1-(3,5-Dichloropyridin-2-yl)-2-{(E)-2-[2-(2-fluorobenzyloxy)-3-methoxyphenyl]vinyl}-1H-benzimidazole;
2-{2-[(E)-2-(2-Cyclopentyloxy-3-methoxyphenyl)vinyl]-1H-benzimidazol-1-yl}nicotinonitrile;
6-{2-[(E)-2-(2-Butoxy-3-methoxyphenyl)vinyl]-1H-benzimidazol-1-yl}nicotinonitrile;
6-{2-[(E)-2-(2-Isopropoxy-3-methoxyphenyl)vinyl]-1H-benzimidazol-1-yl}nicotinonitrile;
6-{2-[(E)-2-(2-(1-Ethylpropoxy)-3-methoxyphenyl)vinyl]-1H-benzimidazol-1-yl}nicotinonitrile;
or a pharmaceutically acceptable salt thereof.

12. The compound according to claim 1 selected from:
6-(2-{(E)-2-[3-methoxy-2-(2-methylpropoxy)phenyl]ethenyl}-1H-benzimidazol-1-yl)pyridine-3-carbonitrile;
6-{2-[(E)-2-(2-[Cyclopropylmethoxy]-3-methoxyphenyl)vinyl]-1H-benzimidazol-1-yl}nicotinonitrile;
6-{2-[(E)-2-(2-Cyclopentyloxy-3-methoxyphenyl)vinyl]-1H-benzimidazol-1-yl}nicotinonitrile;
6-(2-{(E)-2-[2-(2-Fluorobenzyloxy)-3-methoxyphenyl]vinyl}-1H-benzimidazol-1-yl) nicotinonitrile;
6-{2-[(E)-2-(2-(2-Cyanobenzyloxy)-3-methoxyphenyl)vinyl]-1H-benzimidazol-1-yl} nicotinonitrile;
or a pharmaceutically acceptable salt thereof.

13. The compound according to claim 1 selected from:
6-{2-[(E)-2-(3-Methoxy-2-{[2-(trifluoromethyl)benzyl]oxy}phenyl)vinyl]-1H-benzimidazole-1-yl}nicotinonitrile;
6-(2-{(E)-2-[2-(2,6-Difluorobenzyloxy)-3-methoxyphenyl]vinyl}-1H-benzimidazol-1-yl)nicotinonitrile;
6-(2-{(E)-2-[2-(2,4-Difluorobenzyloxy)-3-methoxyphenyl]vinyl}-1H-benzimidazol-1-yl)nicotinonitrile;
Ethyl 6-{2-[(E)-2-(2-[Cyclopentyloxy]-3-methoxyphenyl)vinyl]-1H-benzimidazol-1-yl}pyridazine-3-carboxylate;
6-{2-[(E)-2-(2-[Cyclopentyloxy]-3-methoxyphenyl)vinyl]-1H-benzimidazol-1-yl}pyridazine-3-carbonitrile;
or a pharmaceutically acceptable salt thereof.

14. The compound according to claim 1 selected from:
2-{(E)-2-[2-Cyclopentyloxy)-3-methoxyphenyl]vinyl}-1-pyrimidin-2-yl-1H-benzimidazole;
1-(5-Bromopyrimidin-2-yl)-2-{(E)-2-[2-(1-ethylpropoxy)-3-methoxyphenyl]vinyl}-1H-benzimidazole;
1-(5-Bromopyrimidin-2-yl)-2-[(E)-2-(2-cyclopentyloxy-3-methoxyphenyl)vinyl]-1H-benzimidazole;
2-[(E)-2-(2-Cyclopentyloxy-3-methoxyphenyl)vinyl]-1-[3-(trifluoromethyl)pyridin-2-yl]-1H-benzimidazole;
2-[(E)-2-(2-Isopropoxy-3-methoxyphenyl)vinyl]-1-(5-trifluoromethylpyridin-2-y1)-1H-benzimidazole;
or a pharmaceutically acceptable salt thereof.

15. The compound according to claim 1 selected from:
2-[(E)-2-(2-Cyclopropyloxy-3-methoxyphenyl)vinyl]-1-(5-trifluromethylpyridin-2-yl)-1H-benzimidazole;
2-[(E)-2-(2-Cyclopentyloxy-3-methoxyphenyl)vinyl]-1-[5-(trifluoromethyl) pyridin-2-yl]-1H-benzimidazole;
2-[(E)-2-(2-Benzyloxy-3-methoxyphenyl)vinyl]-1[5-(trifluoromethyl)pyridin-2-yl]1H-benzimidazole;
1-[3-Chloro-5-(trifluoromethyl)pyridin-2-yl]-2-[(E)-2-(2-cyclopentyloxy-3-methoxyphenyl)vinyl]-1H-benzimidazole;
Methyl 6-(2-{(E)-2-[2-(Cyclopentyloxy)-3-methoxyphenyl]vinyl}-1H-benzimidazol-1-yl)nicotinate;
or a pharmaceutically acceptable salt thereof.

16. The compound according to claim 1 selected from:
2-[(E)-2-(2-Cyclopropylmethoxy-3-methoxyphenyl)vinyl]-1-(4-methylphenyl)-1H-benzimidazole;
2-[(E)-2-(2-Cyclopentyloxy-3-methoxyphenyl)vinyl]-1-(2-methoxyphenyl)-1H-benzimidazole;
4-{2-[(E)-2-(2-Cyclopropylmethoxy-3-methoxyphenyl)vinyl]-1H-benzimidazol-1-yl}benzonitrile;
4-{2-[(E)-2-(2-Benzyloxy-3-methoxyphenyl)vinyl]-1H-benzimidazol-1-yl}benzonitrile;
2-[(E)-2-(2-Cyclopentyloxy-3-methoxyphenyl)vinyl]-1-[4-(trifluoromethyl) phenyl]-1H-benzimidazole;
or a pharmaceutically acceptable salt thereof.

17. The compound according to claim 1 selected from:
4-{2-[(E)-2-(2-Butoxy-3-methoxyphenyl)vinyl]-1H-benzimidazol-1-yl}benzonitrile;
2-[(E)-2-(2-Cyclopropylmethoxy-3-methoxyphenyl)vinyl]-1-[4-(trifluoromethyl) phenyl]-1H-benzimidazole;
5-{2-[(E)-2-(2-Cyclopropylmethoxy-3-methoxyphenyl)vinyl]-1H-benzimidazol-1-yl}-4-fluorobenzonitrile;
4-{2-[(E)-2-(2-Cyclopropylmethoxy-3-methoxyphenyl)vinyl]-1H-benzimidazol-1-yl}-3-fluorobenzonitrile;
2-[(E)-2-(2-Cyclopentyloxy-3-methoxyphenyl)vinyl]-1-(4-tert-butylbenzyl)-1H-benzimidazole;
or a pharmaceutically acceptable salt thereof.

18. The compound according to claim 1 selected from:
1-(2,4-Difluorobenzyl)-2-[(E)-2-(2-cyclopropylmethoxy3-methoxyphenyl)vinyl]-1H-benzimidazole;
4-({2-[(E)-2-(2-Cyclopropylmethoxy-3-methoxyphenyl)vinyl]-1H-benzimidazol-1-yl}methyl) benzonitrile;
4-({2-[(E)-2-(2-Cyclopentyloxy-3-methoxyphenyl)vinyl]-1H-benzimidazol-1-yl}methyl) benzonitrile;
4-({2-[(E)-2-(2-{2-Fluorobenzyloxy}-3-methoxyphenyl)vinyl]-1H-benzimidazol-1-yl}methyl) benzonitrile;
2-[(E)-2-(2-Cylopropymethoxy-3-methoxyphenyl)]-1-(2-thienyl)-1H-benzimidazole;
or a pharmaceutically acceptable salt thereof.

19. The compound according to claim 1 selected from:
2-[(E)-2-(2-Cyclopropyloxy-3-methoxyphenyl)vinyl]-1-(1,3-thiazol-2-yl)-1H-benzimidazole;
2-[(E)-2-(2-Cyclopentyloxy-3-methoxyphenyl)vinyl]-1-(1,3-thiazol-2-yl)-1H-benzimidazole;
2-{2-(E)-2-(2-[Cyclopentyloxy]-3-methoxyphenyl)vinyl]-1H-benzimidazol-1-yl}-1,3-thiazole-5-carbonitrile;
2-{2-(E)-2-(2-Cyclopentyloxy-3-methoxyphenyl)vinyl]-1H-benzimidazol-1-yl}-4-methyl-1,3-thiazole-5-carbonitrile;
2-{2-(E)-2-(2-Cyclopropylmethoxy-3-methoxyphenyl)vinyl]-1H-benzimidazol-1-yl}-1,3-benzothiazole;
or a pharmaceutically acceptable salt thereof.

20. The compound according to claim 1 selected from:
6-{2-(E)-2-(2-Cyclopentyloxy-3-methoxyphenyl)vinyl]-6-methoxy-1H-benzimidazol-1-yl}nicotinonitrile;
6-(6-Chloro-2-{(E)-2-[3-methoxy-2-(2-methylpropoxy)phenyl]ethenyl}-1-1H-benzimidazol-1-yl)pyridine-3-carbonitrile;
6-{2-(E)-2-(2-Cyclopentyloxy-3-methoxyphenyl)vinyl]-6-fluoro-1H-benzimidazol-1-yl}nicotinonitrile;
6-{6-Chloro-2-[(E)-2-(2-cyclopentyloxy-3-methoxyphenyl)vinyl]-1H-benzimidazol-1-yl}nicotinonitrile;
6-{5-chloro-2-(E)-2-(2-cyclopentyloxy-3-methoxyphenyl)vinyl]-1H-benzimidazol-1-yl}nicotinonitrile;
or a pharmaceutically acceptable salt thereof.

21. The compound according to claim 1 selected from:
6-{2-(E)-2-(2-[Cyclopentyloxy]-3-methoxyphenyl)vinyl]-5-methoxy-1H-benzimidazol-1-yl}nicotinonitrile;
6-{2-[(E)-2-(2-[Cyclopentyloxy]-3-methoxyphenyl)vinyl]-5-(trifluoromethyl)-1H-benzimidazol-1-yl}nicotinonitrile;

6-{6-(Difluoromethoxy)-2-[(E)-2-(2-[cyclopentyloxy]-3-methoxyphenyl)vinyl]-1H-benzimidazol-1-yl}nicotinonitrile;

6-{2-[(E)-2-(2-[Cyclopentyloxy]-3-methoxyphenyl)vinyl]-5-(difluoromethoxy)-1H-benzimidazol-1-yl}nicotinonitrile;

Methyl 6-{2-[(E)-2-(2-Cyclopentyloxy-3-methoxyphenyl)vinyl]-6-fluoro-1H-benzimidazol-1-yl}nicotinate;

or a pharmaceutically acceptable salt thereof.

22. The compound according to claim 1 selected from:

2-{2-[(E)-2-(2-Cyclopentyloxy-3-methoxyphenyl)vinyl]-5,6-difluoro-1H-benzimidazol-1-yl}nicotinonitrile;

6-{2-[(E)-2-(2-[Cyclopentyloxy]-3-methoxyphenyl)vinyl]-5,6-dimethyl-1H-benzimidazol-1-yl}nicotinonitrile;

6-{2-[(E)-2-(2-Ethoxy-3-methoxyphenyl)vinyl]-5,6-difluoro-1H-benzimidazol-1-yl}nicotinonitrile;

6-{2-[(E)-2-(2-Butoxy-3-methoxyphenyl)vinyl]-5,6-difluoro-1H-benzimidazol-1-yl}-nicotinonitrile;

or a pharmaceutically acceptable salt thereof.

23. The compound according to claim 1 selected from:

6-{5,6-Difluoro-2-[(E)-2-(2-isobutoxy-3-methoxyphenyl)vinyl]-1H-benzimidazol-1-yl}nicotinonitrile;

6-{2-[(E)-2-(2-Cyclobutylmethoxy-3-methoxyphenyl)vinyl]-5,6-difluoro-1H-benzimidazol-1-yl nicotinonitrile;

6-{5,6-Difluoro-2-[(E)-2-(2-hydroxy-3-methoxyphenyl)vinyl]-1H-benzimidazol-1-yl}nicotinonitrile;

6-{5-Chloro-2-[(E)-2-(2-cyclopentyloxy-3-methoxyphenyl)vinyl]-6-(trifluoromethyl)-1H-benzimidazol-1-yl}nicotinonitrile;

or a pharmaceutically acceptable salt thereof.

24. The compound according to claim 1 selected from:

6-{5,6-Dichloro-2-[(E)-2-(2-cyclopentyloxy-3-methoxyphenyl)vinyl]-1H-benzimidazol-1-yl}nicotinonitrile;

Ethyl 6-{2-[(E)-2-(2-cyclopentyloxy-3-methoxyphenyl)vinyl]-5,6-difluoro-1H-benzimidazol-1-yl}pyridazine-3-carboxylate;

6-{2-[(E)-2-(2-Cyclopentyloxy-3-methoxyphenyl)vinyl]-5,6-difluoro-1H-benzimidazol-1-yl}pyridazine-3-carboxylic acid;

6-{2-[(E)-2-(2-Cyclopentyloxy-3-methoxyphenyl)vinyl]-5,6-difluoro-1H-benzimidazol-1-yl}pyridazine-3-carboxamide;

6-{2-[(E)-2-(2-Cyclopentyloxy-3-methoxyphenyl)vinyl]-5,6-difluoro-1H-benzimidazol-1-yl}pyridazine-3-carbonitrile;

or pharmaceutically acceptable salt thereof.

25. The compound according to claim 1 selected from:

6-{2-[(E)-2-(2-(1-ethylpropoxy)-3-methoxyphenyl)vinyl]-5,6-difluoro-1H-benzimidazol-1-yl}nicotinonitrile;

6-{5,7-Difluoro-2-[(E)-2-(2-pentyloxy-3-methoxyphenyl)vinyl]-1H-benzimidazol-1-yl}nicotinonitrile;

6-{5,7-Difluoro-2-[(E)-2-(2-[cyclopentyloxy]-3-methoxyphenyl)vinyl]-1H-benzimidazol-1-yl}nicotinonitrile;

6-{2-[(E)-2-(2-pentyloxy-3-methoxyphenyl)vinyl]-4,5,6-trifluoro-1H-benzimidazol-1-yl}nicotinonitrile;

or pharmaceutically acceptable salt thereof.

26. The compound according to claim 1 selected from:

6-(2-{(E)-2[3-(Difluoromethoxy)-2-pentyloxyphenyl]vinyl}-5,6-difluoro-1H-benzimidazol-1-yl)nicotinonitrile;

6-(2-{(E)-2[2-(Cyclobutylmethoxy)-3-difluoromethoxyphenyl]vinyl}-5,6-difluoro-1H-benzimidazol-1-yl)nicotinonitrile;

6-(2-{(E)-2-[2-(Cyclopentyloxy)-3-difluoromethoxyphenyl-]vinyl}-5,6-difluoro-1H-benzimidazol-1-yl)nicotinonitrile;

2-[(E)-2-(2-butoxy-3-methoxyphenyl)vinyl]-1-(5-trifluoromethylpyridin-2-yl)-1H-benzimidazole;

or pharmaceutically acceptable salt thereof.

27. A compound selected from:

6-{5,6-Difluoro-2-[(E)-2-(2-pentoxy-3-methoxyphenyl)vinyl]-1H-benzimidazol-1-yl}nicotinonitrile;

6-{2-[(E)-2-(2-Cyclopentyloxy-3-methoxyphenyl)vinyl]-5,6-difluoro-1H-benzimidazol-1-yl}nicotinonitrile;

6-{6-Chloro-2-[(E)-2-(2-[cyclopentyloxy]-3-methoxyphenyl)vinyl]-5-fluoro-1H-benzimidazol-1-yl}nicotinonitrile; and 6-{4,6-Difluoro-2-[(E)-2-(2-[cyclopentyloxy]-3-methoxyphenyl)vinyl]-1H-benzimidazol-1-yl}nicotinonitrile or pharmaceutically acceptable salt thereof.

28. A pharmaceutical composition comprising a compound according claim 1, either as a free base or pharmaceutically acceptable salt form and a pharmaceutically acceptable excipient.

29. The pharmaceutical composition according to claim 28, wherein the pharmaceutically acceptable excipient is a carrier or diluent.

30. A method for preventing, ameliorating or treating a disease, disorder, syndrome or condition modulated by a vanilloid receptor in a subject in need thereof said method comprising administering to said subject a therapeutically effective amount of a compound according to claim 1, wherein the disease, disorder, syndrome or condition is selected from the group consisting of pain, acute pain, chronic pain, nociceptive pain, neuropathic pain, post-operative pain, dental pain, cancer pain, cardiac pain arising from an ischemic myocardium and pain due to migraine.

31. A method for ameliorating or treating a disease, disorder, syndrome or condition modulated by a vanilloid receptor in a subject in need thereof, wherein the treating consists of inhibiting or relieving, said method comprising administering to said subject a therapeutically effective amount of a compound according to claim 1, wherein the disease, disorder, syndrome or condition is selected from the group consisting of pain, acute pain, chronic pain, nociceptive pain, neuropathic pain, post-operative pain, dental pain, cancer pain, cardiac pain arising from an ischemic myocardium, pain due to migraine, arthralgia, neuropathies, neuralgia, trigeminal neuralgia nerve injury, diabetic neuropathy, retinopathy, neurotic skin disorder, stroke, urinary bladder hypersensitiveness, urinary incontinence, vulvodynia, gastrointestinal disorders such as irritable bowel syndrome, gastro-esophageal reflux disease, enteritis, ileitis, stomach-duodenal ulcer, inflammatory bowel disease, Crohn's disease, celiac disease, an inflammatory disease such as pancreatitis, a respiratory disorder such as allergic and non-allergic rhinitis, asthma or chronic obstructive pulmonary disease, irritation of skin, eye or mucous membrane, dermatitis, pruritic conditions such as uremic pruritus, fervescence, muscle spasms, emesis, dyskinesias, depression, Huntington's disease, memory deficits, restricted brain function, amyotrophic lateral sclerosis (ALS), dementia, arthritis, rheumatoid arthritis, osteoarthritis, diabetes, obesity, urticaria, actinic keratosis, keratocanthoma, alopecia, Meniere's disease, tinnitus, hyperacusis, anxiety disorders and benign prostate hyperplasia.

32. The method according to claim 31 wherein the disease, disorder, syndrome or condition is pain.

33. The method according to claim 32, wherein the pain is acute pain.

34. The method according to claim 32, wherein the pain is chronic pain.

35. The method according to claim 31, wherein the pain is post-operative pain.

36. The method according to claim 31 wherein the disease, disorder, syndrome or condition is osteoarthritis.

37. The method according to claim 31 wherein the disease, disorder, syndrome or condition is rheumatoid arthritis.

38. The method according to claim 32 wherein the pain is neuropathic pain.

39. The method according to claim 31 wherein the disease, disorder, syndrome or condition is inflammation.

40. A compound of claim 1, or a pharmaceutically acceptable salt thereof, that possesses an $IC_{50}$ value of less than 100 nM as measured by a $^{45}$Calcium uptake assay.

* * * * *